US012686887B2

(12) United States Patent
Zhong et al.

(10) Patent No.: US 12,686,887 B2
(45) Date of Patent: Jul. 21, 2026

(54) SUBSTRATES AND OPTICAL SYSTEMS AND METHODS OF USE THEREOF

(71) Applicant: Pacific Biosciences of California, Inc., Menlo Park, CA (US)

(72) Inventors: Cheng Frank Zhong, Fremont, CA (US); Paul Lundquist, San Francisco, CA (US); Mathieu Foquet, Newark, CA (US); Jonas Korlach, Camas, WA (US); Hovig Bayandorian, Berkeley, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 192 days.

(21) Appl. No.: 18/773,845

(22) Filed: Jul. 16, 2024

(65) Prior Publication Data

US 2025/0043345 A1     Feb. 6, 2025

Related U.S. Application Data

(63) Continuation of application No. 18/085,837, filed on Dec. 21, 2022, now Pat. No. 12,043,868, which is a continuation of application No. 17/202,914, filed on Mar. 16, 2021, now Pat. No. 11,560,591, which is a continuation of application No. 16/876,542, filed on May 18, 2020, now Pat. No. 10,968,482, which is a (Continued)

(51) Int. Cl.
| | |
|---|---|
| *G01N 21/64* | (2006.01) |
| *C12Q 1/68* | (2018.01) |
| *C12Q 1/6825* | (2018.01) |
| *C12Q 1/6874* | (2018.01) |
| *G01N 21/77* | (2006.01) |
| *G01N 33/543* | (2006.01) |

(52) U.S. Cl.
CPC ............ *C12Q 1/6874* (2013.01); *C12Q 1/68* (2013.01); *C12Q 1/6825* (2013.01); *G01N 21/6428* (2013.01); *G01N 21/648* (2013.01); *G01N 21/7703* (2013.01); *G01N 33/54373* (2013.01); *G01N 2021/6463* (2013.01); *G01N 2201/06113* (2013.01); *G01N 2201/0638* (2013.01); *G01N 2201/08* (2013.01)

(58) Field of Classification Search
CPC ...... C12Q 1/6874; C12Q 1/68; C12Q 1/6825; G01N 21/6428; G01N 21/648; G01N 21/7703; G01N 33/54373; G01N 2021/6463; G01N 2201/06113; G01N 2201/0638; G01N 2201/08; G01N 2021/6478; G01N 21/6454
See application file for complete search history.

(56) References Cited

U.S. PATENT DOCUMENTS

| | | | | |
|---|---|---|---|---|
| 2004/0120644 A1* | 6/2004 | Chou | ..................... | G02B 6/138 |
| | | | | 385/129 |
| 2008/0260941 A1* | 10/2008 | Jin | ....................... | B01J 37/0009 |
| | | | | 427/372.2 |

* cited by examiner

*Primary Examiner* — Kiho Kim
(74) *Attorney, Agent, or Firm* — Patrick S. Morris

(57)     ABSTRACT

This invention provides analytical devices for use in various applications, including detection of single-molecule analytical reactions. Methods for propagating optical energy within a substrate are provided. Devices comprising waveguide substrates, dielectric omnidirectional reflectors, and optical couplers are provided. Waveguide substrates with improved uniformity of optical energy intensity across one or more waveguides and enhanced waveguide illumination efficiency within an analytic detection region of the arrays are provided.

14 Claims, 28 Drawing Sheets

Related U.S. Application Data continuation of application No. 16/289,513, filed on Feb. 28, 2019, now Pat. No. 10,697,012, which is a continuation of application No. 15/629,631, filed on Jun. 21, 2017, now Pat. No. 10,280,457, which is a continuation of application No. 14/949,313, filed on Nov. 23, 2015, now Pat. No. 9,719,138, which is a continuation of application No. 13/902,113, filed on May 24, 2013, now Pat. No. 9,222,123, which is a continuation of application No. 13/274,547, filed on Oct. 17, 2011, now Pat. No. 8,274,040, which is a continuation of application No. 12/560,308, filed on Sep. 15, 2009, now Pat. No. 8,471,230.

(60) Provisional application No. 61/192,326, filed on Sep. 16, 2008.

A.

B.

B.

A.

B.

A.

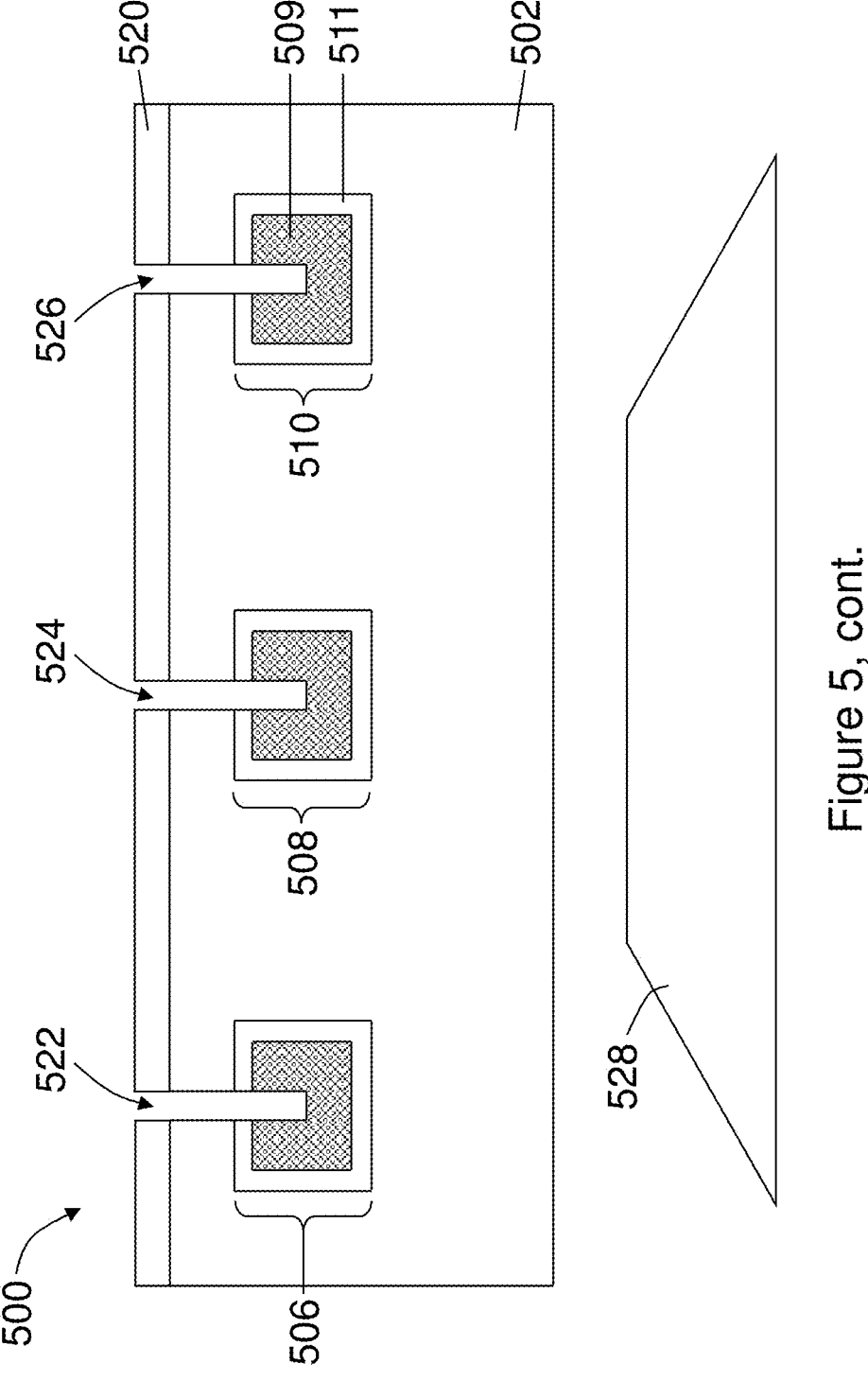
Figure 5, cont.

SUBSTRATES AND OPTICAL SYSTEMS AND METHODS OF USE THEREOF

CROSS-REFERENCE TO RELATED APPLICATIONS

This application is a continuation of U.S. patent application Ser. No. 18/085,837, filed Dec. 21, 2022, which is a continuation of U.S. patent application Ser. No. 17/202,914, filed Mar. 16, 2021, now U.S. Pat. No. 11,560,591, which is a continuation of U.S. patent application Ser. No. 16/876, 542, filed May 18, 2020, now U.S. Pat. No. 10,968,482, which is a continuation of U.S. patent application Ser. No. 16/289,513, filed Feb. 28, 2019, now U.S. Pat. No. 10,697, 012, which is a continuation of U.S. patent application Ser. No. 15/629,631, filed Jun. 21, 2017, now U.S. Pat. No. 10,280,457, which is a continuation of U.S. patent application Ser. No. 14/949,313, filed Nov. 23, 2015, now U.S. Pat. No. 9,719,138, which is a continuation of U.S. patent application Ser. No. 13/902,113, filed May 24, 2013, now U.S. Pat. No. 9,222,123, which is a continuation of U.S. patent application Ser. No. 13/274,547, filed Oct. 17, 2011, now U.S. Pat. No. 8,274,040, which is a continuation of U.S. patent application Ser. No. 12/560,308, filed Sep. 15, 2009, now U.S. Pat. No. 8,471,230, which claims the benefit of U.S. Provisional Application No. 61/192,326, filed Sep. 16, 2008, the disclosures of which are incorporated herein by reference in their entireties for all purposes.

BACKGROUND OF THE INVENTION

A number of analytical operations benefit from the illumination of substrates in order to accomplish the desired analysis. For example, interrogation of biopolymer array substrates typically employs wide area illumination, e.g., in a linearized beam, flood or reciprocating spot operation. Such illumination allows interrogation of larger numbers of analytical features, e.g., molecule groups, in order to analyze the interaction of such molecule groups with a sample applied to the array.

For certain analytical operations, a tightly controlled illumination strategy is desirable. For example, it may be desirable to provide strict control of the volume of material that is illuminated, as well as the overall area that is illuminated, effectively controlling illumination not only in the x or y axes of a planar substrate, but also in the z axis, e.g., extending away from the substrate. One example of controlled illumination that accomplishes both lateral (x and y) and volume (z) control is the use of zero-mode waveguides as a base substrate for analyzing materials. See, U.S. Pat. Nos. 6,991,726 and 7,013,054, the full disclosures of which are incorporated herein by reference in their entireties for all purposes. Briefly, zero-mode waveguide array substrates employ an opaque mask layer, e.g., aluminum, chromium, or the like, deposited over a transparent substrate layer, through which are disposed a series of apertures through to the transparent layer. Because the apertures are of sufficiently small cross sectional dimensions, e.g., on the order of 50-200 nm in cross section, they prevent propagation of light through them that is below a cut-off frequency. While some light will enter the aperture or core, its intensity decays exponentially as a function of the distance from the aperture's opening. As a result, a very small volume of the core is actually illuminated with a relevant level of light. Such ZMW arrays have been illuminated using a number of the methods, including spot illumination, flood illumination and line illumination (using a linearized beam) (See, e.g., co-pending Published U.S. Patent Application No. 2007-0188750, and published International Patent Application No. WO 2007/095119, the full disclosures of which are incorporated herein by reference in their entireties for all purposes).

A second optical confinement strategy employs substrates that include waveguides, such that the exponential decay of light outside the waveguide may be exploited in a surface region of the substrate to selectively illuminate materials provided upon that surface. Waveguide-based illumination strategies can be used to illuminate materials within ZMWs and other structures, such as wells positioned on the surface. Further details regarding some such illumination schemes can be found in U.S. Patent Publication No. 2008-0128627, the full disclosure of which is incorporated herein by reference in its entirety for all purposes.

The present invention provides new substrates for waveguide arrays and methods of illuminating analytes disposed upon the substrates, as will be apparent upon review of the following.

SUMMARY OF THE INVENTION

Improved substrates of the invention find use in various applications, e.g., for analyte analysis, monitoring of enzymatic reactions, such as nucleic acid and polypeptide polymerization reactions, detecting binding and other intermolecular interactions, genotyping, and many others. The substrates, methods, and systems are particularly suitable for detecting, monitoring, and analyzing single molecules, molecular complexes, or intermolecular reactions. As opposed to technologies that allow only bulk detection, the ability to detect individual molecules and reactions facilitates analyses that are not possible with bulk detection, e.g., measurements of kinetics of an individual enzyme or enzyme complex in real time. For example, single polymerase or ribosome complexes can be monitored during polymerization of nucleic acids or polypeptides, respectively.

The present invention provides substrates that include features, e.g., waveguides, optical gratings, various conformations of surface regions to be illuminated, various waveguide configurations, separate substrates for optical splitting and biosensing functions, single substrates that perform both optical splitting and biosensing functions, additional substrate layers to reduce optical scattering and/or increase detection efficiency, and substrates with improved analyte immobilization capabilities, which can be particularly desirable for these applications. The invention provides devices and methods that utilize optical gratings for normalizing optical energy intensity among arrayed waveguides and enhancing waveguide-mediated illumination (or "waveguide illumination") efficiency within an analyte region of a substrate. The invention also provides waveguide configurations, e.g., waveguides at a first depth within a substrate for distributing optical energy around the substrate, and waveguides at a second depth disposed upon or within the substrate for illuminating analyte regions, to reduce propagation losses within waveguides of a waveguide array. The invention also provides tapered and multi-polarized waveguides, waveguides with tapered waveguide cladding layers, waveguides with refractive indices that vary along their length (e.g., in the core and/or cladding layer), and arrayed waveguides that are created from a single waveguide that passes back and forth within the waveguide substrate. The invention further provides waveguides configured with a bend to reduce background signal and, thereby, increase the signal-to-background ratio. Further, the invention provides waveguide arrays for delivering optical energy to a plurality of apertures, e.g., nanoholes or zero-mode waveguides. The invention also provides waveguide arrays that include an additional substrate layer and or "dummy nanoholes" to reduce scattering effects that result from a plurality of analyte regions being disposed proximal to a waveguide core, as well as non-uniform spacing of the analyte regions disposed proximal to a waveguide core for enhanced propagation of optical energy through the core. The invention further provides waveguide arrays that include deposition patterns of immobilization compounds for immobilizing analytes upon a substrate of the array. In addition, the invention provides waveguide substrates that allow biased surface chemistry within an aperture disposed upon the substrate, e.g., such as the biased surface chemistry used in convention zero-mode waveguide applications. The invention also provides integrated optical systems that include microlens arrays, sensor arrays, multilayer dielectric stacks, and/or objective lenses positioned on both sides of a waveguide substrate.

In one aspect, the invention provides analytic devices for normalizing optical energy intensity among arrayed waveguides comprising a substrate comprising a first surface, two or more waveguides disposed upon or within the substrate that are configured to receive optical energy at a portion of the two or more waveguides comprising an optical grating, and an analyte region disposed sufficiently proximal to a core of the at least one of the two or more waveguides, such that the analyte region is illuminated by an evanescent field emanating from the core when optical energy is passed through the waveguide. The device can optionally comprise a source of a single beam of optical energy, a diffractive optical element for splitting the single beam of optical energy into two or more beams of optical energy, and/or a relay lens and microscope objective for focusing one of the two or more beams of optical energy at the optical grating disposed within the waveguide. Optionally, the analyte region of the devices is disposed within an aperture or well disposed over an exposed surface of the waveguide, e.g., such as a nanohole or a zero-mode waveguide. Optionally, the analyte region is disposed within a nanometer-scale aperture that extends into the waveguide. Further, the analyte region of the device can optionally comprise an analyte.

In a related aspect, the invention provides methods for illuminating an analyte comprising transmitting optical energy to two or more waveguides disposed upon or within a substrate and configured to receive optical energy, disposing an optical grating within the two or more waveguides, and disposing an analyte region sufficiently proximal to a core of at least one of the two or more waveguides, such that the analyte is illuminated by an evanescent field emanating from the waveguide when optical energy is passed through the waveguide. Optionally, the method comprises providing a source of a single beam of optical energy, providing a diffractive optical element for splitting the beam into two or more beams, and/or providing at least one relay lens and at least one microscope objective for focusing one of the two or more beams at the optical grating disposed within the two or more waveguides.

The invention also provides analytic devices comprising a substrate comprising a first surface, at least one waveguide disposed upon within the substrate that comprises a diffraction grating pair, where the diffraction grating pair flanks a portion of the waveguide that is proximal to a detection region of the substrate and where the diffraction grating pair intensifies or reinforces optical energy of at least one desired wavelength within the portion of the waveguide. The device further comprises an analyte region disposed sufficiently proximal to the detection region of the substrate and a core of the waveguide, such that the analyte region is illuminated by an evanescent field emanating from the waveguide core when optical energy is passed through the waveguide. Optionally, the analyte region of the device is located within an aperture or well disposed over an exposed surface of the waveguide, e.g., such as a nanohole or a zero-mode waveguide. In certain embodiments, the analyte region is disposed within a nanometer-scale aperture that extends into the core of the waveguide. Further, the analyte region optionally comprises an analyte.

In a related aspect, the invention provides methods for illuminating an analyte comprising illuminating at least one waveguide comprising a diffraction grating pair flanking a portion of the waveguide that is proximal to a detection region of the substrate, where the diffraction grating pair intensifies or reinforces optical energy of at least one desired wavelength within the portion of the waveguide, and disposing an analyte sufficiently proximal to the detection region of the substrate and a core of the waveguide, such that the analyte is illuminated by an evanescent field emanating from the waveguide core when optical energy is passed through the waveguide. The analyte of the methods is optionally disposed within an aperture or well disposed over an exposed surface of the waveguide, e.g., such as a nanohole or a zero-mode waveguide. In certain embodiments, the analyte region is disposed within a nanometer-scale aperture that extends into the core of the waveguide.

The invention further provides analytic devices comprising a substrate comprising a first surface, at least one shallow waveguide disposed at a first depth within the substrate, at least one deep waveguide disposed at a second depth within the substrate such that the shallow waveguide is disposed between the first surface and the deep waveguide, wherein the shallow waveguide is optically coupled to the deep waveguide, and an analyte region disposed sufficiently proximal to the shallow waveguide, such that the analyte region is illuminated by an evanescent field emanating from the core of the shallow waveguide when optical energy is passed through the shallow waveguide. Optionally, the deep waveguide is shaped to enhance optical coupling between the deep waveguide and the shallow waveguide. Optionally, the analyte region of the devices is disposed within an aperture or well disposed over an exposed surface of the waveguide, e.g., such as a nanohole or a zero-mode waveguide. In certain embodiments, the analyte region is disposed within a nanometer-scale aperture that extends into the core of the waveguide. Further, the analyte region of the devices can optionally comprise an analyte.

In a related aspect, the invention provides methods for illuminating an analyte comprising illuminating a deep waveguide disposed within a substrate, coupling optical energy between the deep waveguide and a shallow waveguide disposed between a first surface of the substrate and the deep waveguide, and disposing an analyte sufficiently proximal to the shallow waveguide, such that the analyte is illuminated by an evanescent field emanating from the core of the shallow waveguide when optical energy is passed through the shallow waveguide. The analyte of the methods is optionally disposed within an aperture or well disposed over an exposed surface of the waveguide, e.g., such as a nanohole or specific type of nanohole, e.g., a zero-mode waveguide. In certain embodiments, the analyte region is disposed within a nanometer-scale aperture that extends into the core of the waveguide.

The invention provides analytic devices comprising at least one waveguide disposed upon or within a substrate, wherein the waveguide terminates at a metal island that is penetrated by at least one nanometer-scale aperture, e.g., a zero-mode waveguide. The devices can optionally comprise a plurality of waveguides terminating at a plurality of metal islands, wherein each metal island is penetrated by at least one nanometer-scale aperture. Optionally, the at least one waveguide of the devices is optically coupled to a plurality of secondary waveguides that collectively terminate at a plurality of metal islands, wherein each metal island is penetrated by at least one nanometer-scale aperture. Optionally, secondary waveguides of the devices can be optically coupled to a plurality of tertiary waveguides that collectively terminate at a plurality of metal islands, wherein each metal island is penetrated by at least one nanometer-scale aperture. The metal islands of the devices optionally comprise a metal selected from Al, Au, Ag, Ti, Pl, and Cr. Further, the metal islands that comprise at least one nanometer-scale aperture, e.g., zero-mode waveguide, can optionally comprise an analyte disposed within the aperture. The at least one nanometer-scale aperture that comprises an analyte is optionally disposed sufficiently proximal to the waveguide core, such that the analyte is illuminated by an evanescent field emanating from the waveguide core when optical energy is passed through the waveguide. In certain embodiments, the nanometer-scale aperture that extends into the core of the waveguide.

In a related aspect, the invention provides methods for illuminating an analyte comprising illuminating at least nanometer-scale aperture, e.g., one zero-mode waveguide (ZMW), disposed in a metal island by providing optical energy to the nanometer-scale aperture through an optical waveguide that terminates at a position proximal to the nanometer-scale aperture, wherein the analyte is disposed within the nanometer-scale aperture and illuminated by the optical energy emanating from a core of the optical waveguide and through the nanometer-scale aperture. Illuminating at least one nanometer-scale aperture optionally comprises coupling optical energy from an originating waveguide to a plurality of secondary waveguides, where the optical waveguide that illuminates the nanometer-scale aperture is a secondary waveguide. Illuminating a plurality of nanometer-scale apertures optionally comprises coupling optical energy from an originating waveguide to a plurality of secondary waveguides that collectively terminate in a plurality of metal islands that comprise the plurality of nanometer-scale apertures. Illuminating at least one nanometer-scale aperture optionally comprises coupling optical energy from an originating waveguide to a plurality of secondary waveguides, and coupling optical energy from the plurality of secondary waveguides to a plurality of tertiary waveguides, where the optical waveguide that illuminates the nanometer-scale aperture is a tertiary waveguide. Optionally, illuminating at least one nanometer-scale aperture comprises coupling optical energy from the plurality of secondary waveguides to a plurality of tertiary waveguides that collectively terminate in a plurality of metal islands that comprise the plurality of nanometer-scale apertures.

The invention also provides analytic devices comprising a first substrate that comprises an originating waveguide disposed upon or within the first substrate and two or more branch waveguides disposed upon or within the first substrate that are optically coupled to the originating waveguide. The devices further comprise a second substrate comprising two or more waveguides disposed upon or within the second substrate, such that the two or more waveguides of the second substrate have a first end configured to be optically coupled to the two or more branch waveguides of the first substrate. The second substrate also comprises an analyte region disposed sufficiently proximal to a core of one of the two or more waveguides of the second substrate, such that the analyte region is illuminated by an evanescent field emanating from the core when optical energy is passed through the waveguides disposed upon or within the first substrate. Optionally, the cross-sectional area at the first end of the two or more waveguides of the second substrate is greater at the optical coupling location than the cross-sectional area of the two or more waveguides of the second substrate at a detection region of the two or more waveguides of the second substrate. The devices optionally comprise a coupling element that couples optical energy between the first substrate and the second substrate. The coupling element optionally comprises at least one lens that focuses optical energy from the two or more branch waveguides of the first substrate toward the two or more waveguides of the second substrate. Optionally, the analyte region comprises an analyte. The second substrate optionally comprises at least one aperture or well disposed over an exposed surface of the waveguide, e.g., such as a nanohole or specific type of nanohole, e.g., a zero-mode waveguide, disposed proximal to at least one of the two or more waveguides within a detection region of the second substrate. In certain embodiments, the two or more branch waveguides disposed upon or within the first substrate have tapered waveguide cores. In certain embodiments, the analyte region is disposed within a nanometer-scale aperture that penetrates the first substrate in a region proximal to the core, and optionally where the nanometer-scale aperture extends into the core.

In a related aspect, the invention provides methods for illuminating an analyte comprising illuminating one or more distributing waveguides disposed upon or within a first substrate and coupling optical energy from the distributing waveguides to one or more receiving waveguides of a second substrate, such that the analyte is sufficiently proximal to a core of at least one of the receiving waveguides of the second substrate to be illuminated by an evanescent field emanating from the core. Coupling optical energy optionally comprises focusing optical energy from the distributing waveguides of the first substrate through a lens to the one or more receiving waveguides of the second substrate. In certain embodiments, the distributing waveguides have tapered waveguide cores.

Further, the invention provides analytic devices comprising at least a first optical waveguide disposed within a substrate or upon or proximal to a first surface of the substrate, a mask layer disposed over a first surface of the substrate such that the mask layer covers at least a portion of the waveguide on the first surface and not covering at least a second portion of the waveguide on the first surface, a mask cladding layer disposed over the mask layer, and an analyte region disposed sufficiently proximal to a core of the first optical waveguide to be illuminated by an evanescent field emanating from the core when optical energy is passed through the first optical waveguide. The mask layer optionally comprises a plurality of apertures that provide access to at least a portion of the waveguide on the first surface. Optionally, the spacing between the apertures exhibits a random spacing error, e.g., a random spacing error of about 5%. The mask cladding layer is optionally disposed over the mask layer at locations where the mask layer is disposed over the waveguide and not disposed over the mask layer at locations where the mask layer is not disposed over the waveguide. The mask cladding layer optionally comprises a light reflective material, e.g., a metal (e.g., aluminum). Optionally, the mask cladding layer comprises a light absorptive material, e.g., Cr. The analyte region optionally is disposed within a nanometer-scale aperture or well disposed over an exposed surface of the waveguide, e.g., such as a nanohole (e.g., a zero-mode waveguide). Optionally, the analyte region is disposed within a nanometer-scale aperture that extends into the first optical waveguide. Optionally, the analyte region comprises an analyte.

In a related aspect, the invention provides methods for illuminating an analyte disposed in an analyte region comprising distributing optical energy to the analyte region through an optical waveguide, such that the efficiency of optical energy delivery through the waveguide is enhanced by at least partially covering at least one surface of the waveguide with an at least partially light reflective or light absorptive material bilayer.

The invention also provides analytic devices comprising a substrate comprising a first surface, at least one optical waveguide disposed upon or within the first surface, an array of substantially parallel lines of a surface immobilization compound such that the substantially parallel line of the surface immobilization compound are substantially perpendicular with respect to the at least one optical waveguide, and an analyte attached to the surface immobilization compound where the surface immobilization compound and the waveguide intersect, such that the analyte is disposed sufficiently proximal to a core of the optical waveguide to be illuminated by an evanescent field emanating from the core when optical energy is passed through the optical waveguide. Optionally, the substrate comprises an array of optical waveguides. The surface immobilization compound optionally comprises a metal, e.g., Au.

In a related aspect, the invention provides methods for immobilizing an analyte on an analytic device, comprising depositing an array of substantially parallel lines of a surface immobilization compound on a substrate of the analytic device, such that the substantially parallel lines of the surface immobilization compound are deposited in a substantially perpendicular orientation with respect to at least one optical waveguide disposed upon or within the substrate. The methods further comprise attaching an analyte to the surface immobilization compound where the surface immobilization compound and the waveguide intersect. Optionally, the surface immobilization compound comprises a metal, e.g., Au. The substrate optionally comprises an array of optical waveguides.

The invention also provides analytic devices comprising a substrate comprising a detection region and at least one optical waveguide that traverses the detection region, wherein the at least one optical waveguide has a first end coupled to an optical energy source and a second end that is not coupled to the optical energy source, and further wherein the optical waveguide is configured to have a higher confinement of optical energy at the second end than at the first end. The device further comprises a plurality of analyte regions disposed on a surface of the substrate in the detection region and sufficiently proximal to a core of the optical waveguide to be illuminated by an evanescent field emanating from the core when optical energy is passed through the optical waveguide. In certain embodiments, the core of the optical waveguide is tapered such that there is a gradual decrease in thickness from the first end to the second end. In certain embodiments, a waveguide cladding of the optical waveguide is tapered such that the core becomes gradually closer to the analyte regions from the first end to the second end. In certain embodiments, the core has a first refractive index at the first end and a second refractive index at the second end, and further wherein the core is configured that there is a gradual increase in refractive index from the first end to the second end. In yet further embodiments, a waveguide cladding of the optical waveguide has a first refractive index at the first end and a second refractive index at the second end, and further wherein the core is configured that there is a gradual decrease in refractive index from the first end to the second end.

The invention also provides analytic devices comprising substrates with at least one optical waveguide, wherein the at least one optical waveguide is configured to propagate optical energy of a plurality of wavelengths with comparable electric field intensities. The devices also comprise a plurality of analyte regions disposed on a surface of the substrate sufficiently proximal to a core of the optical waveguide to be illuminated by an evanescent field emanating from the core when optical energy is passed through the optical waveguide. In certain embodiments, the plurality of wavelengths are in the visible spectrum. In certain embodiments, the optical waveguide utilizes different polarizations for each of the plurality of wavelengths, and, optionally, a first of the polarizations utilizes a TE polarized mode, and a second of the polarizations utilizes a TM polarized mode.

The invention also provides methods for providing uniform illumination to a plurality of analyte regions on a substrate. For example, in some embodiments a waveguide core disposed within a substrate is configured to gradually increase a measure of optical confinement of the waveguide core along the direction of propagation of optical energy within the core, e.g., in order to maintain a desired mode shape and or a desired field strength. A plurality of analyte regions are disposed along a portion of the substrate proximal to the waveguide core and optical energy is coupled into the waveguide core, thereby providing uniform illumination to the plurality of analyte regions. In certain preferred embodiments, the waveguide core is tapered so that it becomes thinner along the direction of propagation of the optical energy in the core. Additionally or alternatively, the refractive index of the waveguide core is gradually increased in the direction of propagation of the excitation illumination. Additionally or alternatively, the waveguide core has different polarizations for different wavelengths of excitation illumination.

The invention also provides an analytical device comprising a substrate, a detection region thereon, and at least one optical waveguide that is disposed proximal to the detection region, wherein the detection region comprises a plurality of nanoholes within which analyte regions are disposed, and a plurality of dummy nanoholes that do not comprise analyte regions.

The invention also provides an analytical device that includes a substrate comprising at least one optical waveguide and at least one nanometer-scale aperture that penetrates into a first side of the substrate and extends toward a core of the optical waveguide such that an analyte disposed therein is sufficiently proximal to the core to be illuminated by an evanescent field emanating from the core when optical energy is passed through the optical waveguide. Optionally, the device further comprises a detector disposed proximal to the substrate on a side opposite the first side, and a reflective coating over the first side of the substrate that reflects signal emissions from the nanometer-scale aperture. The reflection of signal emissions by the reflective coating mitigates their passage through the first surface of the substrate and reflects them toward the detector. In certain embodiments, the reflective coating comprises aluminum. In certain embodiments, the nanometer-scale aperture penetrates a waveguide cladding and/or core of the optical waveguide. Optionally, the devices further comprise a first objective lens positioned proximal to the first side of the substrate, and a second objective lens positioned proximal to the substrate on a side opposite the first side. In certain embodiments, the substrate has a detection region that comprises the nanometer-scale aperture, and further wherein both the first and second objective lenses collect signal from the same portion or all of the detection region. In certain embodiments, the substrate has a detection region that comprises the nanometer-scale aperture, and further wherein the first objective lens collects signal from a first portion (e.g., a first half) of the detection region and the second objective lens collects signal from a second portion (e.g., a second half) of the detection region. Optionally, the first and/or second objective lenses are water immersion lenses. In certain embodiments, the devices further comprise at least one detector operably linked to the first and the second objective lenses. Optionally, a first detector can be operably linked to the first objective lens and a second detector can be operably linked to the second objective lens; at least one of the first and second detectors can be a camera.

The invention also provides an analytical device that includes a substrate comprising at least one optical waveguide having a core of a high refractive index material, a mask layer disposed over a first surface of the substrate, a thin layer disposed between the first surface of the substrate and the mask layer, wherein the thin layer is silane chemistry compatible, and one or more nanometer-scale apertures (e.g., zero-mode waveguides) disposed through the mask layer but not through the thin layer or into the substrate, wherein analyte regions within the apertures are sufficiently proximal to the core to be illuminated by an evanescent field emanating from the core when optical energy is passed through the optical waveguide. Optionally, the mask layer can comprise $Al_2O_3$ or a low refractive index material that is coated with $Al_2O_3$.

The invention also provides an analytic device comprising a single substrate that includes a coupling region in which optical energy is coupled into an originating waveguide disposed upon or within the substrate; a splitter region in which the originating waveguide is split into two or more branch waveguides disposed upon or within the substrate, wherein the branch waveguides are optically coupled to the originating waveguide and therefore propagate the optical energy in the originating waveguide; a bend region wherein the two or more branch waveguides comprise a bend that changes a direction of propagation of the optical energy within the branch waveguides; and a detection region wherein at least one analyte region is disposed sufficiently proximal to at least one core of the branch waveguides to be illuminated by an evanescent field emanating from the core when optical energy is passed through the branch waveguides disposed upon or within the first substrate. Optionally, the analytic device has a bend with an angle from 45 to 135 degrees, preferably between about 75-105 degrees, and in certain embodiments 90 degrees. In certain embodiments, the analyte region is disposed within a nanometer-scale aperture. In certain embodiments, the nanometer-scale aperture extends into a cladding layer proximal to the core, or extends all the way into the core. In certain embodiments, the nanometer-scale aperture is a zero-mode waveguide. In preferred embodiments, the splitter region comprises one or more Y-branch splitters and/or extends between about 10 mm and 50 mm. Optionally, the detection region of the device comprises a plurality of optically resolvable analyte regions, e.g., at least about 1000, or at least about 10,000, or at least about 50,000 optically resolvable analyte regions. In specific embodiments, a portion of one of the branch waveguides that passes through the detection region is less than 3-5 mm in length.

The invention also provides an integrated optical device that comprises a plurality of components, including a) a first component comprising a waveguide disposed upon or within a substrate, and further comprising a biosensing region wherein a plurality of nanometer-scale apertures comprise analyte regions disposed sufficiently proximal to a core of the waveguide to be illuminated by an evanescent field emanating from the core when optical energy is passed through the waveguide; b) a second component comprising a microlens array that collects optical energy signals from the biosensing region and directs the optical energy signals so collected to a detector; and c) a third component comprising the detector. The first component optionally comprises a plurality of channel waveguides. The nanometer-scale apertures are optionally zero-mode waveguides. In certain embodiments, the nanometer-scale apertures extend into a cladding layer and/or the core of the waveguide. In certain embodiments, optical energy of at least two detectably-different wavelengths is propagated within the waveguide. Optionally, each waveguide can use a different polarization mode to propagate each of the detectably-different wavelengths of optical energy. The second component optionally comprises a notch filter and/or a dispersive grating. In certain embodiments, the device further comprises an immersion fluid layer between the first and second components. The third component optionally comprises a multi-sensor array and/or individual pixels that collect optical energy signals from a single one of the nanometer-scale apertures.

The invention also provides a device comprising a substrate comprising one or more reaction sites, a mask layer on a first surface of the substrate, a multilayer dielectric stack, e.g., a dielectric omnidirectional reflector, on a second surface of the substrate, and an optical energy source that directs optical energy into the substrate.

DETAILED DESCRIPTION

Figure 1:
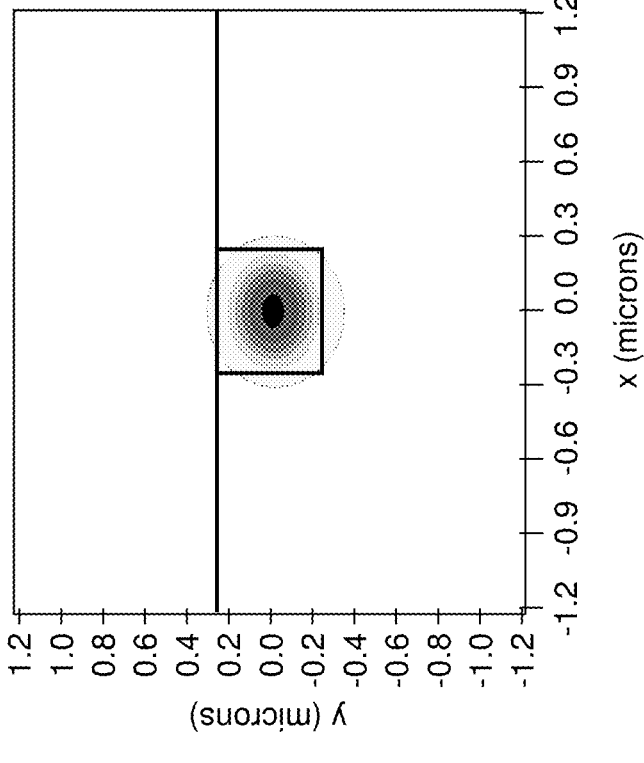
FIG. 1A provides an electric field distribution simulation for one embodiment of a surface-exposed waveguide, and FIG. 1B provides a schematic representation of the electric field distribution simulation.
Figure 1:
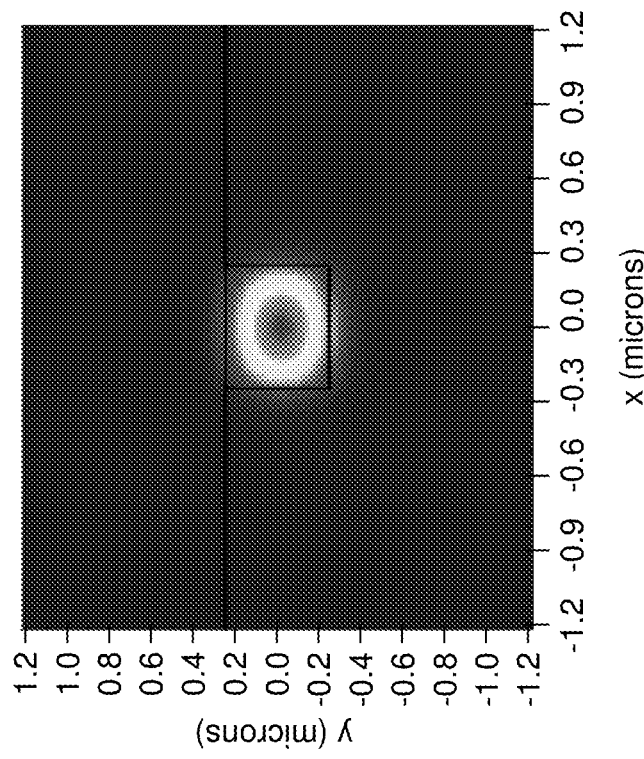

The present invention is broadly applicable to any application in which one desires to illuminate materials (e.g., analytes) that are at or proximal to a surface and/or specific locations on a surface, without illuminating materials that are not similarly situated. For example, such systems are particularly useful in the analysis of individual molecules or molecular interactions and/or interactions of surface-coupled reactants, such as, e.g., polynucleotide or polypeptide polymerization reactions, hybridization reactions, binding assays, and the like. Further details regarding such single-molecule/molecular complex analyses are provided, e.g., in U.S. patent application Ser. No. 12/413,258 (filed Mar. 27, 2009), Ser. No. 12/328,715 (filed Dec. 4, 2009), Ser. No. 12/413,226 (filed Mar. 27, 2009), and 61/186,661 (filed Jun. 12, 2009); U.S. Patent Publication No. 20070206187; and U.S. Pat. Nos. 7,056,661 and 6,917,726, all of which are incorporated herein by reference in their entireties for all purposes.

In certain embodiments, the present invention provides substrates comprising one or more waveguides. The methods include waveguide-mediated illumination of an analytical reaction or analyte of interest using, e.g., surface-exposed, substrate-enclosed, or core-exposed waveguides, such that the exponential decay of light outside the waveguide core (e.g., an evanescent field) may be exploited on a surface region of the substrate to illuminate materials provided upon that surface. By providing materials at or proximal to the surface, e.g., at a reaction site, one can controllably illuminate such materials without illuminating any materials outside of the evanescent field. In certain embodiments, the present invention provides devices comprising multilayer dielectric stacks, e.g. dielectric omnidirectional reflectors, configured to propagate optical energy to one or more reaction sites on a substrate.

A number of analytical operations can benefit from the ability to controllably illuminate materials at or near a surface and/or at a number of locations thereon, without excessively illuminating the surrounding environment. Examples of such analyses include illumination, observation and/or analysis of surface-bound cells, proteins, nucleic acids, or other molecules of interest. Such illumination is particularly useful in illuminating fluorescent and/or fluorogenic materials upon or proximal to the surface, including nucleic acid array-based methods, substrate-coupled nucleic acid and polypeptide sequencing-by-synthesis methods, antibody/antigen interactions, binding assays, and a variety of other applications. The methods, devices, compositions, and systems provided herein are particularly suitable for single-molecule-level detection of analytical reactions in real-time, e.g., during the ongoing analytical reaction. For example, a single polymerase enzyme can be immobilized on a substrate and monitored as it incorporates differentially labeled nucleotides into a nascent nucleic acid strand by illuminating the substrate surface where the polymerase is bound and detecting a sequence of fluorescent emissions from the reaction site that corresponds to the sequence of nucleotides incorporated by the polymerase.

In the context of analysis, the substrates and methods of the invention are advantageous for numerous reasons. For example, because the illumination light is applied in a spatially focused manner, e.g., confined in at least one lateral and one orthogonal dimension, using efficient optical systems, e.g., fiber optics, waveguides, multilayer dielectric stacks (e.g., dielectric reflectors), etc., the invention provides an efficient use of illumination (e.g., laser) power. For example, illumination of a substrate comprising many separate reaction sites, "detection regions," or "observation regions" using waveguide arrays as described herein can reduce the illumination power ~10- to 1000-fold as compared to illumination of the same substrate using a free space illumination scheme comprising, for example, separate illumination (e.g., via laser beams) of each reaction site. In general, the higher the multiplex (i.e., the more surface regions to be illuminated on the substrate), the greater the potential energy savings offered by the waveguide and dielectric stack-based illumination schemes provided herein. In addition, since waveguide illumination need not pass through a free space optical train prior to reaching the surface region to be illuminated (as described further below), the illumination power can be further reduced.

In addition, because illumination is provided from within confined regions of the substrate itself (e.g., optical waveguides), issues of illumination of background or non-relevant regions, e.g., illumination of non-relevant materials in solutions, autofluorescence of substrates, and/or other materials, reflection of illumination radiation, etc. are substantially reduced. Likewise, this aspect of the invention provides an ability to perform many homogenous assays for which it would be generally applicable.

In addition to mitigating autofluorescence of the substrate materials, the systems described herein substantially mitigate autofluorescence associated with the optical train. In particular, in typical fluorescence spectroscopy, excitation light is directed at a reaction of interest through at least a portion of the same optical train used to collect signal fluorescence, e.g., the objective and other optical train components. As such, autofluorescence of such components will contribute to the detected fluorescence level and can provide signal noise in the overall detection. Because the systems provided herein direct excitation light into the substrate through a different path, e.g., through an optical fiber optically coupled to the waveguide in the substrate, or by internal reflection between a mask layer and a dielectric reflector, this source of autofluorescence is eliminated.

Waveguide-mediated and dielectric-based illumination is also advantageous with respect to alignment of illumination light with surface regions to be illuminated. In particular, substrate-based analytical systems, and particularly those that rely upon fluorescent or fluorogenic signals for the monitoring of reactions, typically employ illumination schemes whereby each analyte region must be illuminated by optical energy of an appropriate wavelength, e.g., excitation illumination. While bathing or flooding the substrate with excitation illumination serves to illuminate large numbers of discrete regions, such illumination suffers from the myriad complications described above. To address those issues, some embodiments of the invention provide targeted excitation illumination to selectively direct separate beams of excitation illumination to individual reaction regions or groups of reaction regions, e.g. using waveguide arrays. When a plurality, e.g., hundreds or thousands, of analyte regions are disposed upon a substrate, alignment of a separate illumination beam with each analyte region becomes technically more challenging and the risk of misalignment of the beams and analyte regions increases. In the present invention, alignment of the illumination sources and analyte regions is built into the system, because the illumination pattern and reaction regions are integrated into the same component of the system, e.g., a waveguide substrate. In certain preferred embodiments, optical waveguides are fabricated into a substrate at defined regions of the substrate, and analyte regions are disposed upon the area(s) of the substrate occupied by the waveguides.

Finally, the substrates of the invention typically are provided from rugged materials, e.g., silicon, glass, quartz or polymeric or inorganic materials that have demonstrated longevity in harsh environments, e.g., extremes of cold, heat, chemical compositions, e.g., high salt, acidic or basic environments, vacuum and zero gravity. As such, they provide rugged capabilities for a wide range of applications.

Exemplary waveguide array configurations, methods of fabricating the waveguide arrays of the invention, waveguide arrays with additional functionalities, devices comprising multilayer dielectric stacks (e.g., dielectric reflectors), and methods and applications provided by the present invention are described in detail below.

I. Waveguide Substrates

Waveguide substrates of the present invention generally include a matrix, e.g., a silica-based matrix, such as silicon, glass, quartz or the like, polymeric matrix, ceramic matrix, or other solid organic or inorganic material conventionally employed in the fabrication of waveguide substrates, and one or more waveguides disposed upon or within the matrix, where the waveguides are configured to be optically coupled to an optical energy source, e.g., a laser. Such waveguides may be in various conformations, including but not limited to planar waveguides and channel waveguides. Some preferred embodiments of waveguide substrates comprise an array of two or more waveguides, e.g., discrete channel waveguides, and such waveguide substrates are also referred to herein as waveguide arrays. Further, channel waveguides can have different cross-sectional dimensions and shapes, e.g., rectangular, circular, oval, lobed, and the like; and in certain embodiments, different conformations of waveguides, e.g., channel and/or planar, can be present in a single waveguide substrate.

In typical embodiments, a waveguide comprises a waveguide core and a waveguide cladding adjacent to the waveguide core, where the waveguide core has a refractive index sufficiently higher than the refractive index of the waveguide cladding to promote containment and propagation of optical energy through the core. In general, the waveguide cladding refers to a portion of the substrate that is adjacent to and partially, substantially, or completely surrounds the waveguide core, as further described below. The waveguide cladding layer can extend throughout the matrix, or the matrix may comprise further "non-cladding" layers. A "substrate-enclosed" waveguide or region thereof is entirely surrounded by a non-cladding layer of matrix; a "surface-exposed" waveguide or region thereof has at least a portion of the waveguide cladding exposed on a surface of the substrate; and a "core-exposed" waveguide or region thereof has at least a portion of the core exposed on a surface of the substrate. Further, a waveguide array can comprise discrete waveguides in various conformations, including but not limited to, parallel, perpendicular, convergent, divergent, entirely separate, branched, end-joined, serpentine, and combinations thereof.

A surface or surface region of a waveguide substrate is generally a portion of the substrate in contact with the space surrounding the substrate, and such space may be fluid-filled, e.g., an analytical reaction mixture containing various reaction components. In certain preferred embodiments, substrate surfaces are provided in apertures that descend into the substrate, and optionally into the waveguide cladding and/or the waveguide core. In certain preferred embodiments, such apertures are very small, e.g., having dimensions on the micrometer or nanometer scale, and are further described below.

It is an object of the invention to illuminate analytes (e.g., reaction components) of interest and to detect signal emitted from such analytes, e.g., by excitation and emission from a fluorescent label on the analyte. Of particular interest is the ability to monitor single analytical reactions in real time during the course of the reaction, e.g., a single enzyme or enzyme complex catalyzing a reaction of interest. The waveguides provided herein provide illumination via an evanescent field produced by the escape of optical energy from the waveguide core. The evanescent field is the optical energy field that decays exponentially as a function of distance from the waveguide surface when optical energy passes through the waveguide. As such, in order for an analyte of interest to be illuminated by the waveguide it must be disposed near enough the waveguide core to be exposed to the evanescent field. In preferred embodiments, such analytes are immobilized, directly or indirectly, on a surface of the waveguide substrate. For example, immobilization can take place on a surface-exposed waveguide, or within an aperture in the substrate. In some preferred aspects, analyte regions are disposed in apertures that extend through the substrate to bring the analyte regions closer to the waveguide core. Such apertures may extend through a waveguide cladding surrounding the waveguide core, or may extend into the core of the waveguide. In certain embodiments, such apertures also extend through a mask layer above the surface of the substrate. In preferred embodiments, such apertures are "nanoholes," which are nanometer-scale holes or wells that provide structural confinement of analytic materials of interest within a nanometer-scale diameter, e.g., ~10-100 nm. In some embodiments, such apertures comprise optical confinement characteristics, such as zero-mode waveguides, which are also nanometer-scale apertures and are further described elsewhere herein. Although primarily described herein in terms of channel waveguides, such apertures could also be constructed on a planar waveguide substrate, e.g., where the planar waveguide portion/layer is buried within the substrate, i.e., is not surface-exposed. Regions on the surface of a waveguide substrate that are used for illumination of analytes are generally termed "analyte regions," "reaction regions," or "reaction sites," and are preferably located on a surface of the substrate near enough to a waveguide core to be illuminated by an evanescent wave emanating from the waveguide core, e.g., on a surface-exposed waveguide or at the bottom of an aperture that extends into the substrate, e.g., into the waveguide cladding or core. The three-dimensional area at a reaction site that is illuminated by the evanescent field of a waveguide core (e.g., to an extent capable of allowing detection of an analyte of interest) is generally termed the "observation volume" or "illumination volume." A region of a waveguide substrate that comprises one or more analyte regions is generally referred to as a "detection region" of the substrate, and a single substrate may have one or multiple detection regions.

An electric field distribution simulation for a surface-exposed waveguide is shown in FIG. 1A; the simulation data was generated in color, but is shown here in grayscale, which does not allow distinction of various aspects of the distribution. As such, a schematic representation of the electric field distribution simulation is shown in FIG. 1B to show the general pattern of the changing electric field in and around the waveguide core. Specifically, highest intensity portion of the field is black, with the color lightening as the field intensity decreases. In such a surface-exposed waveguide, peak electric intensity generally lies along the center of the waveguide core. On the exposed surface of the core, the electric field intensity is roughly 20% of the intensity at the center of the core, and this field intensity decays exponentially into the space above the exposed surface of the core, e.g., into a fluid volume, thereby providing excitation confinement in the vertical direction. In the horizontal direction, however, the confinement is weak. That is, a relatively large area on the surface of the waveguide experiences a relatively strong field intensity. As such, the relatively large observation volume generated by the evanescent field from the surface exposed waveguide core may be greater than a preferred observation volume, e.g., for single molecule detection. For example, even in an embodiment in which a confocal pinhole is used on the surface of the waveguide, the observation volume is still approximately 500-fold larger than the observation volume of a typical zero-mode waveguide. As such, higher background signal is expected under conditions in which concentrations of detectable reaction components, e.g. fluorescent-labeled reactants, are high enough that more than one is expected to reside in a single such observation volume at a given time.

Figure 2:
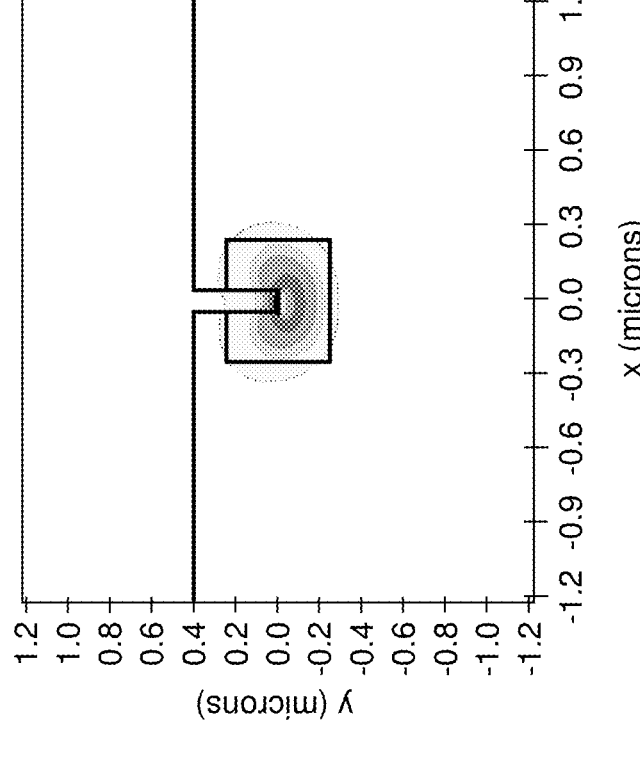
FIG. 2 provides an electric field distribution simulation for one embodiment of a core-exposed waveguide, and FIG. 2B provides a schematic representation of the electric field distribution simulation.
Figure 2:
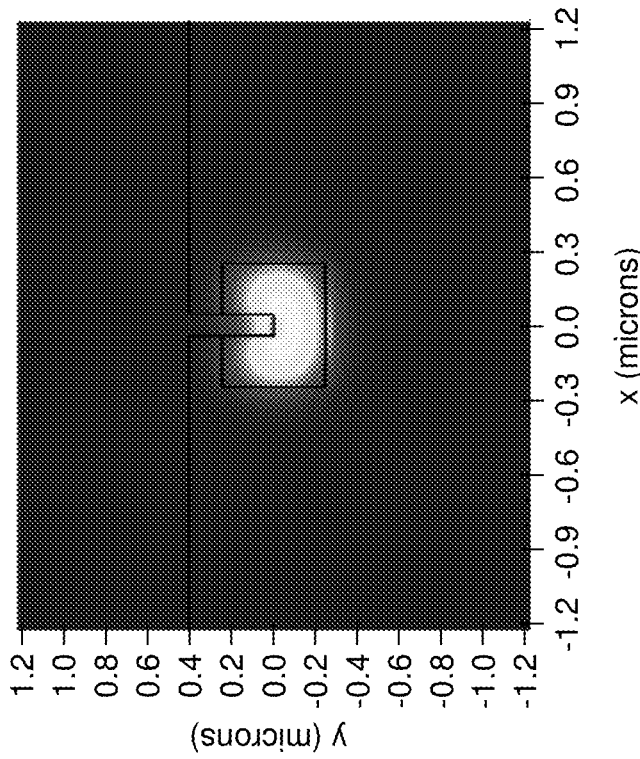
Figure 3:
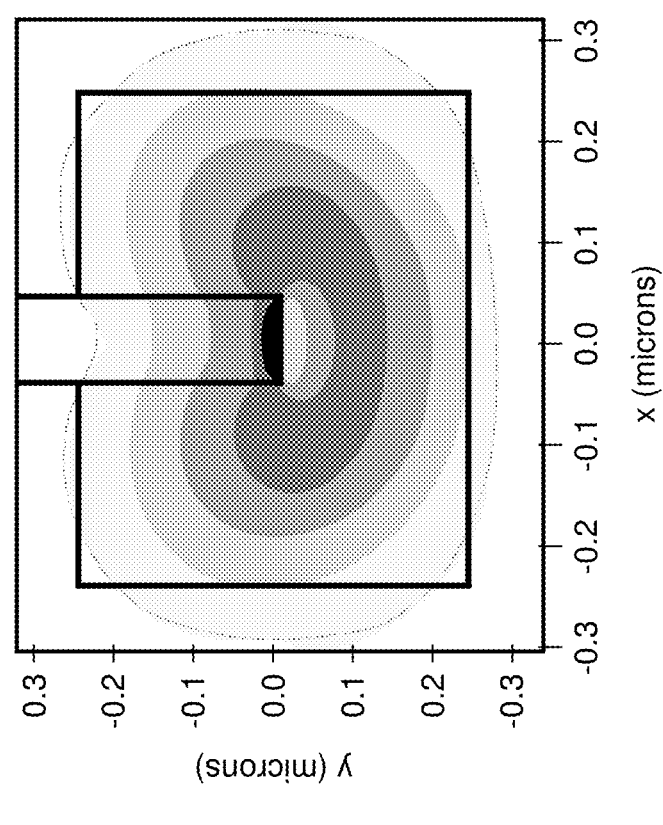
FIG. 3 provides an electric field distribution simulation for an embodiment of a core-exposed waveguide for which the shape and/or refractive index of the waveguide core and substrate has been optimized to concentrate the peak intensity of the electric field at the center of a nanohol, and FIG. 3B provides a schematic representation of the electric field distribution simulation.
Figure 3:
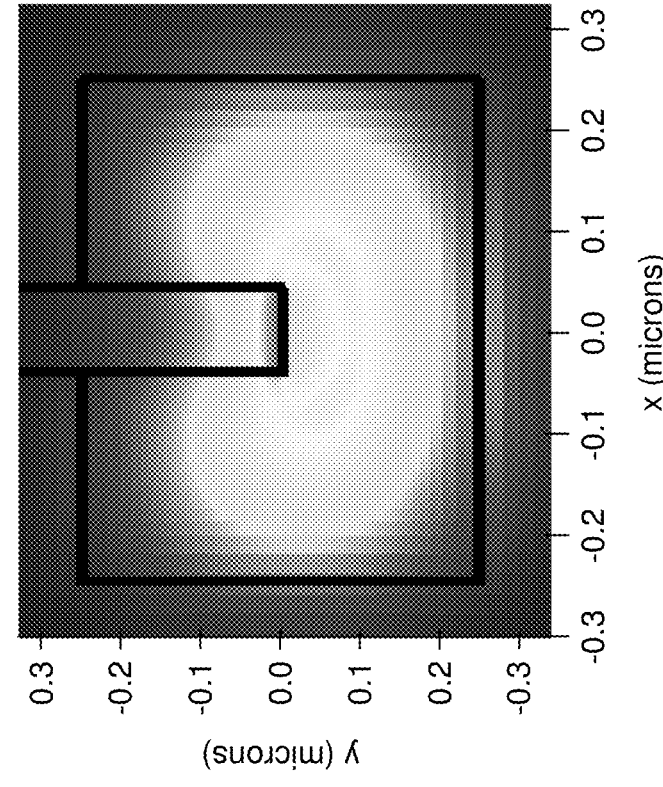

FIG. 2A provides an illustrative example of an electric field distribution simulation for one example of a core-exposed waveguide comprising a waveguide core into which a nanohole has been disposed. As for FIG. 1A, the simulation data was generated in color, but is shown here in grayscale, which does not allow distinction of various aspects of the distribution. As such, a schematic representation of the electric field distribution simulation is shown in FIG. 2B to show the general pattern of the changing electric field in and around the waveguide core. Specifically, highest intensity portion of the field is black, with the color lightening as the field intensity decreases. Such a structure physically limits the volume of a solution or reaction mixture exposed to the electric field of the waveguide core, thereby limiting the observation volume within which excitation of and emission from various reaction components can occur. Therefore, for a given concentration of labeled reactant in a reaction mixture, fewer individual labeled reactants would exist in the observation volume of a nanohole than would be expected to exist in the observation volume on a surface-exposed waveguide core, e.g., because the observation volume of the former is much smaller than the observation volume of the latter. Take, for example, a waveguide core of 0.5 $\mu m^2$ that lies 150 nm below the surface of the substrate and comprises a nanohole with an 80 nm diameter that extends from the surface of the substrate to the center of the waveguide core. A simulated electric field based on a 633 nm wavelength of excitation light and water as the fluid in the nanohole produces the electric field distribution shown in FIG. 2A. The presence of the nanohole in the core of the waveguide changes the electric field distribution, and focuses the highest intensity of excitation radiation at the base of the nanohole in the center of the waveguide. Further, modification of the shape and/or refractive index of the waveguide core and substrate can alter the electric field to further concentrate the peak intensity at the center of the nanohole, as shown in FIG. 3A and the schematic representation depicting the general pattern of the changing electric field provided in FIG. 3B, in which the most intense portion of the electric field distribution is better centered in the bottom of the nanohole than the electric field distribution provided in FIGS. 2A and 2B. In general, the faster the intensity decays from the bottom of the nanohole, the better the illumination confinement within the nanohole. Although the nanohole itself does not provide confinement of the excitation radiation, the effective detection region is confined in the nanometer range because labeled reactants can only get into the observation volume via the nanohole. Thus, the observation volume of a nanohole extending into the core of a waveguide can be comparable to that of a zero-mode waveguide, e.g., at the attoliter ($10^{-18}$ L) to zeptoliter ($10^{-21}$ L) scale, a volume suitable for detection and analysis of single molecules and single molecular complexes.

In certain preferred embodiments, a mask layer is disposed upon the waveguide substrate, and analyte regions are disposed through the mask layer such that materials within the analyte regions can be sufficiently proximal to the waveguide core to permit their illumination by an evanescent field emanating from the waveguide core during operation of the array. The analyte regions are generally disposed through the mask layer within an area of the mask layer that demarks a detection region of the waveguide substrate. When a waveguide substrate is employed as part of a larger analytical system, e.g., a system for detecting fluorescent materials that are proximal to the waveguide surface, a detection system can be disposed proximal to the detection region of the array such that signals derived from illuminated materials within the analyte regions can be detected and subsequently analyzed.

The present invention provides waveguide substrates with improved optical and/or structural functionalities that provide improved illumination energy distribution across arrays of reaction regions, improved illumination of individual reaction regions, and a number of other improved properties. For example, in certain aspects, the present invention provides waveguides of different depths for enhanced optical energy distribution and illumination of analyte regions. Also provided are waveguide arrays that include grating couplers for normalizing optical energy intensity among arrayed waveguides and/or grating pairs disposed upon the surface of arrayed waveguides for enhanced illumination efficiency within a detection region of the array. Further, the present invention provides waveguide substrates with a top mask cladding layer disposed upon a mask layer for reduced scattering of light resulting from nanoholes situated proximal to the waveguides, as well as non-uniform spacing of such nanoholes for reduced back reflection of light into the waveguides. The present invention further provides waveguide substrates with lines of surface immobilization compounds deposited upon the surface of the substrate for improved immobilization of analytes upon or proximal to one or more waveguide cores. The present invention further provides waveguide substrates with waveguides having a tapered structure and/or a gradation of refractive index that is gradually modified in the direction of optical energy propagation to in order to smoothly adjust the degree of confinement and relative field strength, as further described below.

Example Waveguide Configuration

An object of the instant invention is to provide confinement of illumination from a waveguide core to analyte regions disposed on a surface of a waveguide substrate. In certain preferred embodiments, such confinement is facilitated by a high refractive index contrast between the waveguide core and the waveguide cladding around the waveguide core. In certain preferred embodiments, a waveguide cladding surrounding a waveguide core has a significantly lower refractive index than the waveguide core, and serves to confine the modal profile (or diameter) of the guided optical wave(s) into the submicrometer (or only a few micrometer) range. That is, the optical waves extend only a submicrometer to few micrometer distance outside the core. At a detection region of the substrate, nanosize features (e.g., nanoholes or zero-mode waveguides) provide illumination confinement to excite single analytes for detection, e.g., by fluorescence emission. In certain preferred embodiments, the optical waves are in the visible range. In certain preferred embodiments, multiple wavelengths of optical waves are propagated and detected simultaneously, e.g., in real time during the course of an analytical reaction of interest.

Figure 4A:
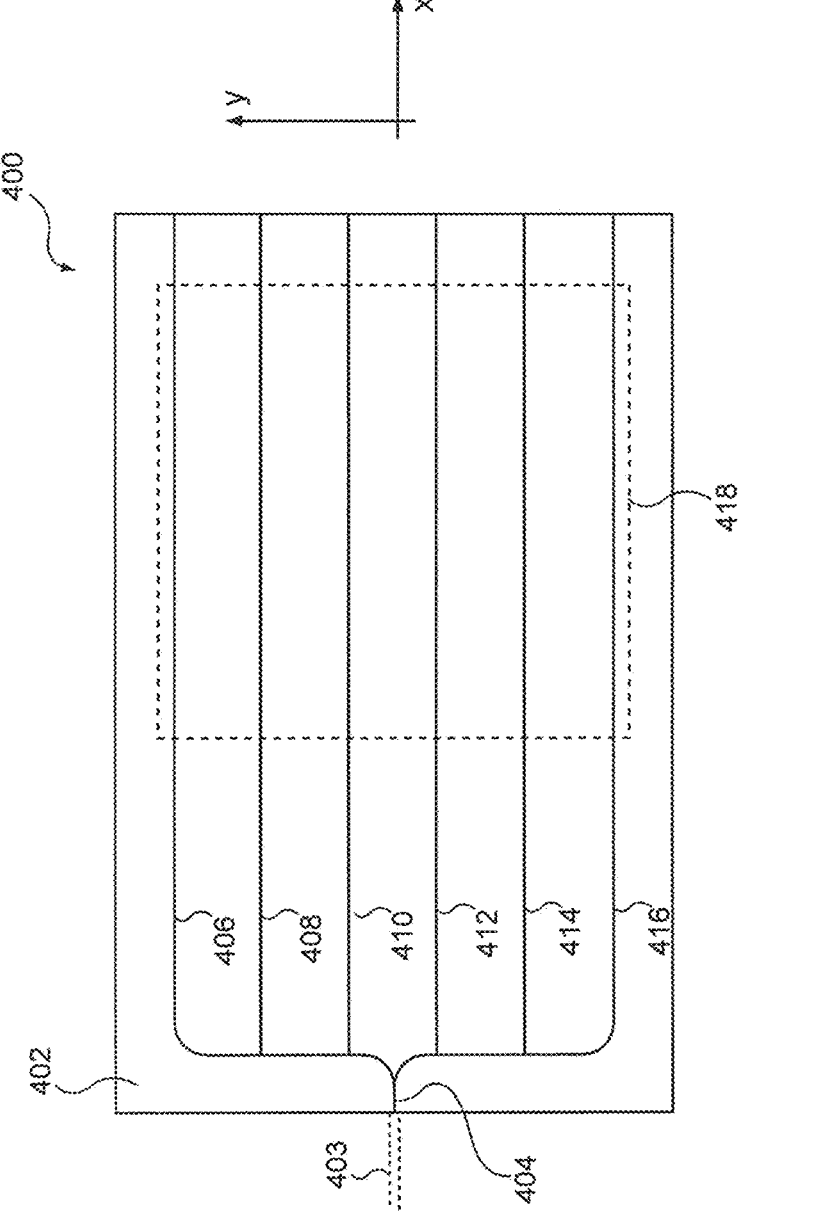
FIGS. 4A, 4B, and 4C provide schematic illustrations of alternate examples of the devices of the invention.

An example analytic device that employs arrayed waveguides to illuminate a plurality of analyte regions, e.g., optically confined regions in which materials of interest are controllably illuminated in the manner described above, is schematically illustrated in FIGS. 4A-C. FIG. 4A schematically illustrates a top view of example device 400 that includes a matrix 402. Waveguides 406-416 are provided to confine and propagate light introduced into them, For the purposes of the present disclosure, a waveguide refers to a waveguide core and can further include a waveguide cladding layer partially or substantially surrounding the core. These exemplary arrayed waveguides receive light from an excitation illumination source, e.g., via a first optical fiber 403, that is optically coupled to the waveguides, e.g., connected such that light is transmitted from one to the other, propagated (via waveguide 404), and optionally divided among branch waveguides 406-416. It will be appreciated that the number of arrayed waveguides of the device can range from one waveguide to a plurality of waveguides, e.g., 10 or more, 20 or more, 30 or more, 40 or more, 100 or more, or 1000 or more waveguides are possible. A mask layer (see, e.g., 420 in FIG. 4B) is provided, such that analyte regions, e.g., apertures disposed through the mask layer (See, e.g., 422 in FIG. 4B), can be disposed over and provide access to a portion of the surface of waveguides 406-416 at discrete locations within detection region 418 of device 400. While the substrates of the invention are preferably planar substrates having the waveguide(s) disposed therein, it will be appreciated that for certain applications, non-planar substrates may be employed, including, for example, fiber based substrates, shaped substrates, and the like. Although example device 400 is shown with a single input waveguide 404, it will be appreciated that waveguide substrates of the invention may comprise multiple input waveguides, and that these multiple input waveguides can be divided into branch waveguides that illuminate one or more detection regions. For example, in certain embodiments a single detection region is illuminated with optical energy originating from multiple input waveguides, each of which is optionally split into a plurality of branch waveguides prior to passage through the detection region. Such multiple input waveguides may be coupled to one or more optical energy sources along a single edge of a waveguide substrate, or may be coupled on different sides, e.g. opposite sides, of the waveguide substrate. The one or more optical energy sources may provide the same or different optical energy to the multiple input waveguides, e.g., same or different wavelengths, intensities, etc.

Figure 4B:
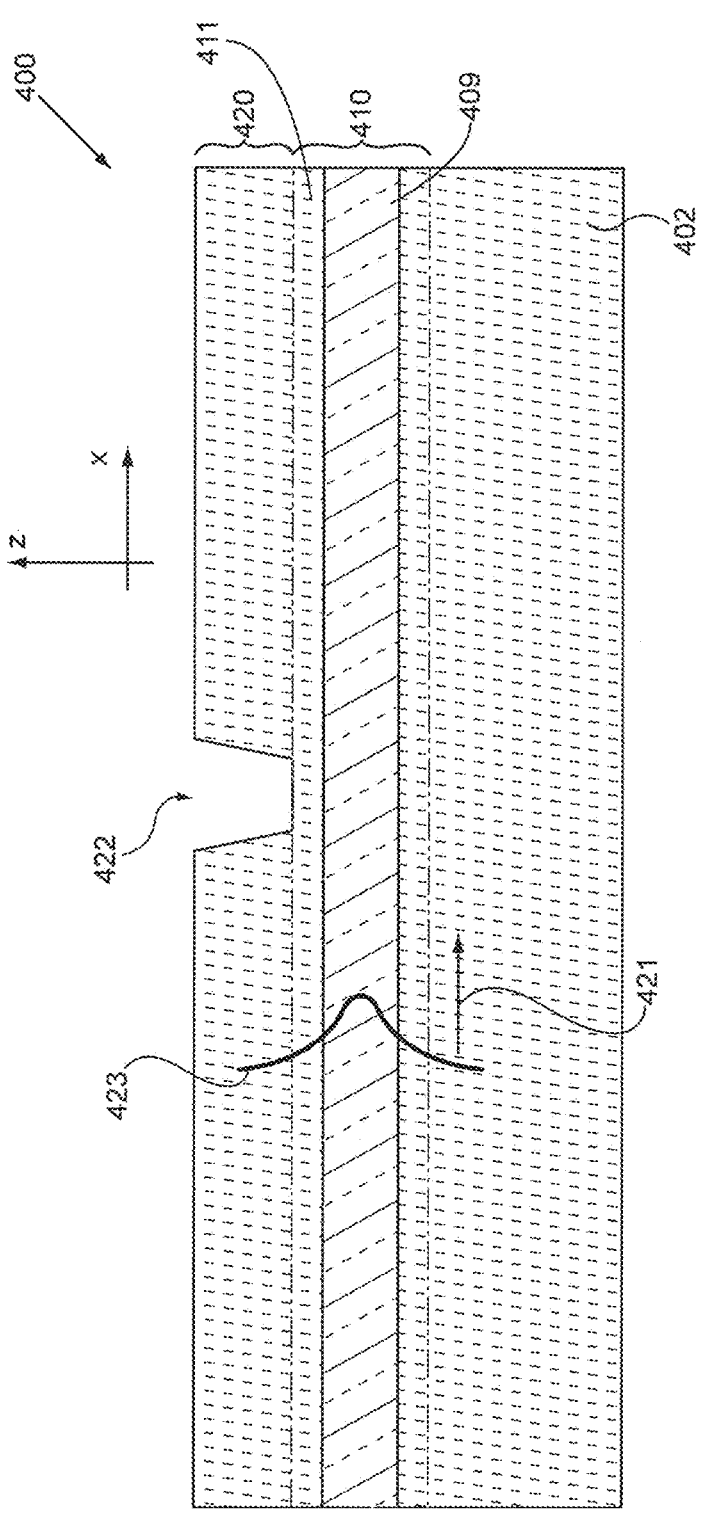

A cross section through the detection region of example device 400, where the section runs lengthwise and through an arrayed waveguide, e.g., waveguide 410, is schematically illustrated in FIG. 4B. As shown, mask layer 420 is disposed on top of waveguide 410, which includes waveguide core 409 and waveguide cladding 411. Analyte regions are provided as apertures through the mask layer that provide access to the underlying surface-exposed waveguide. For example, as shown, nanohole 422, is disposed through mask layer 420, thereby providing access to the surface of waveguide 410, and in particular to the surface of the waveguide cladding. Nanoholes, e.g., nanometer-sized apertures or wells disposed through mask layer 420, are preferable as compared to larger apertures, e.g., microholes, milliholes, centiholes, etc., because nanoholes are of such small cross sectional dimensions, e.g., 50-200 nm in cross section, that they provide a sufficiently small volume of structural confinement such that issues of illumination of background or non-relevant regions, e.g., illumination of non-relevant materials in solutions, are substantially reduced.

As optical energy is passed through waveguide 410 in the direction as indicated by arrow 421, a portion of the volume of nanohole 422 is illuminated by evanescent field 423, as the field extends into nanohole 422. As a result, only those reactants that are disposed at or near the exposed surface of the waveguide, within the nanohole, are subjected to sufficient illumination intensity, e.g., to emit a fluorescent signal. In some cases, the structure of the mask layer 420 and apertures therein, e.g., nanoholes 422, may provide optical confinement within the apertures to attenuate the illumination that enters the reaction region. For example, in some embodiments, apertures disposed within a mask layer are zero-mode waveguides.

The mask layer masks some portions of the waveguide but not other portions, which remain accessible to materials disposed over the overall substrate. In particular, the evanescent wave from exposed waveguide region can reach reagents deposited over the surface of the overall substrate, and particularly within analyte regions. By virtue of the mask layer, the evanescent wave from the other blocked portions of the waveguide will not reach any materials deposited over the surface of the substrate. As a result, one can pre-select those regions that are optically interrogable, and thus direct optical systems appropriately.

Figure 4C:
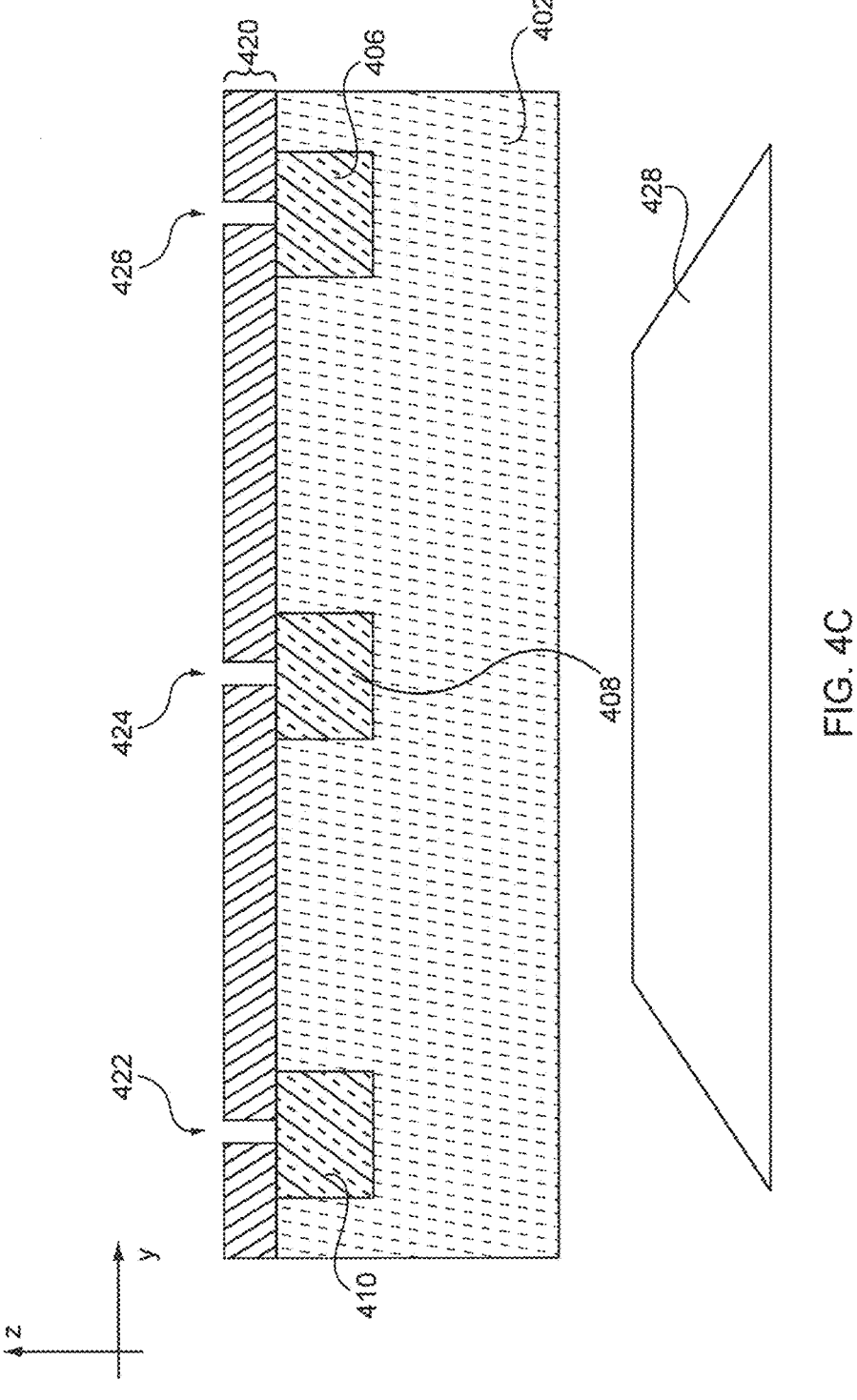

A cross section through the detection region of example device 400, where the section runs perpendicular and through three arrayed waveguides, e.g., waveguides 406, 408 and 410, is schematically illustrated in FIG. 4C. (Each waveguide has a separate waveguide core and waveguide cladding, not shown.) Again, as shown, analyte regions, e.g., nanoholes 422, 424 and 426 are disposed through mask layer 420, exposing the surface of waveguides 406-410. A portion of nanoholes 422-426 can be illuminated by an evanescent field (not shown) emanating from waveguides 406-410 as light passes through the waveguides. Analytic processes occurring in nanoholes 422-426 may be observed by detection system 428.

Figure 5:
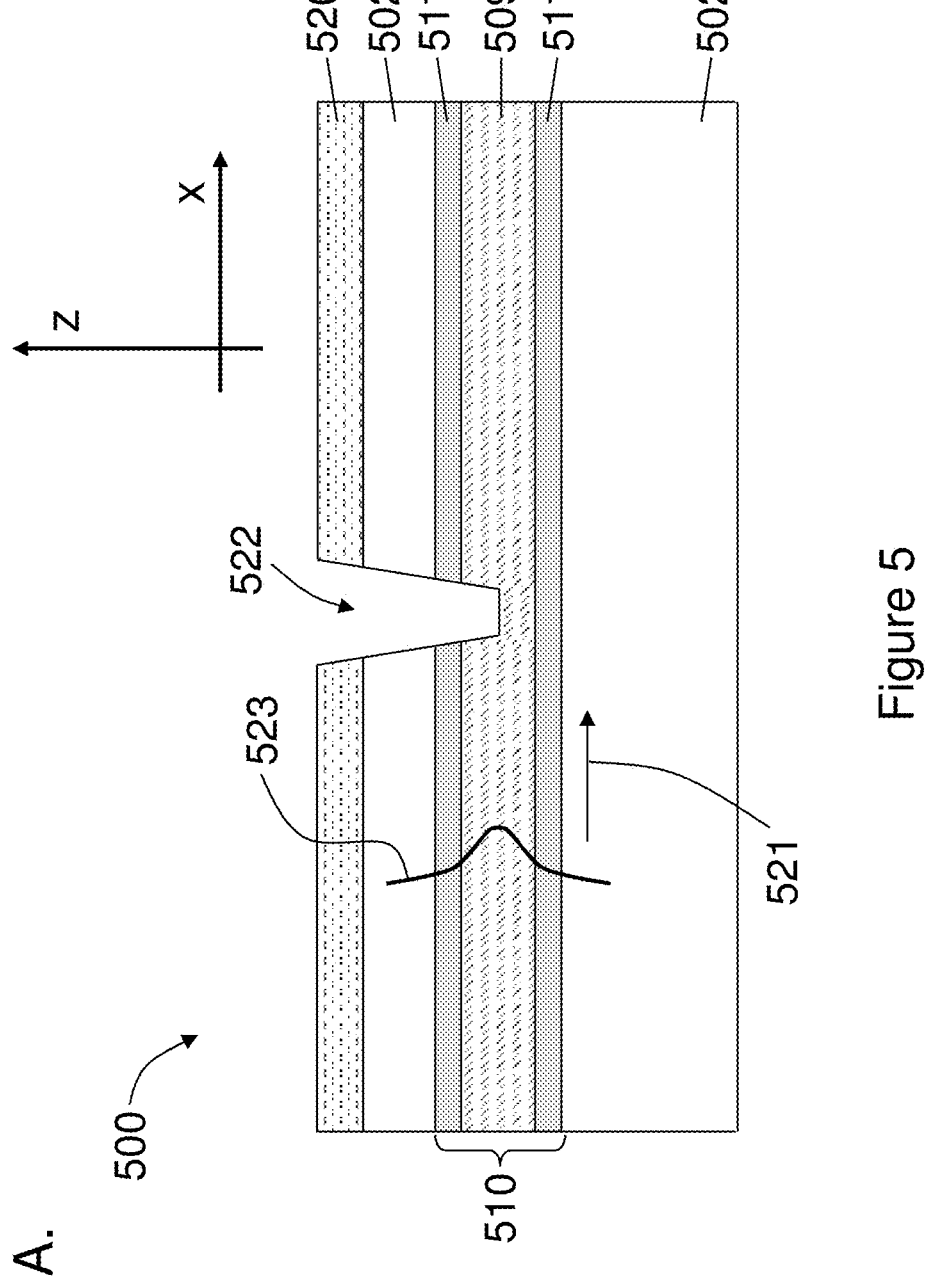
FIG. 5A schematically illustrates a cross-sectional view of an exemplary device of the invention that runs lengthwise through a channel waveguide.
FIG. 5B illustrates a cross-sectional view of the exemplary device depicted in FIG. 5A that runs perpendicular and through three arrayed channel waveguides.

A further exemplary analytic device that employs arrayed waveguides to illuminate a plurality of analyte regions, e.g., optically confined regions in which materials of interest are controllably illuminated in the manner described above, is schematically illustrated in FIGS. 5A-B. FIG. 5A schematically illustrates a cross-sectional view of example device 500, where the section runs lengthwise and through a channel waveguide 510 comprising waveguide core 509 and waveguide cladding 511. Device 500 includes a matrix 502. The channel waveguide core 509 has a higher refractive index than that of the waveguide cladding 511. A mask layer 520 is also illustrated on the surface of a top portion of the matrix 502. The analyte regions are disposed within apertures (e.g., nanohole 522) that extend through the mask layer 520, the top portion of the matrix 502, and the waveguide cladding 511, and extend into the waveguide core 509. As described above, nanoholes are preferable as compared to larger apertures, e.g., microholes, milliholes, centiholes, etc., because nanoholes are of such small cross sectional dimensions, e.g., 50-200 nm in cross section, that they provide a sufficiently small volume (e.g., attoliter- to zeptoliter-scale) of structural confinement such that issues of illumination of background or non-relevant regions, e.g., illumination of non-relevant materials in solutions, are substantially reduced, which facilitates detection and interrogation of single molecules or molecular complexes.

As optical energy is passed through waveguide 510 in the direction as indicated by arrow 521, a portion of the volume of nanohole 522 is illuminated by evanescent field 523, as the field passes through nanohole 522. As a result, only those reactants that are disposed at or near the evanescent field emanating from the waveguide, e.g., within an illumination volume within nanohole 522, are subjected to sufficient illumination, e.g., to emit a fluorescent signal. In some cases, the structure of the mask layer 520 and apertures, e.g., nanohole 522, may provide optical confinement within the apertures to attenuate the illumination that enters the reaction region. For example, in some embodiments, apertures disposed within a mask layer are zero-mode waveguides. Although the evanescent field shown in FIG. 5A does not extend to the mask layer, one of ordinary skill will readily recognize that different intensities of light can be propagated in channel waveguide 510, so in other embodiments an evanescent wave may extend to the mask layer. In such embodiments, the presence of an opaque mask layer can prevent excitation of reagents disposed over the surface of the substrate. Further, at least a portion of any signal emitted from reagents outside of the apertures (e.g., excited by light passing through the top of the aperture 522) is blocked from re-entering the aperture, thereby reducing background noise.

A cross-section through a detection region of example device 500, where the section runs perpendicular and through three arrayed waveguides, e.g., waveguides 506-510, is schematically illustrated in FIG. 5B. Again, as shown, analyte regions, e.g., nanoholes 522-526 are disposed through mask layer 520, through the top portion of the matrix 502, and through the waveguide claddings into the waveguide cores of waveguides 506, 508, and 510. A portion of nanoholes 522-526 can be illuminated by an evanescent field (not shown) emanating from waveguides 506-510 as light passes through them. Analytic processes occurring in nanoholes 522-526 may be observed by detection system 528.

The waveguide arrays of the present invention are in no way limited by the example waveguide arrays described above and illustrated in FIGS. 4A-C and 5A-B, as additional configurations and functionalities are possible, including those described below.

Waveguide Array Fabrication

In some cases, the waveguides described herein are generally produced using conventional ion implantation techniques to selectively ion dope selected regions of substrates, e.g., $SiO_2$ based substrates, to provide patterned regions of higher refractive index, so as to function as waveguides embedded in the underlying substrate. Examples of such devices are disclosed in, e.g., Marcuse, Theory of Dielectric Optical Waveguides, Second Ed. (Academic Press 1991). Alternate waveguide fabrication processes and configurations are equally applicable to the present invention, including hybrid material waveguides, e.g., employing polymeric materials as a portion or all of the subject substrate, e.g., a polymer core having a first refractive index, disposed within a substrate of another material having a second refractive index, which may be polymeric, or another material, e.g., silicon, glass, quartz, etc. For example, waveguides of the invention can be produced by depositing $Si_3N_4$ via chemical vapor deposition (CVD), e.g., low pressure chemical vapor deposition (LPCVD).

Waveguide substrates including mask layers may be prepared by a variety of known fabrication techniques. For example, lithographic techniques may be used to define the mask layer out of polymeric materials, such as photoresists, using e.g., conventional photolithography, e-beam lithography, or the like. Alternatively, lithographic techniques may be applied in conjunction with layer deposition methods to deposit metal mask layers, e.g., using aluminum, gold, platinum, chrome, or other conventionally used metals, or other inorganic mask layers, e.g., silica based substrates such as silicon, $SiO_2$, or the like. Alternatively, negative tone processes may be employed to define pillars of resists that correspond to the apertures, e.g., nanoholes (See, e.g., U.S. Pat. No. 7,170,050, previously incorporated herein by reference). The mask layer is then deposited over the resist pillars and the pillars are subsequently removed. In particularly preferred aspects, both the underlying substrate and the mask layer are fabricated from the same material, which in particularly preferred aspects, is a transparent substrate material such as an $SiO_2$ based substrate such as glass, quartz, or fused silica. By providing the mask and underlying layers of the same material, one can ensure that the two layers have the same interactivity with the environments to which they are exposed, and thus minimize any hybrid surface interactions.

In the case of $SiO_2$ based substrates and mask layers, conventional fabrication processes may be employed. In particular, a glass substrate bearing the surface exposed waveguide has a layer of resist deposited over its surface. A negative of the mask layer is then defined by appropriate exposure and development of the resist layer to provide resist islands where one wishes to retain access to the underlying waveguide. The mask layer is then deposited over the surface and the remaining resist islands are removed, e.g., through a lift off process, to provide the openings to the underlying waveguides. In the case of metal layers, deposition may be accomplished through a number of means, including evaporation, sputtering or the like. Such processes are described in, e.g., U.S. Pat. No. 7,170,050, which is incorporated herein by reference in its entirety for all purposes. In the case of silica based mask layers, a CVD process may be employed to deposit a silicon layer onto the surface. Following lift off of the resist layer, a thermal oxidation process can convert the mask layer to $SiO_2$. Alternatively, etching methods may be used to etch access points to underlying waveguides using conventional processes. For example, a silicon layer may be deposited over an underlying waveguide substrate. A resist layer is then deposited over the surface of the silicon layer and exposed and developed to define the pattern of the mask. The access points are then etched from the silicon layer using an appropriate differential etch to remove silicon but not the underlying $SiO_2$ substrate. Once the mask layer is defined, the silicon layer is again converted to $SiO_2$ using, e.g., a thermal oxidation process.

In addition to the advantages of reduced autofluorescence, waveguide substrates having an integrated mask layer provide advantages of optical alignment over similar arrays of wells or structures that are illuminated through non-integrated optical paths. For example, in some cases, illuminating an ordered array of reaction regions with minimal excess illumination involves directing excitation illumination at the various regions by presenting a corresponding array of illumination spots. In doing so, one must take substantial care in aligning the optical presentation of the illumination spots to the ordered array of reaction regions. Such alignment presents challenges of both design and robustness, as such systems may be prone to drifting or other misalignment influences. Where, as in the present invention, illumination is integrated or "hard wired" into the substrate by virtue of the integrated waveguide, alignment is automatic as a result of the substrate fabrication process. Further the possibility of loss of alignment over time, e.g., drift, is eliminated.

In other cases, surface features may include other confinement strategies, including, e.g., chemical surface functionalities that are useful in a variety of surface analytical operations, such as hydrophobic coatings or hydrophilic coatings that are optionally patterned, to provide confinement or direction to aqueous materials, chemical derivatization, e.g., to facilitate coupling of other functional groups or otherwise, e.g., by providing hydrophobic barriers partially or completely surrounding a desired region, or by providing immobilized coupling groups in desired reaction regions for immobilization of specific reagents. As will be appreciated, in some cases, particularly where structural confinement is provided upon the surface of the substrate, it may not be necessary to divide up light through a series of discrete waveguides in a given substrate. In particular, because one can obtain a desired level of multiplex and spatial separation organization from structurally dividing up the surface, one need not obtain that property through the use of separate waveguides. In such cases, a single field waveguide disposed at the surface of the substrate will suffice to deliver light to the various reaction regions on the surface of the substrate, e.g., as defined by the mask layer.

In addition to structures and strategies that provide for positioning and/or confinement upon a substrate surface, other components may be provided upon a substrate, including backside coatings for the substrate, e.g., antireflective coatings, optical indicator components, e.g., structures, marks, etc. for the positioning and or alignment of the substrate, its constituent waveguides, and/or for alignment of other components. Other components may include substrate packaging components, e.g., that provide fluidic interfaces with the substrate surface, such as flow cells, wells or recesses, channel networks, or the like, as macrostructures as compared to the surface defined structures above, as well as alignment structures and casings that provide structural protection for the underlying substrates and interactive functionality between the substrates and instrument systems that work with/analyze the substrates.

Waveguide Configurations and Structures

While primarily illustrated with respect to waveguide arrays that include a plurality of parallel waveguides, the invention may also include patterned waveguides that have a variety of different configurations, including serpentine waveguides, branched waveguides, interleaved waveguides, divergent waveguides, convergent waveguides or any of a variety of configurations depending upon the desired application. For example, where it is desired to provide evanescent illumination to larger areas of the substrate, it may be desirable to provide non-linear waveguides, such as serpentine waveguides, as well as larger area waveguides, such as wider or slab waveguide(s), or alternatively and likely preferably, larger numbers of parallel or similarly situated waveguides. The waveguide substrates may include a single waveguide that may span a fraction of the width of the substrate or substantially all of that width. In accordance with preferred aspects however, waveguide arrays are used to split individual originating beams into two or more waveguides, preferably more than 10 waveguides, more than 20 waveguides, more than 40 waveguides, and in some cases more than 50 waveguides or even more than 100, 1000, 5000 or more waveguides. The number of waveguides may typically vary greatly depending upon the size of the substrate used, and the optical resolution of the detection system, e.g., its ability to distinguish materials proximal to different waveguides.

The waveguides may individually vary in the size of the core region in order to vary the evanescent field that one can access. Typically, the waveguides will have a cross sectional dimension of from about 0.1 to about 10 µm, preferably from about 0.2 to about 2 µm and more preferably from about 0.3 to about 0.6 µm, and may be circular, oval, rectangular, lobed, or flattened (e.g., wide in the z dimension and narrow in the y dimension, or vice versa). In addition, the cross sectional dimension of a waveguide may be continuous or vary along the length of the waveguide. A variety of other waveguide dimensions may be employed as well, depending upon the desired application. For example, in some cases, a single waveguide may be used where the cross-sectional dimension of the waveguide is substantially the same as the substrate width or length, e.g., a single waveguide that substantially spans a substrate's width. Notwithstanding the foregoing, preferred aspects will provide arrayed waveguides, e.g., multiple waveguides typically arranged in parallel linear format.

A variety of different waveguide structures are exploitable in the present invention. In particular, the waveguide arrays of the invention may employ embedded and/or channel waveguides. Details regarding waveguide structures that can be employed in the present invention are provided in Lundquist et al., U.S. Patent Publication No. 2008-0128627, entitled SUBSTRATES, SYSTEMS AND METHODS FOR ANALYZING MATERIALS, incorporated herein by reference in its entirety for all purposes. For purposes of the invention, a waveguide that is referred to as being disposed upon or within the surface of a substrate encompasses waveguides that are disposed on but above the surface, within the substrate but at or exposed to the surface, or are disposed within the substrate, but sufficiently proximal to the surface that the evanescent wave from light passing through the waveguide still reaches above the surface to provide an illumination volume.

II. Waveguide Arrays with Additional Functionalities

The waveguide arrays of the present invention can include additional optical functionalities, including, e.g., specific types of nanoscale apertures such as zero-mode waveguides (ZMWs) that provide optical confinement of illumination light in addition to structural confinement. Further details regarding ZMWs can be found in U.S. Pat. Nos. 6,991,726 and 7,013,054, previously incorporated herein by reference. Other optical functionalities that may be integrated into or upon the substrates include lenses, filters, antireflective coatings, or the like. Other functionalities may be incorporated into the fabricated substrate that operate on and/or in conjunction with the waveguides or waveguide arrays of the invention. For example, optical switching or attenuation components may be provided upon or within the substrates of the invention to selectively direct and/or modulate the light passing through a given waveguide or waveguides.

In addition to the optical functionalities of the substrates of the invention, in some cases, such substrates may include additional functionalities that provide a defined region on the substrate surface to limit the access that reagents or other elements have to the illumination zone above a waveguide. For example, in some cases, the substrates may include a patterned structure or set of structures over the surface of the substrate providing selected exposure of the surface exposed waveguide(s). Such selected regions may provide limited areas of illumination on a given substrate by blocking the illumination region existing above other portions of the waveguide(s), such as a mask layer. As a result, only selected portions of the surface will be within the illumination or detection region of the waveguides. Such regions may be selected to align with detection systems or the requirements of such systems, e.g., sample spacing permitting spectral separation of signals from each region (See, e.g., U.S. patent application Ser. No. 11/704,733, filed Feb. 9, 2007, which is incorporated herein by reference in its entirety for all purposes). In addition to limited access, such structures may also provide structural confinement of reactions or their components, such as wells or channels. In one aspect, for example, microfluidic channels may be provided disposed over surface exposed waveguide or waveguide array. Such channels may be independently used to deliver different reagents to different portions of a waveguide or waveguide array.

Waveguide Arrays for Enhanced Optical Energy Propagation

The present invention provides devices for waveguide-based illumination of analyte regions in apertures (e.g., nanoholes or ZMWs) that reduce the variation in illumination over the length of the waveguide, for example, by mitigating propagation losses over the length of the waveguide. Such propagation losses can be further exacerbated by a metal layer disposed over the surface of the substrate, because it can absorb optical energy from a surface-exposed or core-exposed waveguide, or even a waveguide near to the surface of the substrate. Such metal layers are typically found in conventional ZMW arrays, presenting a challenge for combining such arrays with waveguide illumination strategies.

One of the limitations of waveguide illumination is optical attenuation as the light propagates down the guide resulting in a reduction in power at different locations in the guide. For example, a particular laser intensity coupled into the waveguide will experience a slow decrease in energy density as light travels down the guide due to propagation losses, with the highest power at the end nearest the illumination source and the lowest at the end farthest from the illumination source. The degree of the propagation loss is typically a function of the designed geometry and manufacturing tolerances, and presents a challenge to performing multiplexed analytical reactions because it constrains the spatial range of the usable waveguide structure. It is important to maximize the distance over which the laser intensity is sufficiently uniform, in order to maximize the multiplex capabilities of the system. It is therefore an object of the present invention to provide uniform power over the length of a waveguide, e.g., to promote uniform illumination of all reaction sites to be illuminated by the waveguide.

In certain embodiments, a waveguide is tapered such that the core gradually becomes thinner along the direction of propagation. This causes the degree of light confinement to be gradually increased, which can offset the gradual reduction in the total amount of power in the guide due to propagation losses and essentially maintain a desired mode shape and field strength for the optical energy propagated over the length of the waveguide core. In principle, the sum of propagation losses is balanced by the decreasing core size such that uniformity of evanescent field strength can be held constant for an arbitrarily long distance, with limitations to the strength of the evanescent field also being dependent on the starting laser power and the starting waveguide core dimensions. For a given waveguide substrate, once the propagation loss is determined the waveguide geometry can be designed to smoothly vary, thereby modifying the degree of confinement such that the relative field strength at the point of interest increases at the same rate that propagation losses reduce the total power in the guide. For example, a tapered waveguide core can be widest at the portion most proximal to the light source, slowly narrowing along the guide, with the field localization increasing at the same rate that propagation losses are reducing the waveguide field strength. The tapering can take place in any direction including the z direction (top to bottom), the y direction (side to side), or a combination thereof.

In certain embodiments, a waveguide cladding above a waveguide core in a waveguide substrate is tapered such that the waveguide core is slowly brought closer to the reaction sites at the surface of the substrate by an ever-decreasing width of the waveguide cladding layer that separates the core from the reaction sites. As such, although there is propagation loss from a waveguide with a non-tapered geometry, as the field strength in the waveguide decreases, it is brought closer to the reaction sites, and this increasing proximity compensates for an overall reduced field strength. In some embodiments, both the waveguide cladding layer and waveguide core are be tapered to mitigate loss of field strength due to propagation losses.

In other embodiments, the refractive index of the waveguide core or waveguide cladding layer is gradually modified along the propagation direction to smoothly adjust the degree of confinement and relative field strength. These waveguide substrates can be fabricated using standard waveguide manufacturing techniques known in the art. Further, embodiments of the invention may comprise combinations of various strategies for enhancing optical energy propagation and mitigating propagation loss, e.g., varying the taper, depth, and/or refractive indices of waveguide cores and/or waveguide claddings.

In certain aspects, a waveguide designed to propagate light of multiple different wavelengths provides various benefits to methods, devices, and systems of the invention. However, for a waveguide of a given geometrical and material structure, different propagation wavelengths behave differently. For example, for available material structures there is no solution that is single-mode at both 488 nm and 643 nm, and although a waveguide can be designed to be single-mode for two wavelengths, such a waveguide would not be expected to promote similar evanescent field strength for both wavelengths. Although similar field strength may be achieved by increasing the laser power of the shorter wavelength laser, this could cause the total power required for the device to be several times larger and is undesirable for various reasons, including higher autofluorescence, increased heat in the waveguide (which could damage the substrate and/or increase the temperature at a reaction site), and inefficient use of laser power. A multimode structure would experience modal interference that would cause different locations along the guide to show very different field strengths, and so also does not provide a practical means to propagate multiple different wavelengths of light in a substantially uniform manner over the length of a waveguide.

An object of the invention is to provide a desired evanescent field strength for light of multiple wavelengths at a specific location or set of locations, e.g., reaction sites. A further object of the invention is to detect optical energy of multiple different wavelengths, e.g., in the visible spectrum, simultaneously in real time, e.g., during an ongoing enzymatic reaction. In preferred embodiments, a waveguide designed to achieve the same or similar evanescent field strength for multiple wavelengths without the undesirable side-effects of using a single-mode or multi-mode waveguide is provided. The field profile of guided modes of different wavelengths are not equivalent, and in general the farther apart the wavelengths, the larger the difference in field strength. In certain preferred embodiments, the invention provides a "polarized waveguide" designed to utilize a different polarization for different excitation wavelengths to be simultaneously propagated in the waveguide. In planar waveguides, p-polarized modes are more tightly confined than s-polarized modes. In channel guides the propagation solutions are preferably divided into two polarization categories, TE and TM polarized modes. In this way, a single waveguide geometry can be an adjustable solution to propagation of light of two different wavelengths. The different polarizations for the different wavelengths can be designed to provide the same evanescent field strength for both wavelengths at the desired location(s). Polarization can be manipulated independently in several ways that are well known in the art. For example, a polarizing prism can be used to combine and perfectly overlap two different light beams. A wave retarding plate can also be used to independently manipulate the polarizations of two beams having different wavelengths. The Faraday effect can be used to independently manipulate two beams even after they are collinear. Finally, diffraction gratings and Holographic Optica Elements (HOE's) can be used to direct multiple beams of different wavelengths separately to achieve the desired alignment and efficient coupling into a planar waveguide structure with independent polarization control. In certain embodiments, the waveguides are specifically tapered to provide the same evanescent field strength and desired mode shape for both wavelengths. In certain embodiments of multi-laser systems different polarizations can be assigned to best balance the field strength. In certain preferred embodiments, the wavelengths of light propagated in a polarized waveguide are in the visible range (e.g., between about 380 nm and 750 nm; or in terms of frequency, between about 790 and 400 terahertz). In certain preferred embodiments, excitation light of at least two different wavelengths is simultaneously propagated in a single waveguide and used to illuminate different fluorescently labeled analytes in an illumination volume at a reaction site, emission light is emitted from the fluorescently labeled analytes in response to the excitation illumination, and the emission light is detected in real time. In certain preferred embodiments, light of at least two different wavelengths is propagated in a single waveguide, the wavelength of a first differs from the wavelength of a second by at least 50 nm, but also desirable are 100 nm, 200 nm, 300 nm, and 400 nm separations. The desired separation of a particular configuration is determined by both the waveguide structure, the nanohole structure, and the chemical fluorophores involved in the application.

ZMW array substrates typically employ an opaque mask layer, e.g., aluminum, chromium, or the like, deposited over a transparent substrate layer. A series of apertures are disposed through the mask layer to the transparent layer. Disposing a plurality of ZMWs proximal to, and along, a core-exposed waveguide for waveguide-based illumination of ZMWs entails the waveguide being situated immediately beneath a metal layer. As will be appreciated, over the length of the waveguide, propagation losses can occur due to the metal layer being in direct contact with the waveguide core. Such propagation losses may present difficulties for utilizing the waveguide for both transporting optical energy around the substrate and illuminating the reaction regions, e.g., ZMWs, disposed proximal to the waveguide core.

Figure 6:
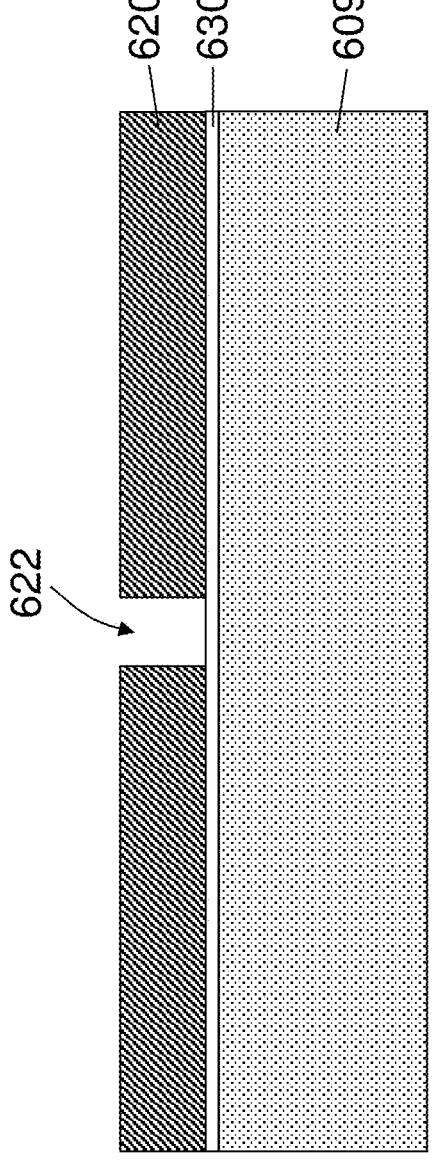
FIG. 6 provides an illustrative example of a waveguide-illuminated ZMW array comprising a nonmetal mask layer.

In certain embodiments, such propagation losses can be mitigated by substituting the metal mask layer for a non-metal mask layer. An illustrative example of such a wave-guide-illuminated ZMW is provided is FIG. 6 in which a waveguide core 609 made of a high refractive index material (e.g., $LiNbO_3$, n=2.3; $Si_3N_4$, n=2; $SiO_x$, $N_y$, n=1.55 to 2; etc.) is combined with a mask layer 620 made of aluminum oxide ($Al_2O_3$, n=1.7) and an intervening thin layer of glass 630 (e.g., fused silica). The mask layer 620 is patterned over the glass layer 630 to generate the ZMW structure 622. This type of waveguide-illuminated ZMW provides benefits beyond the mitigation of propagation losses, as well. For example, it provides optical confinement of the evanescent field to the reaction site in an observation volume similar to those of conventional ZMW arrays, at least in part due to shorter evanescent decay lengths, which results in lower background signal, shorter diffusive residence times, and an overall lower signal-to-noise ratio when monitoring analyti-cal reactions illuminated by the waveguide. Further, con-ventional ZMW surface chemistry can also be used in these waveguide-illuminated ZMW arrays because the surface properties are the same, e.g., allowing biased immobilization of reaction components to the bottom, but not the sides of the ZMW (or vice versa). In general, the length of evanescent decay within the ZMW becomes shorter and the optical confinement becomes better as the refractive index of the core is increased and/or as the refractive index difference between the core and the mask layer is high. In certain embodiments, the thin glass layer can be substituted for other materials that support biased surface chemistries within the ZMW, and preferably support conventional ZMW surface chemistry, which is described elsewhere in the art (see below). In addition, the mask layer can be low refractive index materials other than aluminum oxide (such as, e.g., CVD and PECVD silicon oxide, Spin-on-Glass or boro-phosphoslicate glass (BPSG), etc.) that is subsequently coated with aluminum oxide to facilitate biased surface chemistry. The properties and methods of use of such materials are known to those of ordinary skill in the art. Of course, the glass floor of the ZMW would need to be protected from the aluminum oxide during the coating process. Methods for conventional surface chemistry in ZMWs is provided, e.g., in Korlach, et al. (2008) Proc. Natl. Acad. Sci. 105 (4): 1176-1181; U.S. Patent Publication Nos. 20070077564, 20070134128, 20070238679, 20080241892, 20080032301, 20080050747, and 20080220537; and U.S. patent application Ser. No. 11/645,125, filed Dec. 21, 2006, the disclosures of all of which are incorporated herein by reference in their entireties for all purposes.

In some exemplary embodiments, variations in (con-veyed) illumination over the distance of the waveguide may be achieved by providing function-specific waveguides within the substrate and coupling them. In particular, one may employ a first waveguide for the unimpeded transport of excitation illumination, which is then optically coupled to a second waveguide that serves to deliver the excitation illumination to the reaction region. In such cases, the devices provided by the invention may include both "shallow" and "deep" waveguides. The shallow waveguides e.g., wave-guides disposed just beneath the metal ZMW layer near the top surface of the substrate, function to illuminate the ZMWs within a detection region of the array. The deep waveguides are buried within the substrate at a distance further from the metal layer of ZMWs than the shallow waveguides, and function to transport power around the substrate without the propagation losses associated with waveguides situated near the ZMW layer. Although described below primarily with reference to ZMW arrays, combinations of waveguides of differing depths can also be used to illuminate reaction sites on other types of waveguide substrates, e.g. planar waveguide substrates or waveguide substrates comprising apertures other than ZMWs, e.g., other types of nanometer-scale apertures.

As will be appreciated, optical energy transported through deep waveguides can be coupled to shallow waveguides by a variety of means. For example, an evanescent field ema-nating from the deep waveguides, e.g., a light field that decays exponentially as a function of distance from the deep waveguide surface, can be exploited to illuminate the shal-low waveguides. Coupling optical energy between the deep and shallow waveguides can be enhanced by altering the shape of the deep waveguide, e.g., tapering the cross sec-tional area of the deep waveguide such that the cross sectional area of the deep waveguide is smaller at regions of the array where coupling between the deep and shallow waveguide is desired. For example, a smaller cross sectional area of the waveguide at a given position permits the evanescent field to extend a greater distance from the deep waveguide core at that position. For example, a decreased cross sectional area of the deep waveguide core can ensure that the evanescent field extends to, or beyond, the portion of the shallow waveguide on the side opposite the deep waveguide, thereby providing maximal illumination of the shallow waveguide by the deep waveguide. In other embodi-ments, the matrix separating the deep waveguide from the shallow waveguide is varied to allow more efficient transfer of optical energy to the shallow waveguide in desired regions, e.g., detection regions. Coupling between the deep and shallow waveguides can also be enhanced by altering the optical properties of the core or cladding, e.g., the thickness or index of refraction of the cladding, of the deep waveguides. Further, a "leaky-mode" in the deep waveguide can be created by patterning and etching a shallow grating on it. The grating can be optimized, e.g., by altering the period, duty cycle and/or depth of the grating, to enhance optical coupling to the shallow waveguide. Other methods for coupling the deep and shallow waveguides known to those of ordinary skill in the art are also contemplated.

Figure 7:
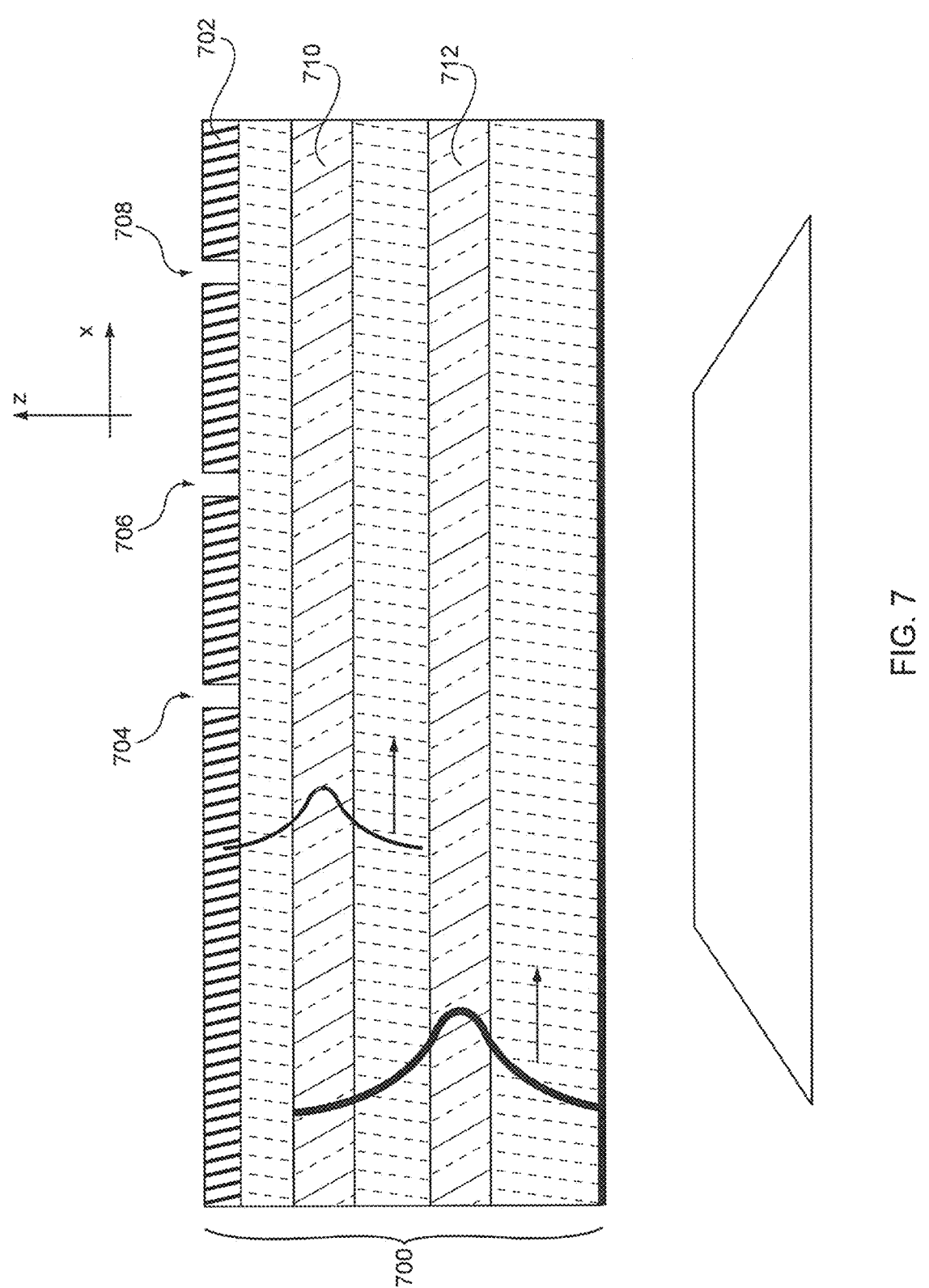
FIG. 7 schematically illustrates an analytic device that utilizes waveguides of different depths within a substrate to distribute optical energy around the substrate.

A cross section of the detection region of an example device that employs shallow and deep waveguides to illu-minate a plurality of ZMWs is schematically illustrated in FIG. 7. As shown, substrate 700 is provided including top metal layer 702 through which holes for the formation of ZMWs 704, 706 and 708 are etched. Shallow waveguide 710 lies just beneath the ZMW layer. Deep waveguide 712 is disposed within substrate 700 beneath shallow waveguide 710. Deep waveguides 712 transports optical energy around the device with mitigated propagation loss resulting from metal layer 702 at least in part due to its distance from metal layer 702. As shown, optical energy is coupled from deep waveguides 712 to shallow waveguides 710, permitting ZMW illumination by shallow waveguides 710 with enhanced efficiency as compared to illumination by a wave-guide responsible for both transporting optical energy across the device and ZMW illumination.

In addition to the above-described waveguide arrays that address propagation losses associated with a metal ZMW layer disposed upon the waveguides, the present invention also provides waveguide arrays in which individual wave-guides terminate in metal islands that include one or more ZMWs. By providing each metal island with its own illu-mination guide entrance, the propagation losses associated with guiding illumination light beneath an extensive metal surface, e.g., a continuous metal layer providing a plurality of ZMWs, are eliminated. The metal islands of the devices can comprise a broad variety of metals known to those of ordinary skill in the art and disclosed elsewhere herein, including but not limited to Al, Au, Ag, Pt, Ti, and Cr.

Figure 8:
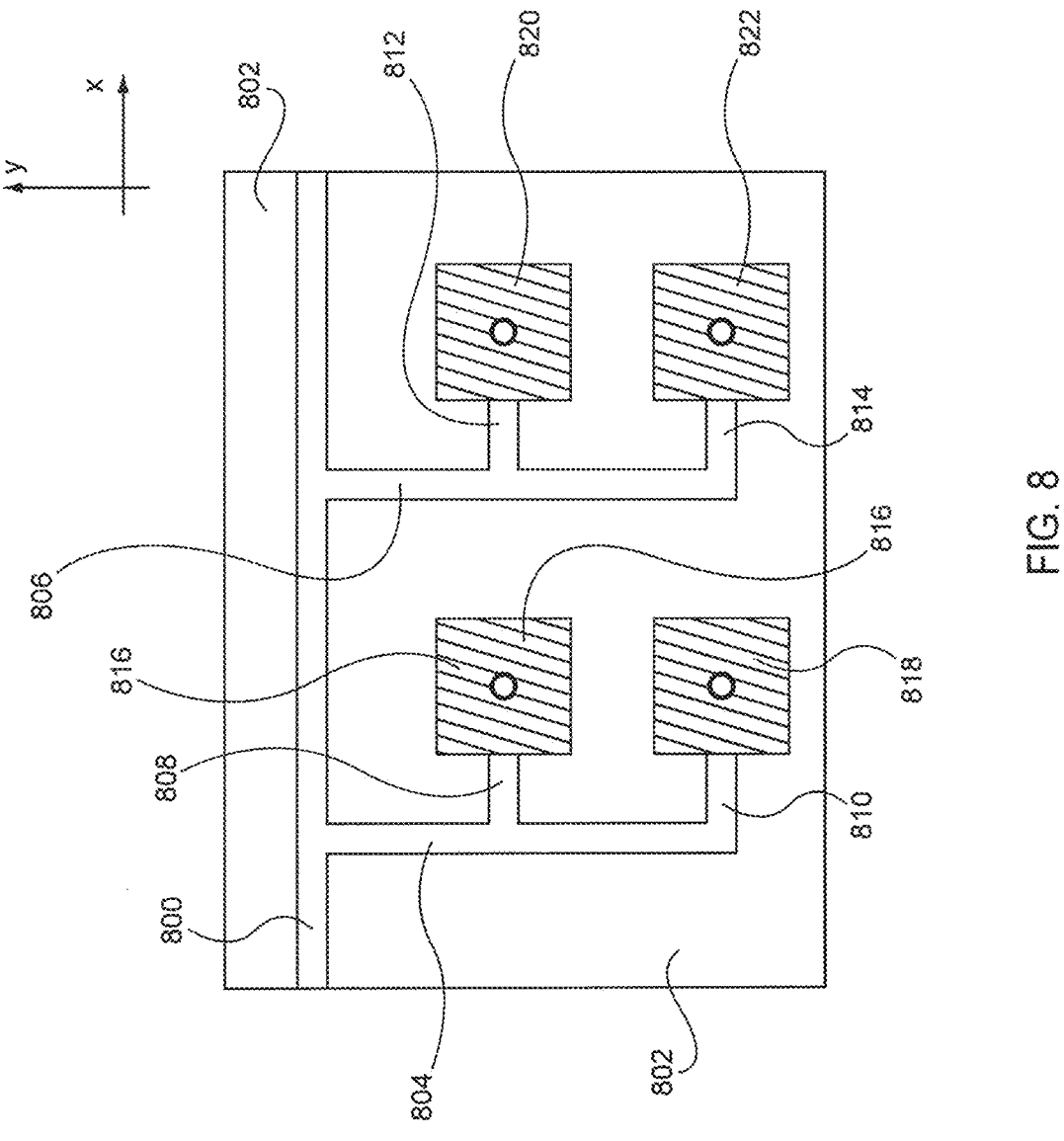
FIG. 8 schematically illustrates a device for distributing optical energy to zero-mode waveguides disposed upon or within a substrate.

An example waveguide array in which metal islands including one or more ZMWs are illuminated by waveguides is schematically illustrated in FIG. 8. As shown, primary waveguide 800 is disposed upon or within substrate 802. Secondary waveguides 804 and 806 are configured to receive optical energy from primary waveguide 800. Tertiary waveguides 808, 810, 812 and 814 are configured to receive optical energy from secondary waveguides 804 and 806. As shown, tertiary waveguides 808-814 terminate in metal islands 816, 818, 820 and 822 that include a ZMW. It will be appreciated that the metal island can also include two or more ZMWs. The ZMWs can be disposed through the metal islands such that the ZMW is aligned with, and disposed upon or proximal to, the external surface of tertiary waveguides 808-814, permitting illumination of the ZMWs by an evanescent field emanating from tertiary waveguides 808-814 as optical energy passes through the tertiary waveguides.

Waveguide Arrays for Improved Uniformity of Analyte Region Illumination

Conventional optical splitters, e.g., Y splitters or T splitters, are often employed for splitting optical energy from an originating waveguide into 2 or more branch waveguides. To split optical energy to, e.g., 32 (or N) waveguides, a star coupler or tree coupler can be used. A tree coupler comprises multiple stages of 1×2 Y splitters, e.g., 5 stages for a 1×32 splitter. For conventional Y splitters working at telecom wavelength (1550 nm), the splitting error is approximately 0.2 dB (2.3%), i.e., the power difference between the two branches is about 0.2 dB (2.3%). For a 5-stage 1×32 splitter, the compound splitting error can reach 1 dB (11%). For a splitter working at visible wavelength, the expected splitting error would scale up with the frequency of the wavelength. Thus, the compound splitting error for a visible 1×32 splitter could reach as high as 30-40%. This error can result in inconsistent illumination among arrayed waveguides and, accordingly, analyte regions disposed proximal to the waveguides. Non-uniform analyte region illumination can adversely affect the functionality of an analytic device, e.g., a waveguide array and optical detection system for illumination and observation of a plurality of molecular processes. The present invention provides waveguide arrays that exhibit substantially uniform optical energy intensity among the arrayed waveguides.

The invention provides waveguide arrays for improved uniformity of analyte region illumination that include, e.g., optical gratings disposed upon an external surface of the waveguides. The gratings can be configured to couple free space light between a source of free space light and the waveguides. By providing each waveguide with gratings of uniform characteristics, e.g., uniform grating period, cross sectional area of the slits that make up the grating, and the like, optical energy is coupled to the waveguide cores such that illumination of the waveguides with optical energy of a desired intensity and wavelength is achieved. Because the gratings normalize the intensity of optical energy among the arrayed waveguides, the waveguides produce substantially uniform evanescent fields that emanate from the waveguides as light passes through the waveguides. Accordingly, analyte regions disposed proximal to the arrayed waveguides are illuminated with improved uniformity, and issues involving analyte regions receiving too much or too little illumination light are substantially reduced.

Figure 9A:
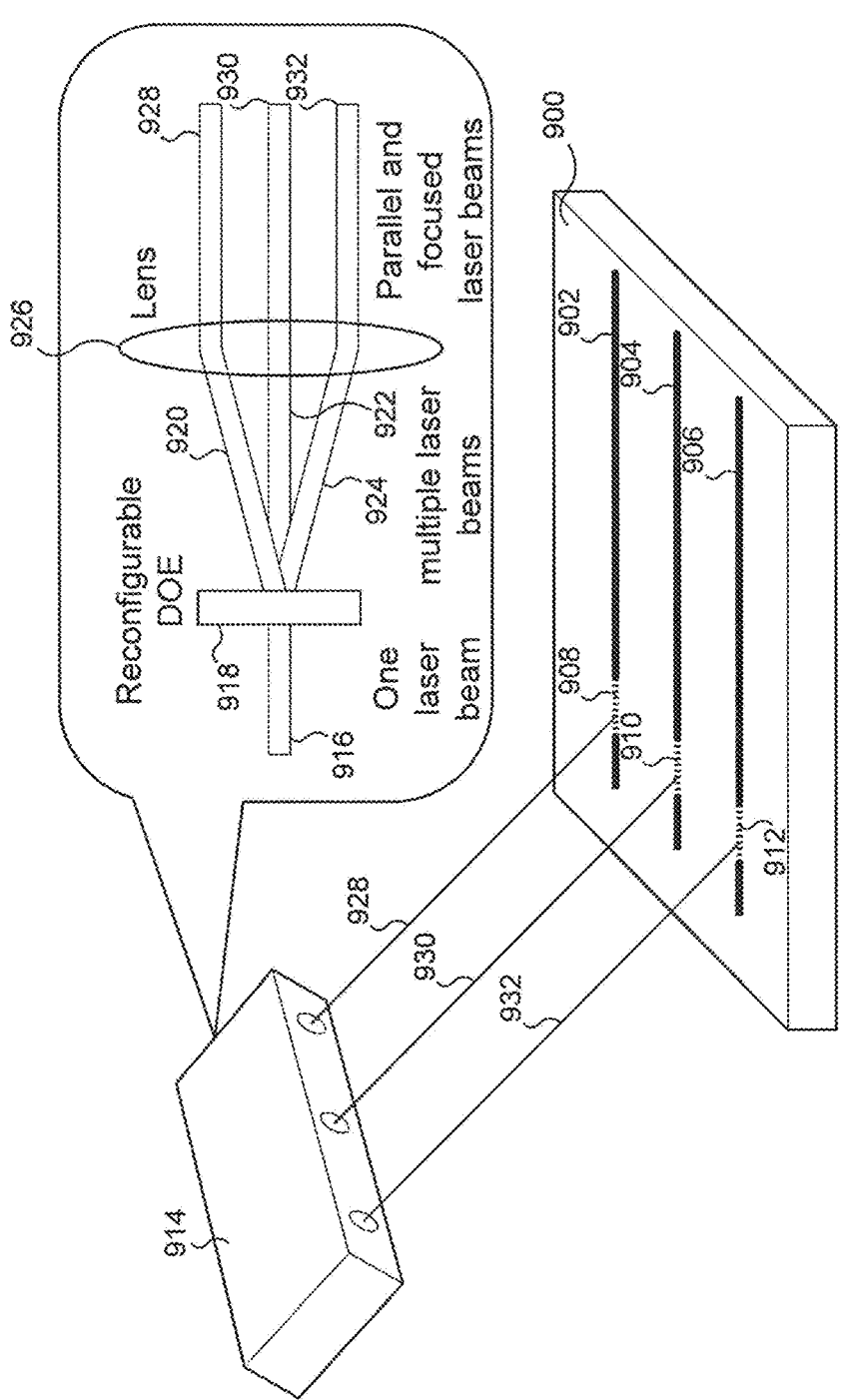
FIG. 9A schematically illustrates an overview of an analytic device that includes optical gratings for normalizing optical energy intensity among two or more waveguides.

An example device for achieving substantially uniform optical energy intensity among arrayed waveguides is schematically illustrated in FIG. 9A. As shown, substrate 900 is provided including a number of optical waveguides, e.g., surface-exposed waveguides 902, 904 and 906. Optical energy source 914 is provided for illumination of waveguides 902-906. Optical energy source 914 provides a single beam of optical energy 916, e.g., a single laser beam, which directs optical energy toward reconfigurable diffractive optical element 918. Reconfigurable diffractive optical element 918 splits the single beam of optical energy into multiple beams of optical energy, e.g., multiple laser beams 920, 922 and 924. Multiple laser beams 920-924 are passed through relay lens/microscope objective 926 to generate parallel and focused beams of optical energy, e.g., parallel and focused laser beams 928, 930 and 932. As shown, parallel and focused laser beams 928-932 are directed toward optical gratings, e.g., optical gratings 908, 910 and 912, disposed within a waveguide cladding layer (not shown) of, or proximal to, surface-exposed waveguides 902-906, respectively.

Figure 9B:
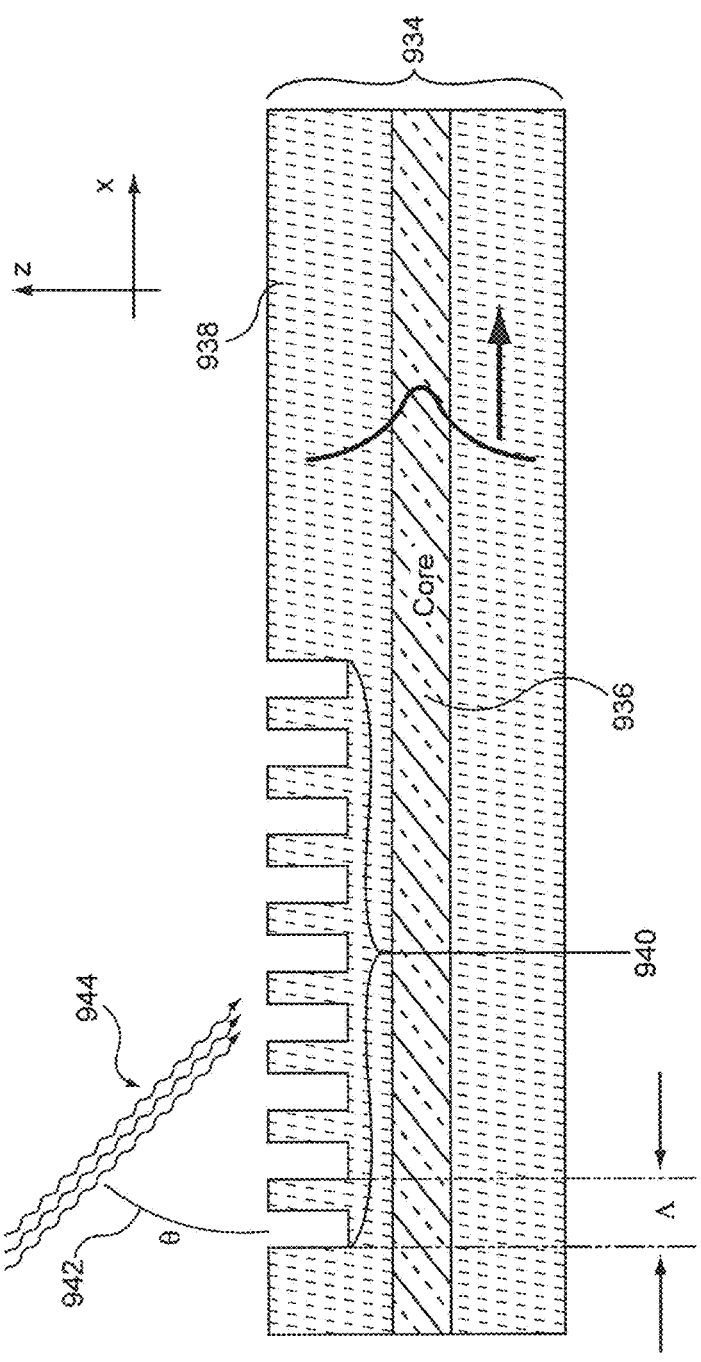
FIG. 9B schematically illustrates a close-up view of an analytic device, which includes an optical grating etched into the cladding of a waveguide core, being illuminated by free space optical energy.

A more detailed schematic illustration of optical gratings for coupling optical energy to a waveguide array is presented in FIG. 9B. Substrate 934 is provided including optical waveguide 936 and waveguide cladding layer 938 disposed proximal to optical waveguide core 936. Optical grating 940 can comprise submicrometer wide holes or slits periodically etched through waveguide cladding layer 938 proximal to waveguide core 936. The angle of incidence 942 of focused beam of optical energy 944 can be reconfigured and optimized according to the period of optical grating 940 to achieve optical energy of a desired wavelength within waveguide core 936 according to the following equation:

$$\cos\theta = \frac{n_2}{n_1} - \frac{l}{\Lambda}\cdot\frac{\lambda}{n_1},$$

$$l = \pm 1, \pm 2, \ldots.$$

where θ is the angle of the incident beam that creates the best overlap integral with the mode structure of the optical energy propagating in the waveguide, λ is the wavelength of optical mode propagation down the waveguide core, $n_1$ is the refractive index of the waveguide cladding material that includes the gratings, $n_2$ is the effective refractive index of the waveguide core for a propagation mode at wavelength λ, Λ is the pitch of the gratings in the top cladding layer of the waveguide, and/is a non-zero integer. The period of optical grating 940 can be adjusted during fabrication of the substrate for optimizing the optical coupling between the source of optical energy (not shown) and waveguide core 936.

Such gratings can be made by, e.g., etching periodical features through the waveguide cladding along a waveguide core, where the features can be, e.g., evenly spaced submicrometer sized holes or trenches lined up along the waveguide. The spacing and size of the features should satisfy the above-described coupling equation. For efficient fabrication of the device, the grating can be made on the same mask layer through which the analyte regions, e.g., nanoholes, are formed. Although described primarily in terms of waveguide arrays, such gratings can also be used to couple optical energy into other types of waveguide substrates, e.g., those comprising one or more planar waveguides.

Waveguide Arrays for Enhanced Waveguide Illumination Efficiency Within a Detection Region of the Array As opposed to previous illumination strategies where each analyte region of a substrate requires its own source of optical energy, e.g., a laser beam, for illumination, waveguide illumination has the advantage of illuminating a plurality of analyte regions, e.g., hundreds or thousands of analyte regions, using the power equivalent to a single laser beam. Despite the efficiency advantages of illuminating reaction regions via waveguides, improvements in waveguide illumination efficiency are desirable.

The present invention provides waveguide arrays that improve the illumination efficiency of the arrayed waveguides within a detection region of the array. The waveguide arrays of the invention include, e.g., optical grating pairs that flank a detection region of the array. Optical grating pairs can be disposed upon an external surface of the arrayed waveguide cores such that optical energy of a desired wavelength is reinforced within the cores and within a detection region of the array, e.g., the region of the array in which analyte regions are disposed proximal to the external surface of the waveguides. The grating-mediated reinforcement of optical energy of a desired wavelength within the detection region of the array is advantageous in numerous respects, e.g., decreasing the power requirements for illuminating the arrayed waveguides while still providing sufficient illumination of analyte regions by evanescent fields emanating from the waveguides during operation of the device.

Figure 10:
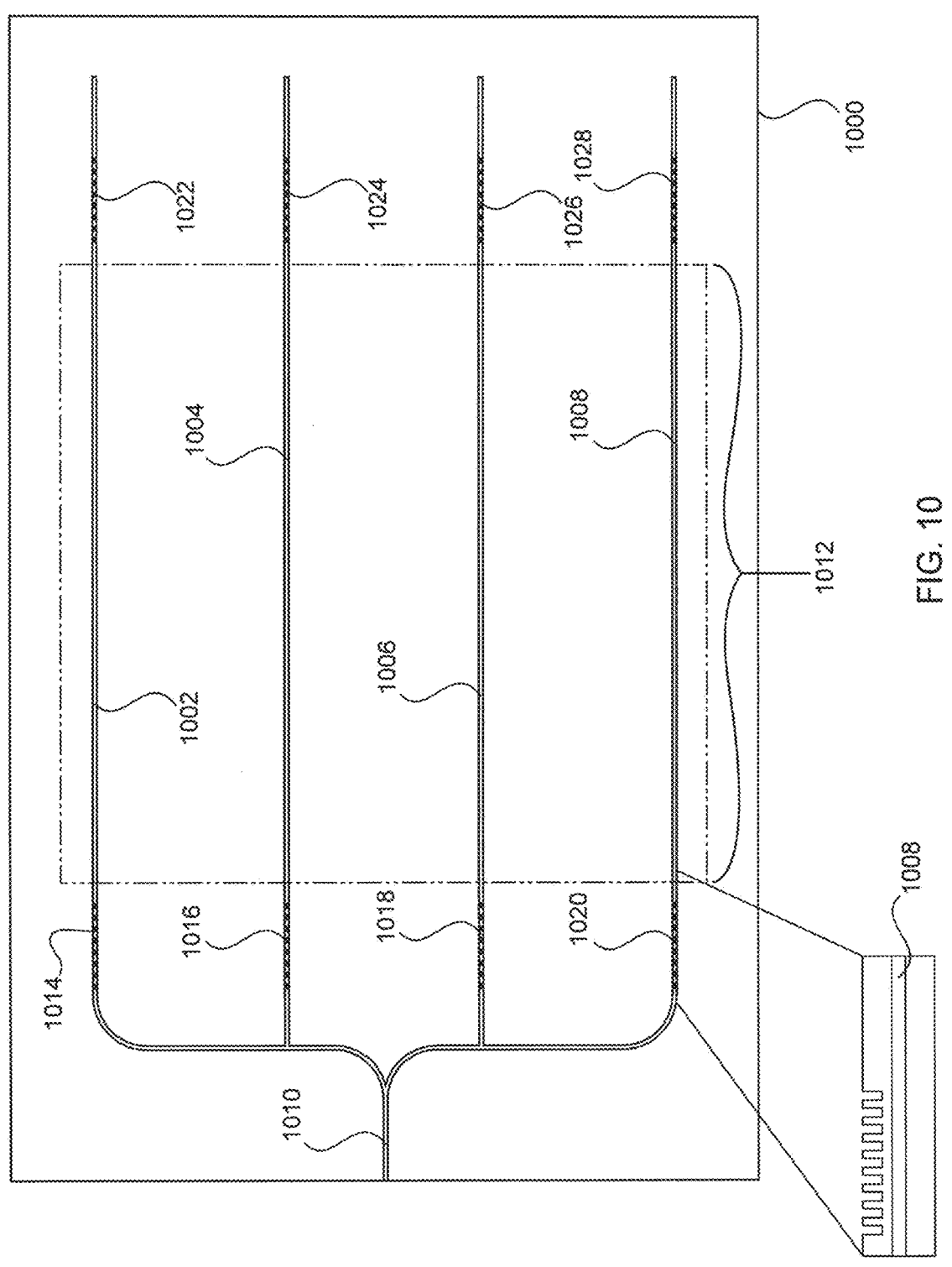
FIG. 10 schematically illustrates an analytic device that includes optical grating pairs for enhancing the illumination efficiency of waveguides within a detection region of the device.

FIG. 10 schematically illustrates an example waveguide array that employs optical grating pairs for enhanced illumination efficiency, e.g., by enhancing the electric field intensity within the detection region without a corresponding increase in the input power level. As shown, substrate 1000 is provided including a number of branch waveguides, e.g., surface exposed branch waveguides 1002, 1004, 1006 and 1008, that are optically coupled to originating waveguide 1010. A plurality of reaction regions (not shown) are disposed proximal to branch waveguides 1002-1008 within detection region 1012. Optical gratings 1014, 1016, 1018 and 1020, e.g., submicrometer wide holes or slits periodically etched through a waveguide cladding layer (not shown) proximal to each waveguide core, are disposed adjacent to detection region 1012 on a first side. Optical gratings 1022, 1024, 1026 and 1028 are disposed adjacent to detection region 1012 on a side opposite relative to the first side. The period of optical gratings 1014-1020 and 1022-1028 can be designed (e.g., based on the natural modes of oscillation of the input light) and fabricated such that optical energy of a desired wavelength is reinforced within detection region 1012 of the device, thereby enhancing the illumination efficiency of the waveguides within detection region 1012 without increasing (and potentially even decreasing) the power requirements of the device.

The present invention also provides waveguide arrays that improve the illumination efficiency of the arrayed waveguides within a detection region of the array by connecting waveguides to recycle the laser power, e.g. at the ends. For example, an end of a first waveguide can be attached to an end of a second waveguide by a bent waveguide, and multiple waveguides can be so attached in a single waveguide substrate. In some embodiments, an originating waveguide can be split into multiple branch waveguides, and the distal ends of the branch waveguides can be connected together. In other embodiments, multiple waveguides can be recombined into a single waveguide, e.g., to recycle laser power. For example, as described elsewhere herein, propagation loss causes a decrease in energy density as optical energy is propagated along the length of the waveguide, e.g., resulting in non-uniform optical energy across a detection region. The loss in power uniformity can be mitigated by "recombining" branch waveguides, e.g., within the detection region, to create a merged waveguide having a higher intensity optical energy than either of the branch waveguides, and the capability to propagate a desired energy intensity that is no longer propagated by the branch waveguides. In yet further embodiments, an originating waveguide is not split and is instead arranged in a serpentine manner to cross the detection region multiple times. In yet further embodiments, a combination of waveguide splitters, recombiners, and/or serpentine arrangements of waveguides is used to provide illumination to the detection region. The connected waveguides may or may not be adjacent to one another. Further, the waveguides may be connected two-by-two, e.g. using a bent waveguide connector. Alternatively, the waveguides may be connected with a reverse-splitter-type waveguide, e.g. where a single connecting waveguide connects more than two waveguide ends together. The number of relays or the total propagation length is determined by the propagation loss within each straight section of the branches and the loss in the bending region. The minimum bending radius is determined by the refractive index contrast of the core and cladding of the waveguides. The higher the refractive index contrast, the smaller the bending radius. In some embodiments, the bending radius requirement is relaxed by using three-dimensional connectors to join non-adjacent waveguides. Further, waveguides in the various configurations described above can also be combined with other aspects of the present invention. For example, a branch waveguide and/or a waveguide comprising optical grating pairs can be tapered or otherwise modified (e.g., with respect to refractive index, depth, and the like) to promote even illumination over the detection region, as described elsewhere herein.

Figure 11:
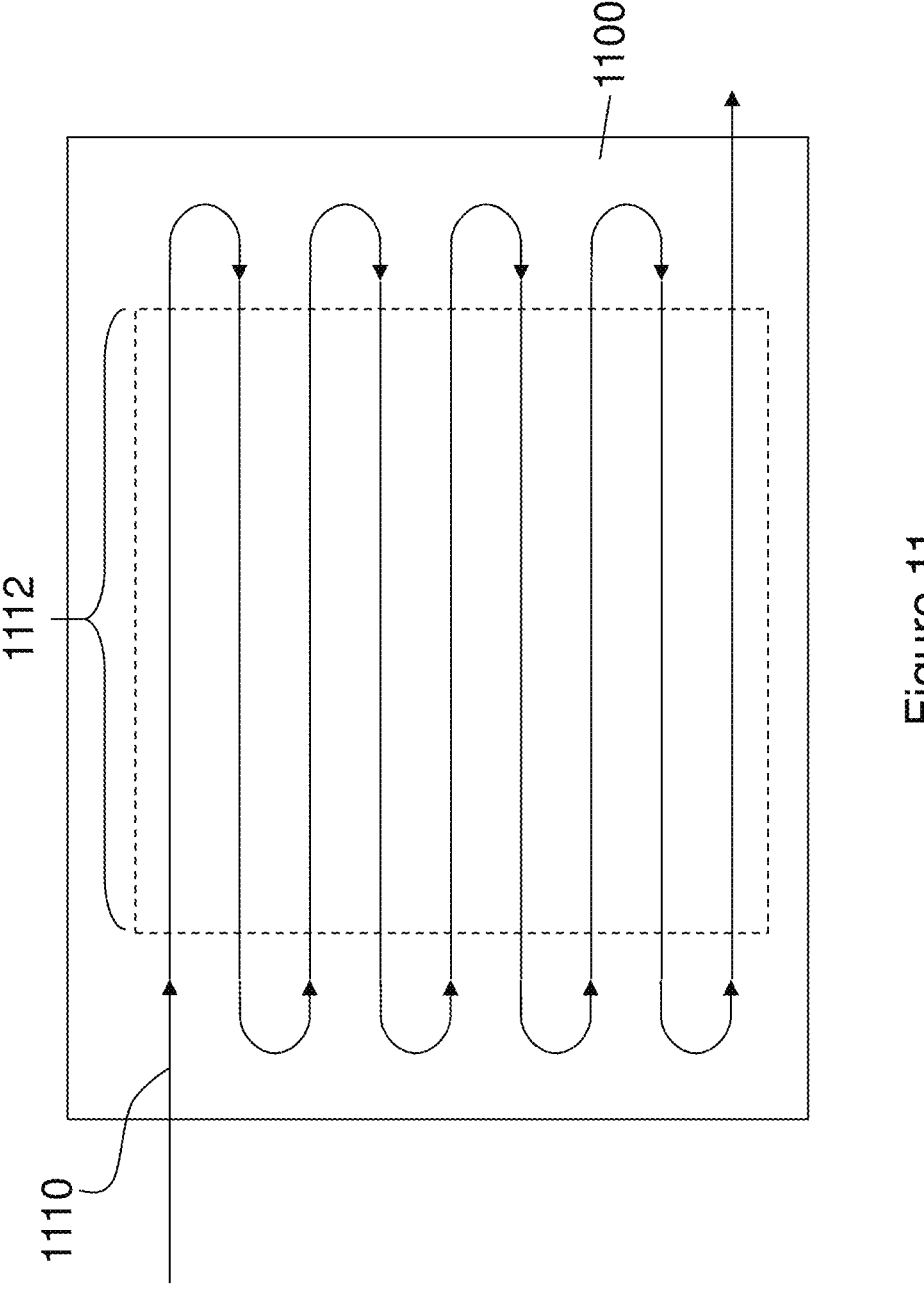
FIG. 11 schematically illustrates an example waveguide array in which the ends of the arrayed waveguides are connected.

FIG. 11 schematically illustrates an example waveguide array in which the ends of the arrayed waveguides are connected. As shown, substrate 1100 is provided comprising an originating waveguide 1110 that is not split, but rather passes repeatedly across a detection region 1112 in a serpentine arrangement. A plurality of reaction regions (not shown) are disposed proximal to originating waveguides 1110 within detection region 1112, all of which are illuminated by a single waveguide core. Although the embodiment in FIG. 11 has a single "serpentine" waveguide core and a single detection region, a single substrate can comprise one or more serpentine waveguide cores for illumination of one or more detection regions. Further, the serpentine waveguide arrangement can also be combined with other aspects of the present invention. For example, a serpentine waveguide can be tapered or otherwise modified (e.g., with respect to refractive index, depth, and the like) to promote even illumination over the detection region, as described elsewhere herein.

Waveguide Arrays Comprising Both Optical Splitter and Biosensing Portion on a Single Substrate The present invention provides waveguide arrays that perform both optical splitting and biosensing functions. For example, as described above, FIG. 4A provides a top view of one embodiment in which a first optical fiber 403 is optically coupled to an originating waveguide 404 disposed in substrate 402. Although FIG. 4A illustrates originating waveguide 404 being split into all six branch waveguides 406, 408, 410, 412, 414, and 416 using a T-splitter conformation, the splitting may also occur using a Y-branch splitter conformation, e.g., such that an originating waveguide is split into two branch waveguides, which are then each split to generate a total of four waveguides, two of which are then split for a total of six waveguides.

Waveguide arrays that perform both optical splitting and biosensing functions, while effective, present technical challenges involving, e.g., how optical energy is coupled into the waveguide array. For example, in certain preferred embodiments, free space laser light is coupled into input port(s) of waveguide(s), e.g., from the side of the substrate. The small modal profile of the coupled waves, however, can cause a portion of the input optical energy to be coupled into and propagated through the substrate. Where the optical energy is directed toward the detection region, this substrate-coupled optical energy can create unwanted background noise. Further, optical energy can also be lost from the waveguide cores during the splitting process, and such "scattered" optical energy in the substrate can also result in increased background noise, especially when the splitter is located near the detection region. The present invention provides alternative conformations or layouts of waveguide arrays comprising both optical splitters and biosensing regions that address these potential problems by mitigating or preventing such substrate-coupled background noise in the detection region of the substrate.

Figure 12:
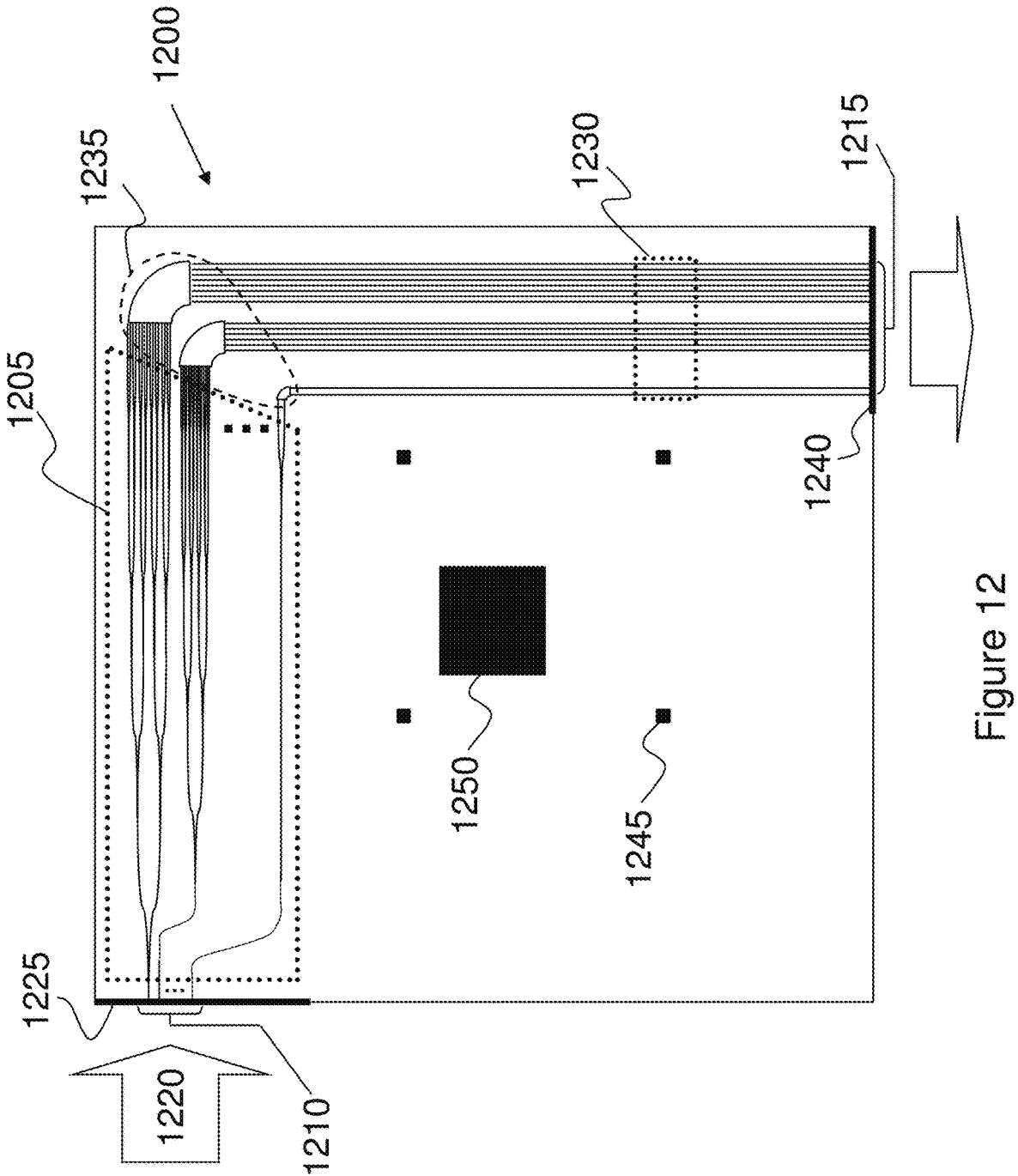
FIG. 12 provides an exemplary embodiment of a waveguide array that performs both optical splitting and biosensing functions.

FIG. 12 illustrates one specific embodiment of a waveguide substrate. Waveguide substrate 1200 comprises Y-branch splitter region 1205 that splits three originating waveguides 1210 into a total of 34 branch waveguides 1215 (2+16+16, although fewer are shown to simplify the illustration.) Optical energy 1220 is coupled into substrate 1200 at input end surface 1225, both into the cores of originating waveguides 1210, as well as into the matrix of waveguide substrate 1200 around originating waveguides 1210. To prevent increased background noise in biosensing region 1230 due to optical energy coupling loss at the inputs of originating waveguides 1210 (such as surface scattering, mode mismatching, etc.), branch waveguides 1215 are bent at a position upstream of biosensing region 1230, termed bend region 1235. The bend in the waveguides ensures that biosensing region 1230 is not in the path of optical energy 1220 that is coupled into the matrix of substrate 1200. After passing through biosensing region 1230, optical energy 1220 that remains in branch waveguides 1215 exits waveguide substrate 1200 at output end surface 1240. Although FIG. 12 shows a 90° bend in bend region 1235, bends of other angles can also be used to remove a biosensing region from the path of optical energy (e.g., excitation radiation) coupled into a waveguide substrate. For example, for an input coupling optics with 0.5 N.A. (numerical aperture), an envelope angle in a fused silica substrate is ~20 degrees. This envelope angle requires at least a 5.5 mm vertical offset between a biosensing region and a waveguide input ports, if the latter two are 15 mm apart horizontally. To satisfy this condition, the vertical offset can be chosen to be about 10 mm, e.g., in the layout in FIG. 12. Further, in certain preferred embodiments, waveguide substrate 1200 further comprises coarse and fine alignment marks to align an optical detection system with waveguide substrate 1200. For example, the small squares (e.g., 1245) and large square 1250 on substrate 1200 can be used as such alignment marks. In certain preferred embodiments, at least one alignment mark comprises silicon nitride and is about 2-5 mm².

In certain embodiments, a waveguide substrate such as that illustrated in FIG. 12 has horizontal dimensions on the order of 10-30 mm, and in certain preferred embodiment, such a waveguide substrate is approximately 20 mm². In certain embodiments, a portion of a waveguide core that is within a biosensing region is about 1-5 mm long. In certain embodiments, a biosensing region is about 1-10 mm wide. In certain embodiments, there is at least about 1-5 mm clearance between an edge of a waveguide substrate and the nearest branch waveguide. In certain embodiments, a biosensing region is about 2-10 mm from an output end surface and about 10-20 mm from an input end surface. In certain embodiments, dimensions are extended to or adjusted based upon a larger or smaller substrate, e.g. a 4, 6, or 8 inch substrate or "wafer" in which one or more biosensing regions are placed. Further, although FIG. 12 illustrates a configuration with a single bend region and a single biosensing region, the invention contemplates substrates with two or more bend regions and/or biosensing regions. Substrates comprising multiple reaction sites are described elsewhere herein, and include, e.g., arrays of nanoholes or zero-mode waveguides, and optionally integrated optical detection systems (e.g., lens arrays).

Waveguide Arrays Comprising Separate Optical Splitter and Biosensing Substrates

Waveguide arrays that perform both optical splitting and biosensing functions, while effective, present technical challenges involving, e.g., the fabrication of a single device that performs two disparate functions. Splitting optical energy from an originating waveguide into, e.g., 32 or more waveguides, using conventional Y splitters consumes space on the array, while it is preferable to allocate as much space as possible to the analytic, e.g., biosensing, portion of the array. For example, increasing the multiplex number, e.g., the number of analyte regions, disposed upon a waveguide array is technically challenging when a substantial portion of the array is occupied by features dedicated to splitting optical energy from an originating waveguide into a plurality of waveguides. New waveguide arrays that address this issue are therefore desirable.

The present invention provides devices comprising separate optical splitter and biosensing waveguide substrates. Such devices are advantageous for numerous reasons. For example, the performance of each waveguide substrate can be optimized through distinct fabrication processes. Further, the device has significant cost benefits as the optical splitter substrate is reusable, leaving the biosensing substrate as the only consumable waveguide substrate of the device.

Figure 13:
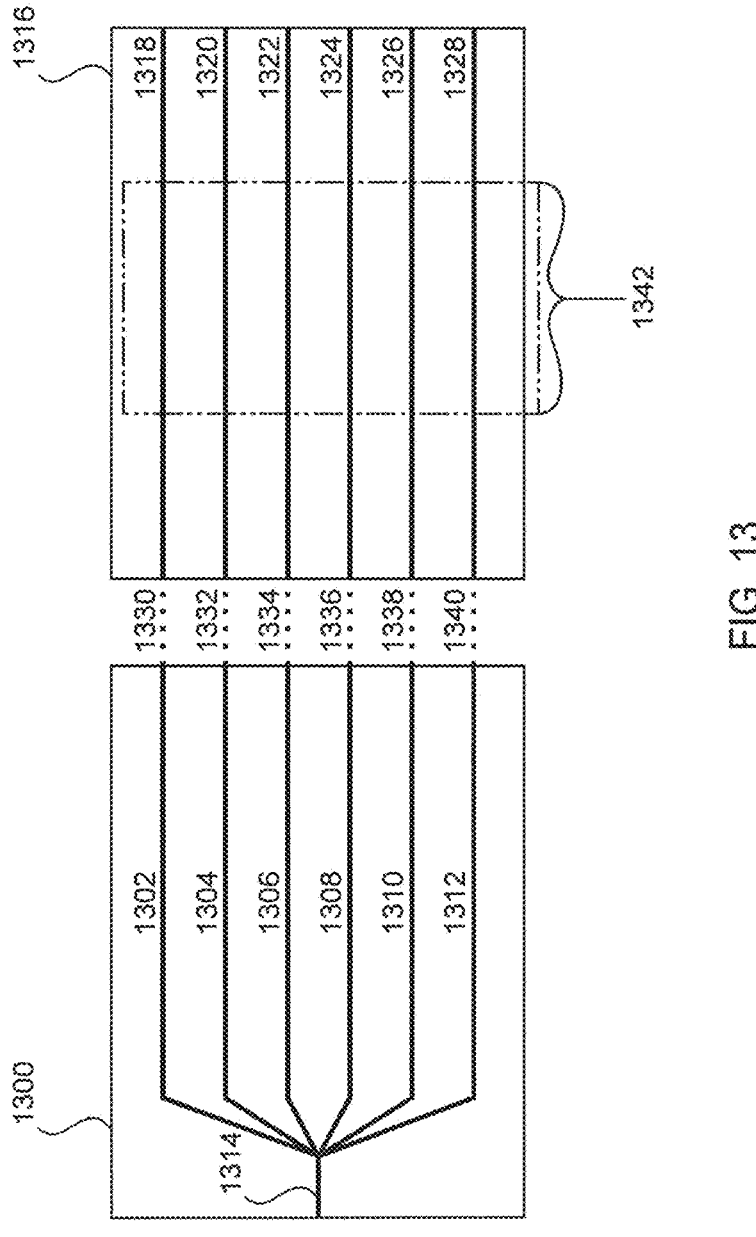
FIG. 13 schematically illustrates an analytic device that utilizes separate substrates for the optical splitting and biosensing functions of the device.

FIG. 13 schematically illustrates an example device comprising separate optical splitter and biosensor waveguide arrays for illuminating a plurality of analytes. As shown, first substrate 1300 is provided including a number of branch waveguides, e.g., surface-exposed branch waveguides 1302-1312. Branch waveguides 1302-1312 are optically coupled to a source of optical energy (not shown) via originating waveguide 1314. Second substrate 1316 is provided including a number of waveguides, e.g., surface-exposed waveguides 1318-1328. The waveguides of the second substrate 1316 are optically coupled to the branch waveguides of the first substrate 1300. As shown, waveguides 1318-1328 of the second substrate 1316 are optically coupled to branch waveguides 1302-1312 of the first substrate 1300 at coupling regions 1330-1340. Illumination of analytes is accomplished by disposing the analytes proximal to the waveguides of the second substrate 1316 within detection region 1342. It will be appreciated that branch waveguides of the first substrate and waveguides of the second substrate can be fewer or greater in number. For example, 32 or more branch waveguides of the first substrate and 32 or more waveguides of the second substrate are possible.

As will be appreciated, optical coupling between the branch waveguides of the first substrate and the waveguides of the second substrate can be accomplished by a variety of means. For example, optical coupling can be accomplished by fabricating the waveguides of the second substrate such that the cross-sectional area of the waveguides is greater at the optical coupling location, e.g., near the branch waveguides of the first substrate, than the cross-sectional area of the waveguides at a detection region of the second substrate. The greater cross-sectional area at the coupling location facilitates the entry of optical energy into the waveguides of the second substrate at the coupling location.

Numerous additional coupling mechanisms are available as well, e.g., disposing optical coupling elements, e.g., a lens or lenses, between the branch waveguides of the first substrate and the waveguides of the second substrate, such that optical energy exiting the branch waveguides of the first substrate is focused toward a receiving portion of the waveguides of the second substrate. Optical energy may also be coupled from the branch waveguides of the first substrate via an optical grating disposed within the waveguides of the second substrate at a position between the branch waveguides of the first substrate and the detection region of the second substrate. Coupling may be efficiently achieved by the use of Holographic Optical Elements (HOE's) which have the advantage of independent tenability for multiple wavelengths. Solid state devices can bye used for coupling such as programmable phase arrays that can provide adjustable coupling efficiencies that can be switched on/off and can also be tuned or adjusted to offset fabrication errors, wavelength shifts, various beam ualities, etc. Coupling can also be achieved by evanescent field modes, in which the waveguide structure is designed to overlap the guided modes of adjacent waveguides such that efficient coupling is achievable in a passive structure with less sensitivity to alignment errors than some other approaches. Other methods of coupling optical energy between waveguides are known to those of ordinary skill in the art, and includes but is not limited to the use of optical fibers.

In certain embodiments, a tapered core is used to improve the performance of a splitter substrate (or splitter portion of a substrate comprising both a splitter and biosensing portion), as well as the efficiency of coupling light from a waveguide with low confinement and a large modal profile (e.g., in a splitter substrate or portion) to a waveguide with high confinement and a small modal profile (e.g., in a biosensing substrate or portion). As described above, in certain embodiments a biosensing (or detection) region of a substrate preferably provides high refractive index contrast between the waveguide core and the waveguide cladding. Such an embodiment provides a desired level of illumination confinement in the substrate to provide optical waves having a modal diameter in the submicrometer or "few micrometer" range. In general, the thicker the waveguide, the smaller the modal profiles for optical waves passing through the waveguide. In contrast, a splitter substrate should preferably provide a low refractive index contrast between the waveguide core and waveguide cladding to promote uniformity of light being propagated from an input waveguide into multiple branch waveguides. As the size of a waveguide decreases, defects from the fabrication process (e.g., roughness of side walls of the waveguide core at the core-cladding interface) become relatively larger, and the performance of a splitter or fiber butt coupling is adversely affected, e.g., the splitting uniformity at a 1×2 splitter junction is compromised. As the size of the waveguide approaches the size of the defect, the adverse impact becomes greater. As such, a waveguide with high confinement has much higher propagation loss than a waveguide with low confinement, and this propagation loss can be reduced if the guided optical wave intensity at the interface can be lowered.

So, in certain preferred embodiments, the biosensing region/substrate is made with high refractive index contrast waveguides, and the splitter region/substrate is made with low refractive index contrast waveguides. However, the insertion loss into a waveguide with a small modal profile is relatively high, whether an input waveguide or a branch waveguide. The closer the modal profiles in the waveguide are to those in the fiber, the higher the coupling efficiency and, therefore, the lower the coupling loss. For example, in the case of input waveguides, the fiber to waveguide butt-to-butt coupling efficiency depends on the modal profile of the guided waves in the core. With regards to branch waveguides, a coupling between a low refractive index contrast waveguide (e.g., in a splitter region) and a high refractive index contrast waveguide (e.g., in a biosensing region) is expected to have a high degree of insertion loss. To mitigate this effect, waveguide cores can be tapered so that at the junction of the branch waveguides in the splitter region/substrate and the branch waveguides in the biosensing region/substrate the waveguide core dimensions are similar, thereby minimizing any insertion loss at the junction between the splitter region/substrate and the biosensing region/substrate. For example, the branch waveguides in a splitter region can be tapered to increase their dimensions to the dimensions of the core waveguides in the biosensing region/substrate. Alternatively or in addition, core waveguides in a biosensing substrate (e.g., preferably outside of the detection region) can be tapered to decrease their dimensions to the dimensions of the branch waveguides in the splitter region/substrate. The tapering can be fabricated in either or both the z and/or y direction.

Figure 14:
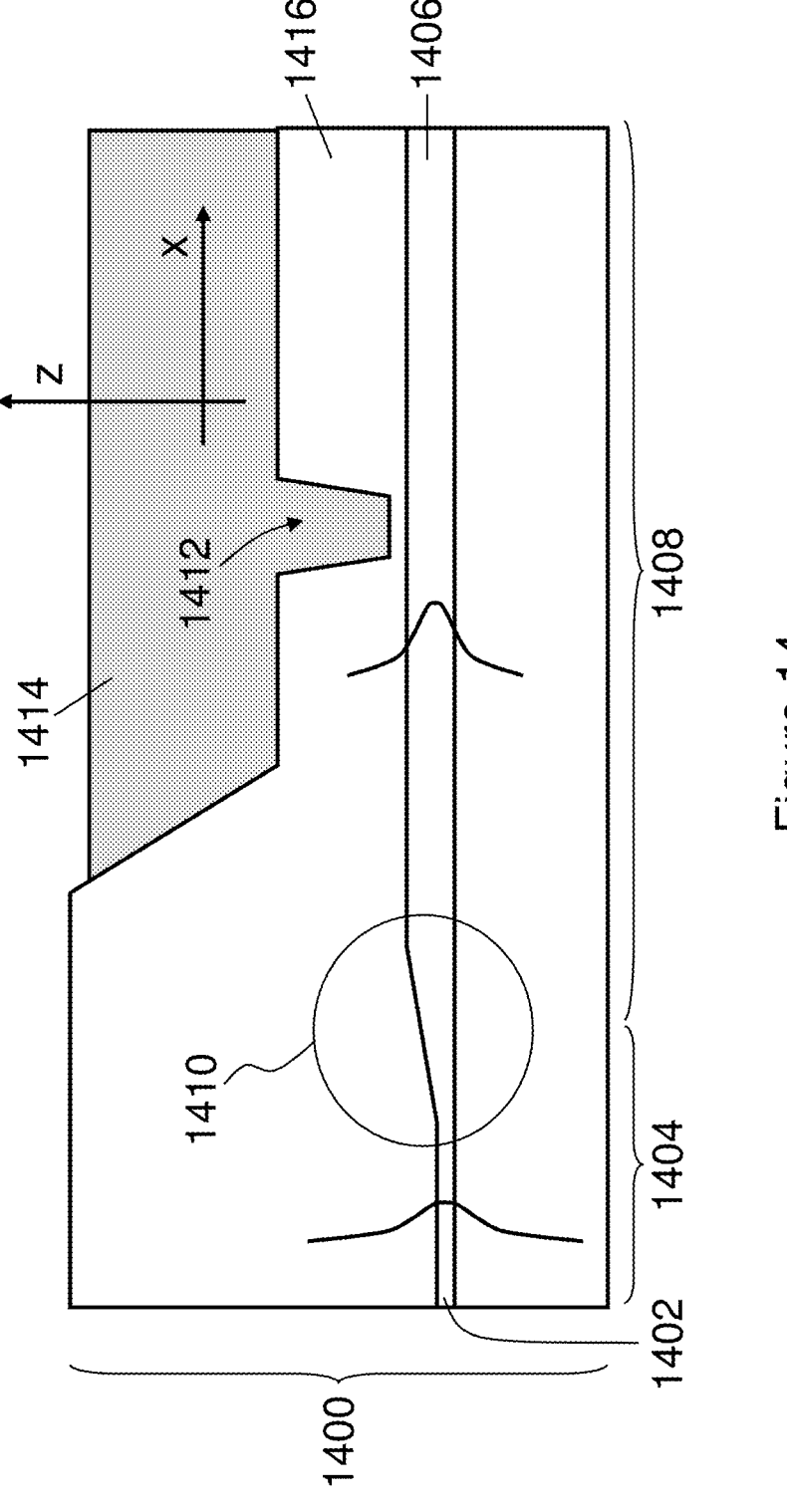
FIG. 14 provides an exemplary embodiment of a waveguide array comprising tapered waveguide cores in a splitter region of the substrate.

FIG. 14 provides an exemplary schematic cross-sectional view of one embodiment of a waveguide substrate 1400 comprising an originating waveguide core 1402 passing through a splitter region 1404 to create branch waveguide cores, e.g., branch waveguide core 1406 in a biosensing region 1408. Tapering of the originating waveguide core 1402 in the splitter region is shown at 1410. Nanohole 1412 is also shown in biosensing region 1408, where it is filled with a fluid volume 1414. The waveguide cladding 1416 is thickest above the less restrictive originating waveguide core 1402, e.g., in the input and splitter regions 1404, and is thinnest above the more restrictive branch waveguide core 1406, e.g, in the biosensing region. This difference in cladding thickness mitigates loss of optical energy into the fluid volume 1414, which helps reduce background noise. Various modifications to this exemplary embodiment are also contemplated, such as combinations with other modifications described herein and known to those of ordinary skill in the related fields.

Waveguide Arrays with Decreased Bulk Fluorescence and Propagation Losses Due to Back Reflection When a plurality of nanoholes are disposed through a translucent mask layer and proximal to a surface-exposed waveguide in a substrate, the nanoholes become scattering sources within the waveguide. In certain applications where fluorescent dye-containing solutions are disposed over the substrate, scattered light can penetrate through the translucent mask layer of the substrate and enter the well containing the fluorescent solution, creating bulk fluorescence. This bulk fluorescence noise can exceed the fluorescent signals of interest within the analyte regions, thereby mitigating the effectiveness of the waveguide substrate. Further, when analyte regions, e.g., in nanoholes, of uniform spacing are disposed proximal to a waveguide core, the nanoholes can create grating effects that result in back reflection in the waveguide core. This back reflection can result in propagation losses within the waveguide core.

The present invention provides waveguide substrates that decrease the amount of scattered light that penetrates beyond the mask layer through which nanoholes are formed, and optionally reduce the grating effects that result from uniformly disposing nanoholes proximal to the waveguide. The waveguide substrates provided by the invention can include a top mask cladding layer, e.g., a cladding layer disposed upon a mask layer that is impenetrable to light such that nanoholes can be formed through both the cladding and mask layers. At locations along the waveguide where nanoholes are absent, the top mask cladding layer prevents scattered light from penetrating beyond the top surface of the device, thereby mitigating bulk fluorescence that results from the scattered light.

Waveguide substrates of the present invention also address issues of back reflection in the waveguide core. When nanoholes are uniformly spaced through a mask layer adjacent to a waveguide, the uniformly spaced nanoholes can create grating effects that cause back reflection in the waveguide core. This back reflection results in propagation losses that adversely affect the performance of the device. The present invention provides waveguide substrates in which the nanoholes exhibit non-uniform spacing, e.g., exhibit a random spacing error, to substantially eliminate these grating effects.

Figure 15:
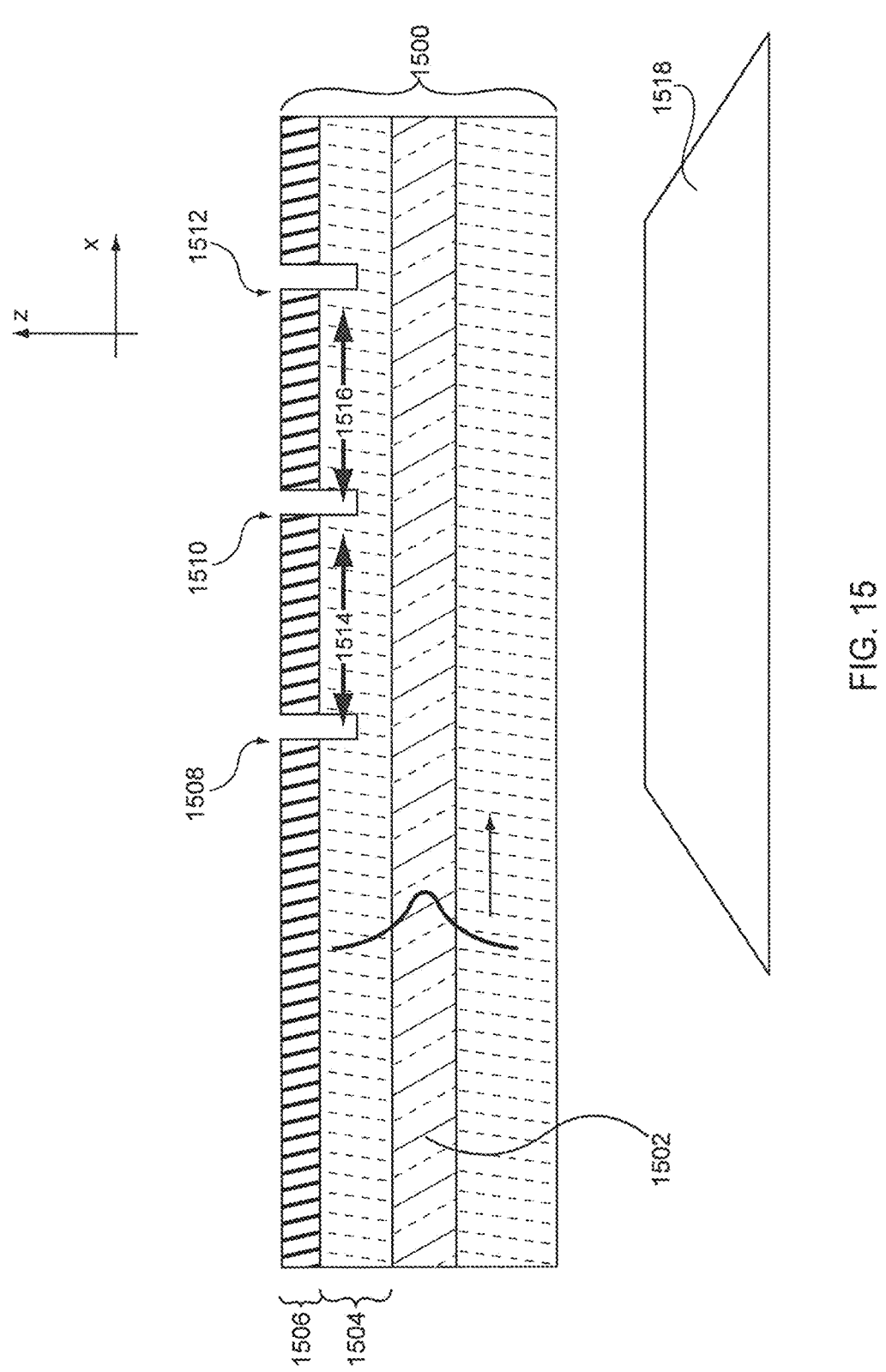
FIG. 15 schematically illustrates a device that utilizes a mask cladding layer to reduce scattering of optical energy beyond a top surface of the device.

An example waveguide substrate for reduced bulk fluorescence and decreased back reflection is schematically illustrated in FIG. 15. As shown in cross-section, substrate 1500 is provided including a number of waveguides, e.g., waveguide 1502. Mask layer 1504 is disposed upon the layer of the substrate comprising waveguide 1502. Mask cladding layer 1506, e.g., a metal layer (e.g., aluminum or chromium), is disposed over mask layer 1504. Apertures, e.g., nanoholes 1508, 1510 and 1512, are formed through mask cladding layer 1506 and mask layer 1504, such that a portion of nanoholes 1508-1512 is at or near the top surface of, and can be illuminated by an evanescent field emanating from, waveguide 1502. The illumination of analytic processes within the apertures permits the observation of such processes by detection system 1518.

In the case of top cladding layers made of metal, deposition may be accomplished through a number of means, including evaporation, sputtering, spin-coating, chemical vapor deposition or the like. Such processes are described in, e.g., U.S. Pat. No. 7,170,050, previously incorporated herein by reference in its entirety.

To reduce grating effects that cause back reflection in the waveguides, the spacing between apertures, e.g., distance 1514 between apertures 1508 and 1510 and distance 1516 between apertures 1510 and 1512, optionally exhibit a random spacing placement offset, e.g., at least about a 1%, 3%, or 5% random spacing placement offset, as compared to apertures with uniform spacing. Essentially, the pitch is modified to decrease the coherent coupling between the apertures that normally result in back reflection into the core. Typically, a decrease of at least about 3-20 dB is sufficient, and it is well within the skill of the ordinary practitioner to determine an appropriate waveguide device, e.g., based on the characteristics of the waveguide (e.g., chemical composition, dimensions, etc. of core, cladding, and apertures) and the optical energy being propagated therein (intensity, wavelength, mode structure, etc.).

Waveguide Arrays with Greater Confinement of Fluorescence Emission Angle from Nanoholes The fluorescent signal emission from a labeled reaction component at the bottom of a nanohole in a waveguide substrate has broad angular distribution and emits no only toward the bottom of the substrate, but also toward the top. An objective lens (e.g., of an optical train) can be positioned to collect signal emissions going in a given direction, e.g., toward the bottom of the substrate, but in a single lens system those going in the other direction are not collected. It would be beneficial to increase the amount of signal collected by the optical system, e.g., by increasing the amount of signal directed toward the optical train. Further, by confining the angular distribution of the signal, an objective lens with a smaller numerical aperture (N.A.) can be used, which can also increase the multiplex capabilities of the system. The present invention provides waveguide substrates that increase the percent of fluorescent signal emissions that are directed toward the optical train, thereby increasing the peak intensity of the detected signal.

Figure 16:
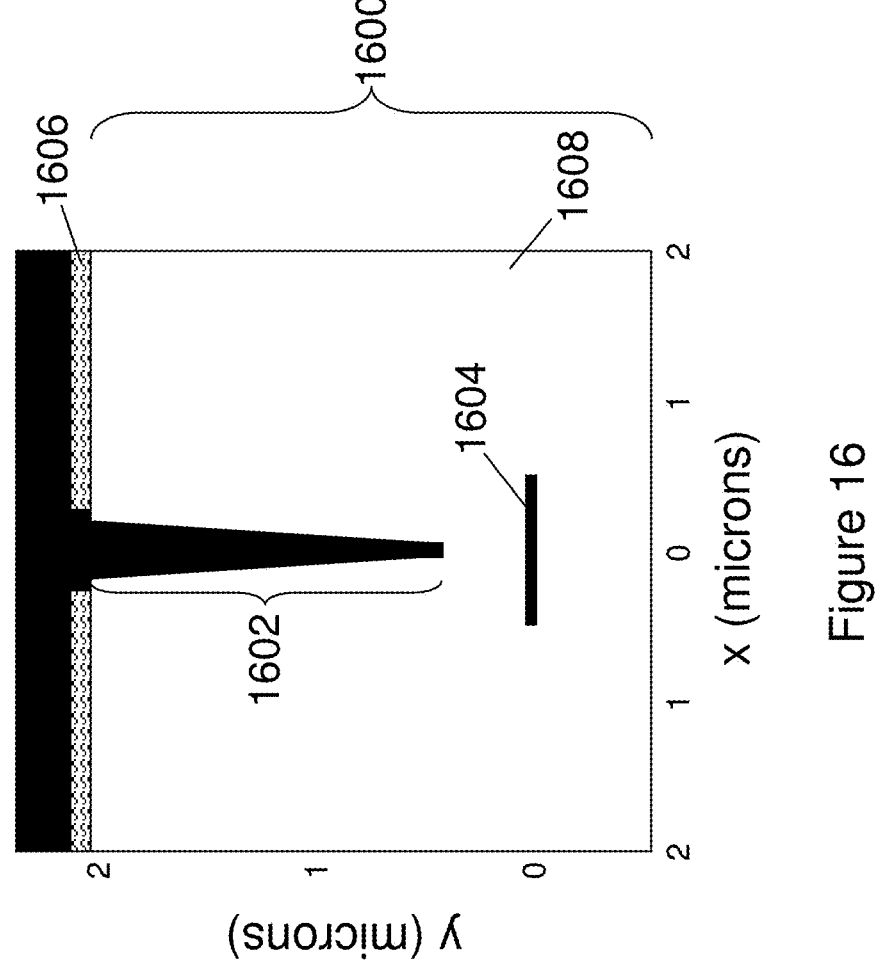
FIG. 16 illustrates a cross-section of an exemplary waveguide substrate comprising a metal layer disposed on a top surface of a waveguide cladding layer.

In certain preferred embodiment, a metal layer placed on top of the waveguide cladding serves to reflect upward directed photons back toward the bottom of the substrate. FIG. 16 illustrates a cross section of such a waveguide substrate 1600 through a tapered nanohole 1602 and channel waveguide core 1604. A metal layer 1606 is shown upon the surface of the waveguide cladding. In this embodiment, the nanohole 1602 penetrates the waveguide cladding 1608, but does not penetrate the channel waveguide core 1604. In preferred embodiments, the submicrometer opening at the top of the nanopore is of a subwavelength diameter to reduce or prevent light passing from the observation volume through this aperture to the area above the substrate and metal layer. In preferred embodiments, the metal layer need only be thick or opaque enough to reflect light down into the substrate, e.g., about 40 nm to about 250 nm, or about 100 nm thick. Various types of metal can be used in the layer, including but not limited to aluminum, gold, platinum, silver, chromium, and combinations thereof.

Detailed finite-difference time-domain (FDTD) simulations show that the angular emission from a fluorophore at the bottom of the nanohole can be confined by the presence of the aluminum layer on the top of the substrate, thereby increasing the proportion of photons that can be captured with a single objective positioned below the substrate relative to an objective with an identical numerical aperture below a substrate lacking the aluminum layer. The simulations show that the emission angles are more confined within smaller cones for dipoles polarized along either the x or z direction (directions parallel to the top of the substrate). For dipole emitters lined up along the y direction, less angular confinement is provided by the addition of an aluminum layer. Thus, deposition of a reflective layer (such as aluminum) above the top cladding layer of a waveguide chip will enhance the fluorescence emission intensity and confine the angular distribution. As such, although autofluorescence noise from the waveguide core may be somewhat higher, the benefits in increased emission intensity and confinement of the angular distribution are expected to more than compensate for any increased background noise.

Waveguide Arrays with Improved Illumination Efficiency

When a plurality of nanoholes are disposed on a substrate and filled with a fluid (e.g., reaction mixture), the change in refractive index at the nanoholes can perturb the propagation of the optical waves in the waveguide, and a large portion of the light can be scattered in undesirable directions. The present invention provides waveguide arrays that reduce such scattering of propagating light by including "dummy nanoholes" spaced closer than the wavelengths of optical waves propagating within the waveguide core.

Figure 17:
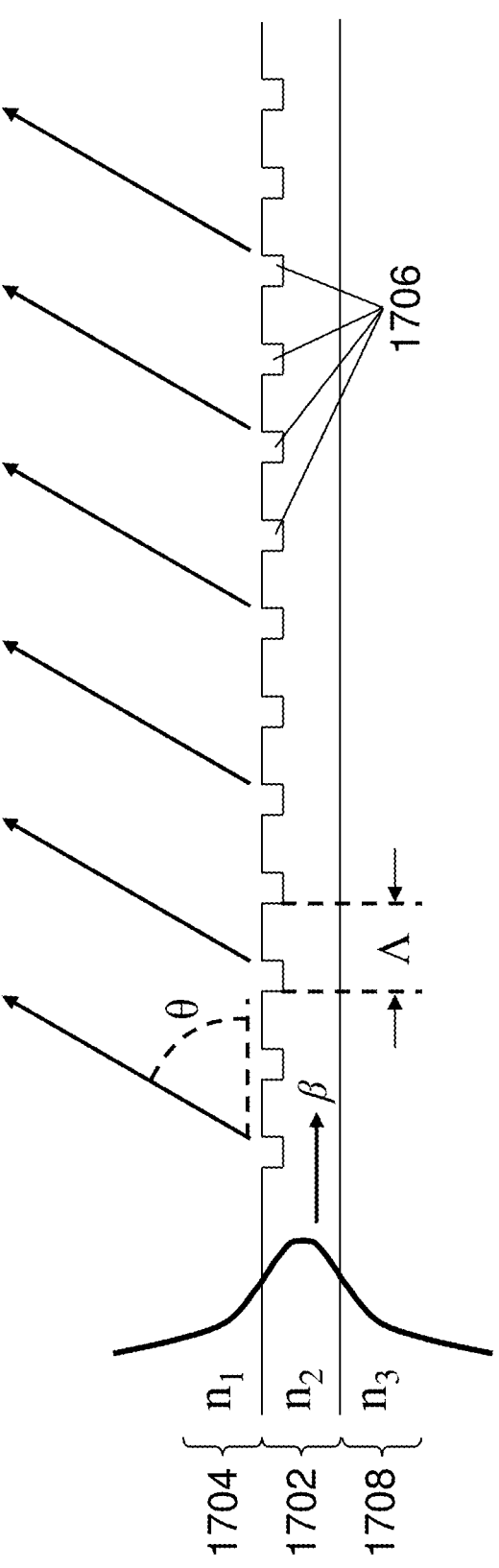
FIG. 17 provides a longitudinal phase matching diagram illustrating a corrugated waveguide output coupler.

The scattering properties of a waveguide optically coupled to an array of nanoholes can be described as an output coupler that couples a guided confined mode with a propagation constant β to a radiation mode. FIG. 17, a longitudinal phase matching diagram illustrating corrugated waveguide output coupler, shows the radiation mode escapes from a waveguide core 1702 having a refractive index $n_2$ at an angle θ into a semi-infinite upper layer 1704 having a refractive index $n_1$. For radiation mode into the upper layer 1704, the grating period Λ must satisfy Equation 1:

$$\beta - \frac{\omega n_1}{c}\cos\theta = l\frac{2\pi}{\Lambda},$$
$$l = \pm 1, \pm 2, \dots.$$

Using the relationship β=2π/λg and λ=c/f, the above equation can be rewritten as Equation 2:

$$\cos\theta = \frac{n_2}{n_1} - \frac{l}{\Lambda}\cdot\frac{\lambda}{n_1},$$
$$l = \pm 1, \pm 2, \dots.$$

To have a valid solution for Equation 2, the pitch of the grating or the pitch of the nanoholes (e.g., 1706) must satisfy Equation 3:

$$\Lambda \ge \frac{\lambda}{n_2 - n_1}$$

where the equal sign corresponds to the case θ=0, or the free space radiation mode propagates along the direction of the guided mode.

For radiation mode into the semi-infinite lower layer 1708 having a refractive index $n_3$, using the same derivation as above, the pitch of grating must satisfy the following condition to have a radiation mode (Equation 4):

$$\Lambda \ge \frac{\lambda}{n_2 - n_3}$$

For example, the effective refractive indices of a waveguide with nanoholes are $n_1$=1.33, $n_2$=1.53, $n_3$=1.46. For guided optical waves at 532 nm, the minimum pitches that can generate free space radiations into either the upper or the lower layers are 2.66 µm and 7.6 µm, based on Equation 2 and Equation 4, respectively.

The nanoholes extending into a waveguide substrate act as a periodical structure that couples light out into the upper or lower layers. To suppress the free space radiation modes from nanoholes, the pitch of the nanoholes is made smaller than the numbers calculated based on Equation 3 and Equation 4. If the pitch of the nanoholes is smaller than the resolving power of the imaging optics, dummy nanoholes with identical refractive index can be made to suppress the scattering effects. Using the 532 nm mode example calculation above, if the optical resolution of the imaging optic is 4 µm, nanoholes can be constructed with 2 µm spacing and every other nanoholes can be rendered inaccessible to analytes by filling them with material having a refractive index identical to that of the fluid that will be introduced to the other half of the nanoholes.

It will be readily understood by one of ordinary skill in the art that the examples provided above are for small refractive contrast waveguide structures. The minimum pitches are much smaller (subwavelength) for waveguide structures with much higher contrasts. For further information on periodic structures in integrated optics, see Yariv, et al. (1977) "Periodic Structures for Integrated Optics," IEEE Journal of Quantum Electronics, Vol. QE-13, No. 4, the disclosure of which is incorporated by reference herein in its entirety for all purposes.

Waveguide Arrays with Improved Analyte Immobilization Properties

The waveguide arrays of the invention include analyte regions that optionally include one or more analytes disposed within the analyte regions. For reliable observation of the analyte by a detection system, it is preferable to immobilize the analyte to a surface of the substrate that is in sufficient proximity to a waveguide core such that the analyte is illuminated by an evanescent field emanating from the waveguide core. Targeted immobilization to a surface of a waveguide array proximal to a waveguide, e.g., proximal to an exposed surface of a waveguide, such that self-alignment of the analytes with the waveguide pattern is achieved, e.g., a near-perfect array of detection spots, is particularly desirable.

Figure 18:
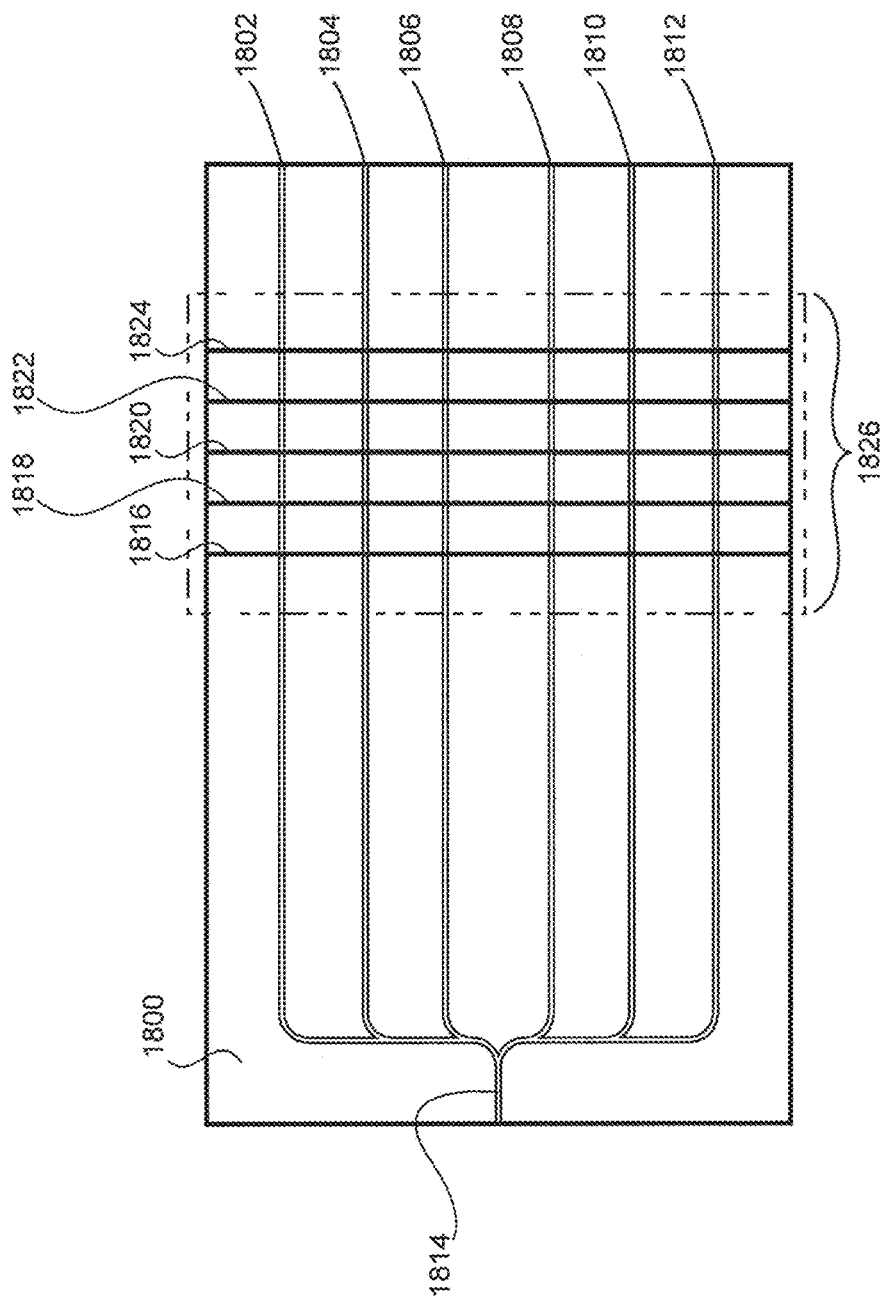
FIG. 18 schematically illustrates a device for immobilizing a plurality of analytes proximal to waveguides disposed upon or within a substrate of the device.

A device of the present invention is schematically illustrated in FIG. 18. Substrate 1800 is provided, including one or more waveguides, e.g., surface-exposed waveguides 1802, 1804, 1806, 1808, 1810 and 1812, which are optically coupled to originating waveguide 1814. An array of substantially parallel lines of a surface immobilization compound, e.g., lines 1816, 1818, 1820, 1822 and 1824 are deposited upon substrate 1800 such that lines 1816-1824 are substantially perpendicular to waveguides 1802-1812. In preferred aspects, lines 1816-1824 are deposited upon substrate 1800 such that the lines are deposited upon a top surface of waveguides 1802-1812. A mask layer (not shown) can be provided, such that only the intersections between lines 1816-1824 and top surface of waveguides 1802-1812 are exposed. Analytes (not shown) with an affinity for the particular material from which the lines are made, e.g., a metal (e.g., gold), is then provided and immobilized at the intersection of lines 1816-1824 and top surface of waveguides 1802-1812.

Deposition can be accomplished by a variety of methods, e.g., microcontact printing. Alternatively, the metal lines can be deposited, and biased chemistry can be used to situate the analytes on the lines and not in the spaces in between.

Optical Trains and Detection Systems

Optical trains and detection systems for use in carrying optical energy (e.g., illumination) to and/or collecting emitted optical energy from an analyte region disposed on a waveguide substrate of the invention generally include an optical energy source, e.g., one or more lasers, a waveguide to provide optical energy to one or more analyte regions, an optical train that transmits emissions so that they can be detected and analyzed, and detection and data processing components for detecting, storing and presenting signal information. For example, certain embodiments of optical systems useful with the waveguide substrates provided herein include those described in U.S. Patent Publication No. 2008/0128627, which is incorporated herein by reference in its entirety for all purposes. Other optical trains and detection systems for use with waveguide substrates are known to those of ordinary skill in the art, and are provided, e.g., in U.S. Provisional Patent Application No. 61/223,628, filed Jul. 7, 2009; U.S. Pat. Nos. 6,437,345, 5,677,196, and 6,192,168; U.S. Patent Publication Nos. 2002/0146047, 2007/0188746, 2007/0036511, 2005/0175273, and 2008/0030628; and in various publications, including Bernini, et al. (2005) Proceedings of SPIE, Vol. 5728:101-111; Boriarski, et al. (1992) Proceedings of SPIE, Vol. 1793:199-211; Feldstein, et al. (1999) Journal of Biomedical Microdevices, Vol. 1:139-153; Herron, et al. (2003) In: Biopolymers at Interfaces, $2^{nd}$ Edition (M. Malmsten, Ed.), Surfactant Science Series, Vol. 110, Marcel Dekker, New York, pp. 115-163; and Weissman, et al. (1999) Proceedings of SPIE, Vol. 3596:210-216, the disclosures of which are incorporated herein by reference in their entireties for all purposes. In particular, in certain aspects, the imaged signal will be a series of discrete signal sources or points of signal origin on the overall surface of the waveguide substrate. As such, in certain aspects the detection systems described in the aforementioned applications are directly applicable to the present invention.

Figure 19:
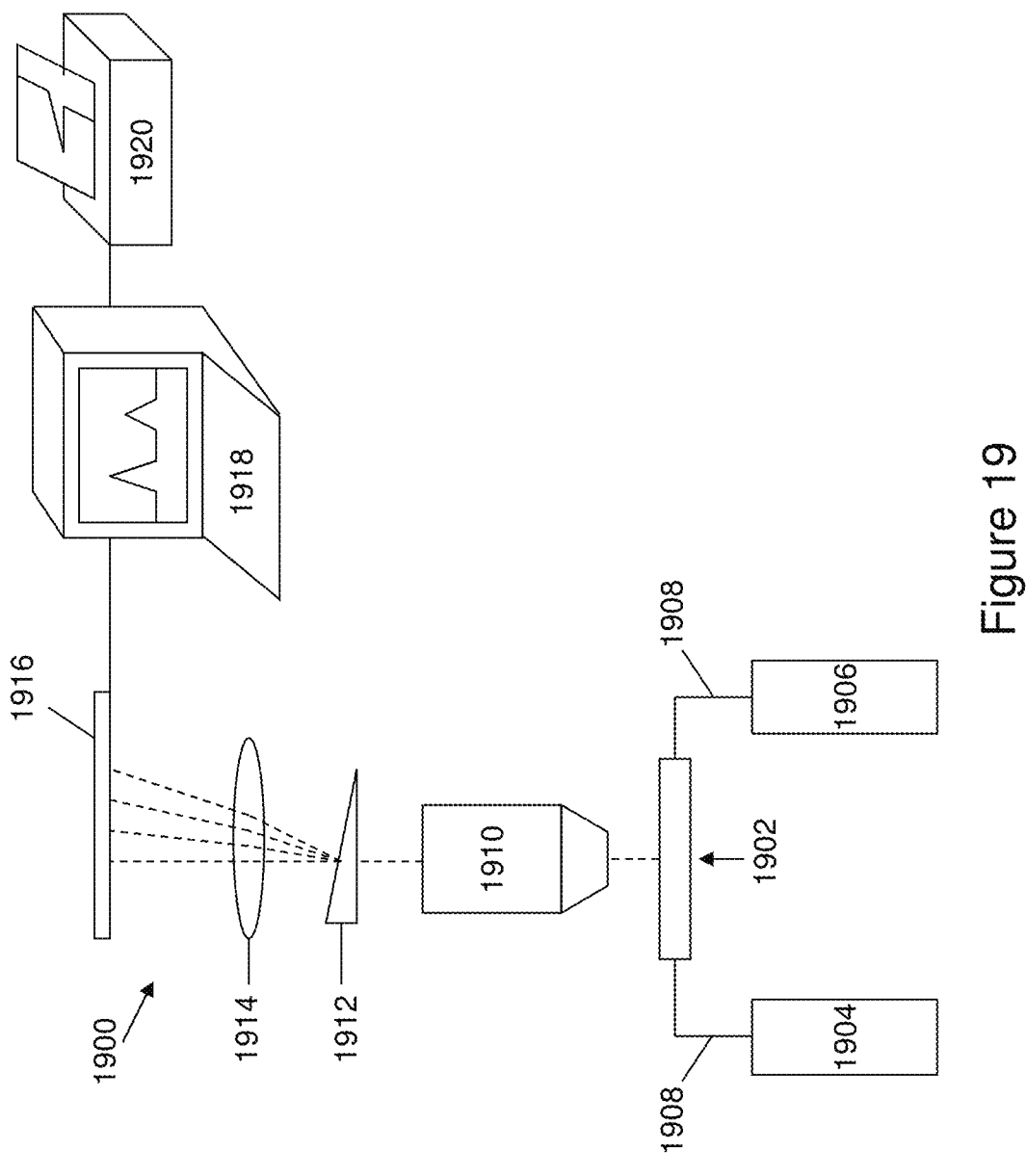
FIG. 19 provides one example of a system for use in the present invention that includes an optical train and detection system.

One example of a system for use in the present invention is illustrated in FIG. 19. As shown, the system 1900 includes a waveguide substrate of the invention 1902. Laser 1904 and optional additional laser 1906 are optically coupled to one or more waveguides within the substrate, e.g., via optical fibers 1908. An optical train is positioned to receive optical signals from the substrate and typically includes an objective 1910, and a number of additional optical components used in the direction, filtering, focusing and separation of optical signals. As shown, the optical train includes a wedge prism 1912 for separating spectrally different signal components, and a focusing lens 1914 that images the signal components upon an array detector, e.g., EMCCD 1916. The detector is then operatively coupled to a data storage and processing system, such as computer 1918 for processing and storage of the signal data and presentation of the data in a user desired format, e.g., on printer 1920. As will be appreciated, a number of other components may be included in the systems described herein, including but not limited to mirrors, gratings, switches, and optical filters for filtering background illumination or bleed-through illumination from the optical energy sources, from the actual optical signals. Additionally, alternate optical trains may employ cascaded spectral filters in separating different spectral signal components.

While illustrated with a first optical energy source, e.g., laser 1904, and an optional second optical energy source, e.g., optional laser 1906, it will be appreciated that additional optical energy sources may be provided optically coupled to the waveguide substrates, e.g., using additional originating waveguides to direct light from each the various sources to all or a subset of the waveguides in a given waveguide array. For example, in some cases, 3 light sources, 4 light sources or more may be used. Additional light sources will preferably provide light having different spectral characteristics, e.g., peak wavelengths, to the waveguides, although they may also be employed to provide additional intensity or variations in other light characteristics, such as frequency.

While illustrated with an optical fiber coupling, optical energy can also be coupled into the waveguide by other means, e.g., using a free-space methodology. For example, optical energy can be coupled into a waveguide substrate at an edge of the substrate. In certain preferred embodiments, such optical energy is directed at the end of one or more waveguides and coupled therein. In other embodiments, the optical energy is instead coupled into the waveguide substrate from the side of the substrate rather than being directed at the ends of the waveguides. In either case, coupling can be achieved through the use of a grating or butt coupling, both of which are routine in the art.

The detection system is typically configured to detect signals from large areas of the waveguide substrate, e.g., multiple signals emanating from a plurality of different analyte regions on the substrate, and preferably, do so simultaneously. Thus while scanning detection optics may be employed for certain applications of the invention, in general, larger area imaging detection systems are preferred.

In certain embodiments, there are a plurality objective lenses in an optical system of the invention. For example, one or more objective lenses may be positioned below the waveguide array and/or one or more objective lenses may be positioned above the waveguide array. Such multiple objective configurations are useful for both increasing the collection efficiency and multiplex capabilities of the system.

Figure 20:
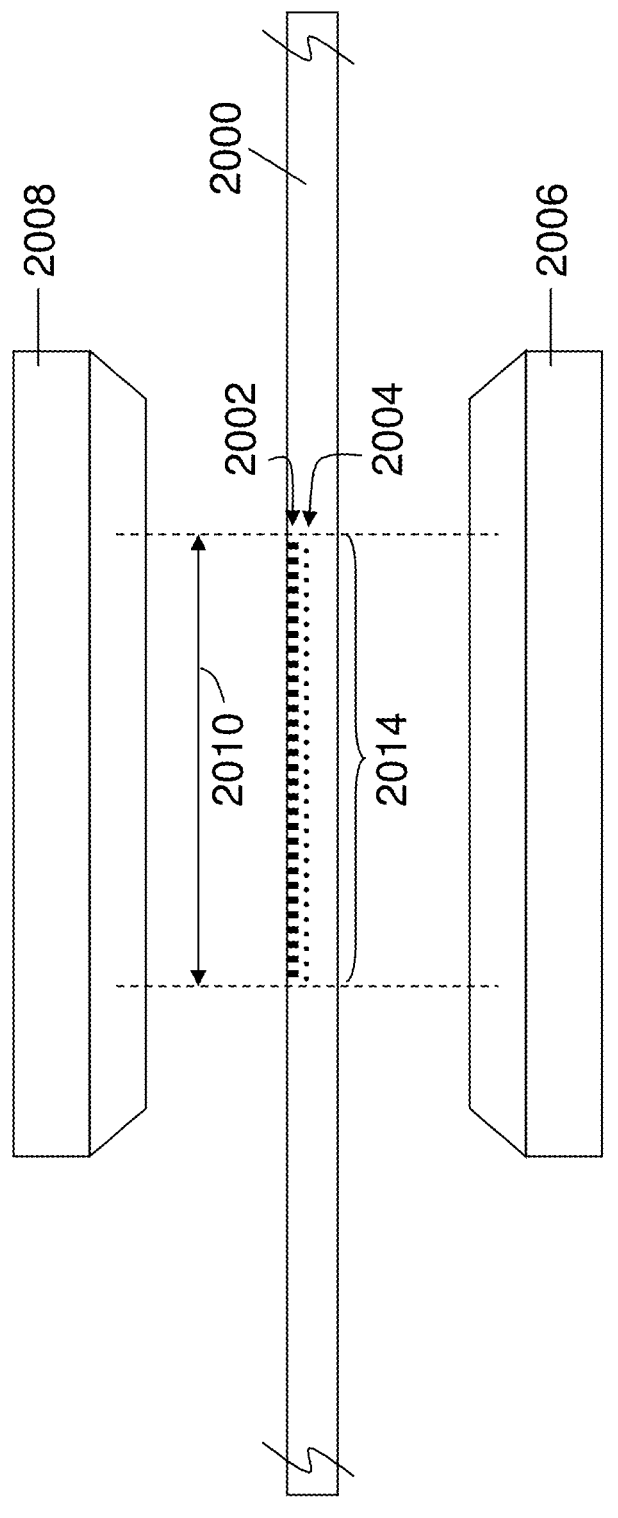
FIG. 20 provides an illustrative example of a device comprising a waveguide substrate and two objective lenses flanking a single detection region.

As described above in the section entitled "Waveguide Arrays with Greater Confinement of Fluorescence Emission Angle from Nanoholes," if a single objective lens is positioned under the waveguide substrate, signal emissions that emerge from the top of the substrate are not collected. In certain embodiments, a plurality of objective lenses are used to mitigate the resulting loss of signal and thereby increase collection efficiency. An illustrative example of such an embodiment is provided in FIG. 20, which depicts a cross-section of a waveguide substrate 2000 having nanoholes 2002 and channel waveguides 2004. Two objective lenses are used: a first objective lens 2006 positioned under the waveguide array to collect signal emissions that are directed toward the bottom of the substrate 2000, and a second 2008 positioned above the waveguide array to collect signal emissions that are directed toward the top of the substrate 2000. The two objective lenses (2006 and 2008) have the same field-of-view (FOV) delineated by the double-arrow 2010, and this FOV defines the detection region 2014. The emission signals collected by these two objective lenses can be combined with standard optical train components to be directed to a single detector (e.g., camera), or may be detected separately, e.g., using two detectors. A two camera system allows cross-correlation between signal detected at the top and bottom of a given nanohole, and the additional data so generated can increase the accuracy of the system. Statistical analyses for processing signal data including cross-correlations are well known to the ordinary practitioner and routinely practiced in the art.

Figure 21:
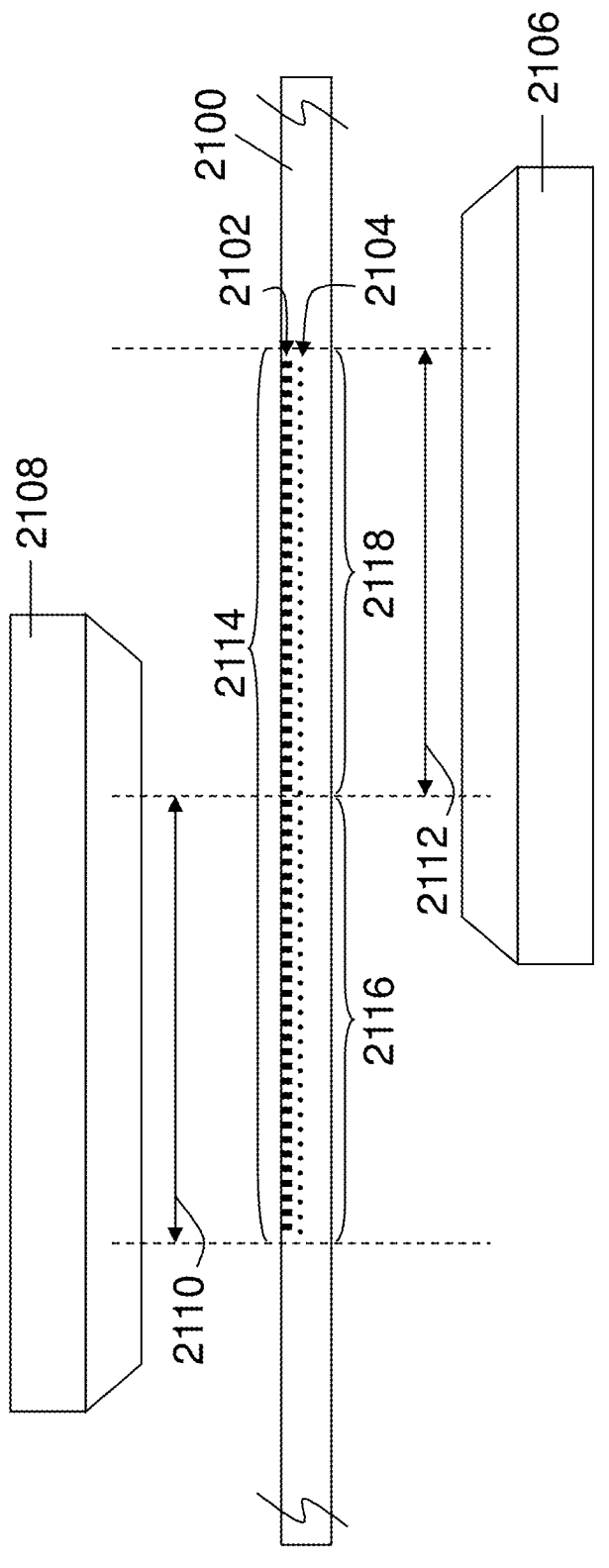
FIG. 21 provides an illustrative example of a device comprising a waveguide substrate and two objective lenses, each of which collects signals from a discrete detection region.

Additional benefits can also be realized by a multi-objective configuration. One advantage to waveguide illumination is that the illumination light is confined near the vicinity of the focal plane of the imaging optics, so autofluorescence does not tend to scale with the multiplex number, which facilitates observation of higher numbers of reactions on a single substrate ("higher multiplex") as compared to other types of illumination that are more prone to autofluorescent background signals. However, the collection optics can limit the extent of multiplex detection on a waveguide substrate. For example, in a single objective lens system a detection region on a substrate can be limited to the size of the FOV of the objective lens. To increase the multiplex, a custom objective lens may be designed and constructed to image a larger field-of-view, but such design and construction are both time-consuming and expensive. A more economical solution provided by the instant invention is to double the multiplex by using two separate off-the-shelf objective lenses, which are less expensive and more readily available than a custom objective lens would be. An illustrative example of such an embodiment is provided in FIG. 21, which depicts a cross-section of a waveguide substrate 2100 having nanoholes 2102 and channel waveguides 2104. As for the double lens system described above, there is one objective 2106 positioned under the waveguide substrate and a second objective 2108 positioned over the waveguide substrate. However, in contrast with the two objective lens system described above, the objective lenses 2106 and 2108 are not aligned on top of each other, but rather offset from one another so that each detects emissions from a different portion of the detection region 2114. For example, the first objective 2106 has an FOV delineated by the double arrow 2112, and so collects signal from a first half of the detection region 2118, and the second objective 2108 has an FOV delineated by the double arrow 2110, and so collects signal from a second half of the detection region 2116. As such, an area with twice the FOV of each individual objective lens can be monitored and imaged, one FOV by the objective positioned at the bottom of the substrate, and one FOV by the objective positioned at the top of the substrate. Alternatively or in addition, more than one objective lens could be positioned on the same side of the substrate, e.g., if the substrate comprised more than one discrete and separate detection region and they were positioned within the FOVs of the adjacent objective lenses, e.g., given the size of the lens housings and any other structures required to position the lenses. Further, an array of objective lenses could be used to detect signal from a large single detection region, with some objective lenses above the substrate and some below, so long as the FOVs of the arrayed lenses covered the entire detection region. As such, using two objectives can thereby increase the multiplex number by two-fold as compared to only one objective, and each additional objective on the top or bottom of the substrate can provide another fold-increase in the multiplex capabilities of the system. Further, by using off-the-shelf objective lenses rather than large, expensive custom lenses, a cost savings is realized, as well.

In certain preferred embodiments, one or more microlens arrays are components of an optical system that is integrated into a device for single-molecule (e.g., single-reaction-site) detection. In certain aspects, such a device is a single unit that contains multiple layers: a substrate comprising one or more nanoholes or ZMWs, lens arrays, gratings (e.g., Fresnel wedge gratings), and sensors. One or more nanoholes or ZMWs may optionally be disposed within a confinement on the surface of the substrate, e.g., a well or channel. In typical implementation, the layers of the device are fabricated separately by different process that achieve the specific specification requirements for each layer. After fabrication, the layers are aligned with one another during assembly of the device. Manufacture and precise alignment of the layers can be achieved by known methods, e.g., based on conventional semiconductor or microarray fabrication processes, and so are within the level of one of ordinary skill in the art.

Figure 22:
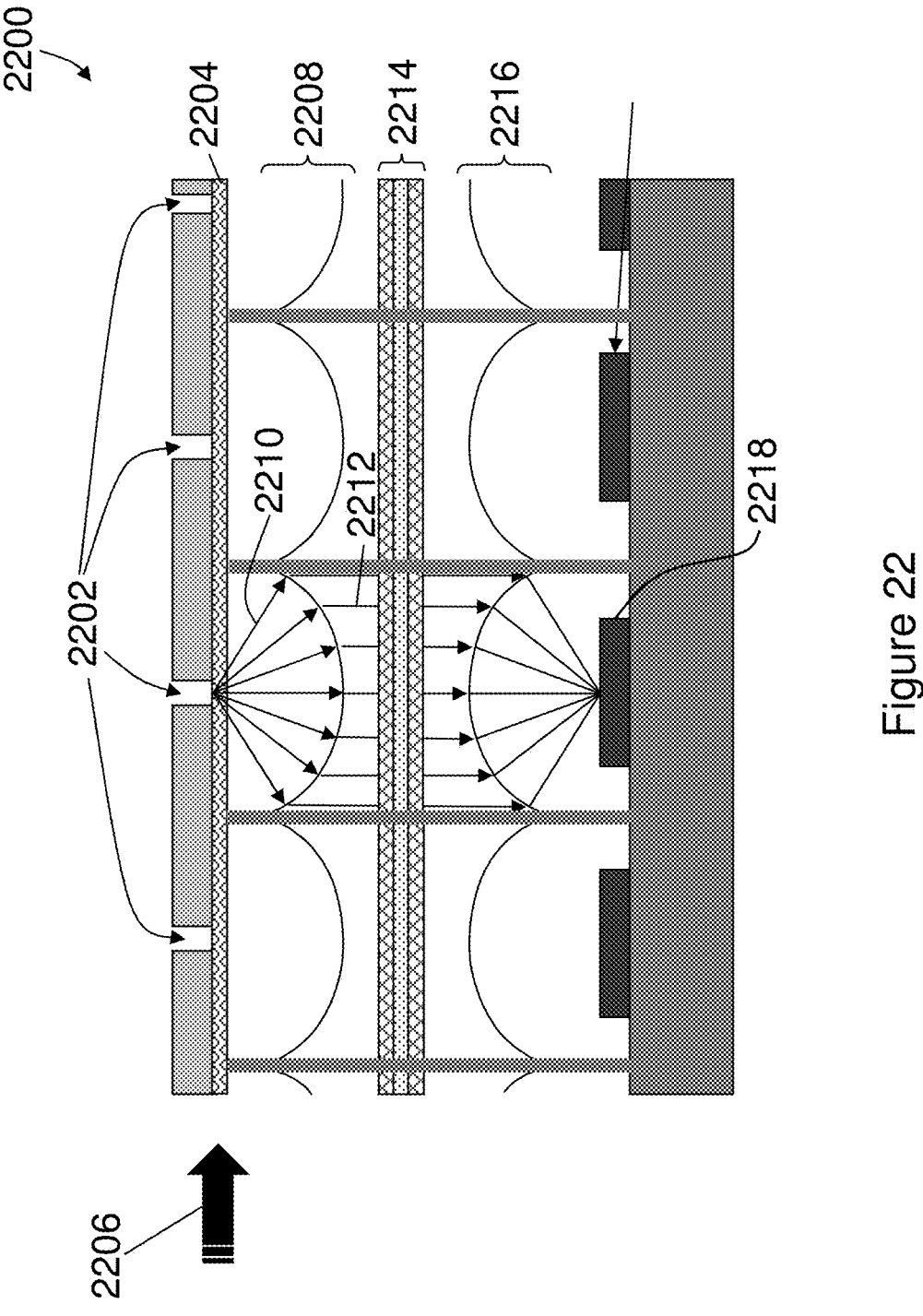
FIG. 22 schematically illustrates an embodiment of an integrated optical device comprising a waveguide substrate, a plurality of integrated microarrays, and a detector.

FIG. 22 provides a cross-sectional view of an illustrative embodiment of such an integrated device 2200 in which nanoholes 2202 (or ZMWs) are fabricated on top of a planar or channel waveguide 2204 in which optical energy 2206, e.g., illumination light, is propagated. A first microlens array 2208 is positioned beneath the waveguide layer near the nanoholes (or ZMWs), and the microlenses therein can be fabricated at a micrometer pitch with a larger numerical aperture than, e.g., a single objective lens positioned under the waveguide intended to capture light from all the arrayed nanoholes (or ZMWs). In certain embodiments, each of the microlenses collects the photons (depicted as diverging arrows, e.g., 2210) emitted from a single nanohole (or ZMW) and sends a collimated beam (e.g., 2212) downward. The collimated beam, e.g., of fluorescent light, passes through a notch filter layer 2214 that rejects unwanted scattering light and/or autofluorescence noise. A second microlens array layer 2216 is positioned in front of a detector to focus the collimated light onto each pixel 2218 of the detector. To reduce the need for complex, spectral-splitting, free-space optical components, such as a wedge or multichannel dichroic filter, the system can also use a single color mode in which the excitation radiation is gate, with the excitation lasers working at a pulse mode that matches the detection gating. Therefore, a spectral splitter would not be needed because each different wavelength of optical energy would be propagated though the waveguide in a temporally separate manner, e.g., one at a time. (Methods for pulse mode excitation are provided, e.g., in U.S. Patent Publication No. 20090181396, incorporated herein by reference in its entirety for all purposes.) As such, this optical system provides a set of micrometer-scale imaging optics for each nanohole (or ZMW). The pitch of the microlens arrays can be chosen to match the pitch of the pixels on a detector. With essentially no limitation on the FOV, the multiplex capabilities of the optical system are vastly increased over more traditional free-space optical systems previously used with ZMW arrays.

Figure 23:
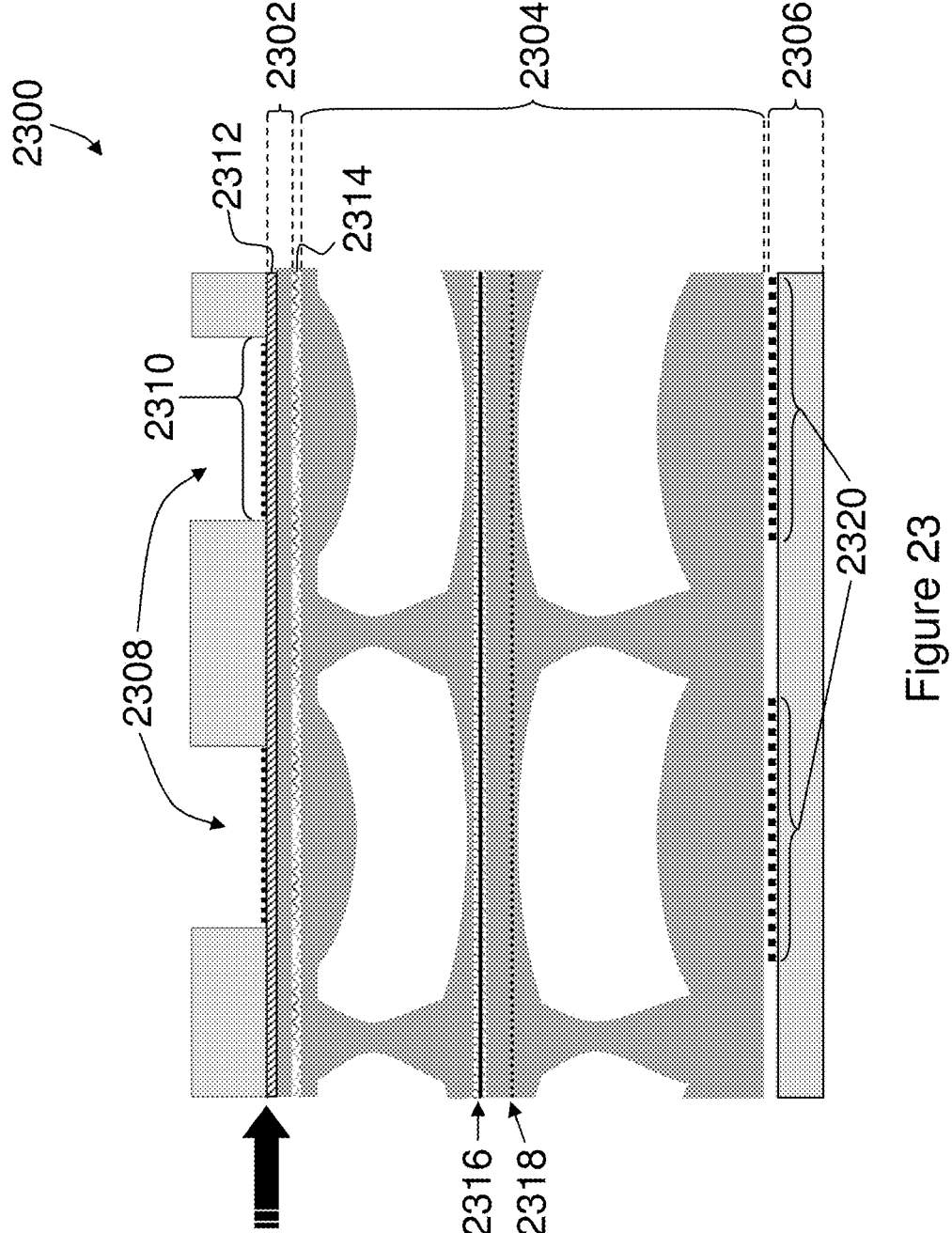
FIG. 23 schematically illustrates an embodiment of an integrated optical device comprising a waveguide substrate, a plurality of integrated microarrays, and a sensor array.

FIG. 23 provides a further embodiment of a device comprising an integrated optical system with microlens arrays. Three major components of device 2300 are shown in the cross-sectional representation: (1) a waveguide substrate layer 2302, (2) a wafer-level lens array layer 2304, and (3) a sensor array layer 2306. The waveguide substrate layer 2302 comprises a plurality of reagent wells 2308, each of which comprises a biosensing region (e.g., 2310) with an array of nanoholes (or ZMWs). The waveguide 2312 (e.g., core and cladding) is located in the waveguide substrate layer 2302, and may be a planar waveguide, or a series of channel waveguides, as described elsewhere herein. The waveguide 2312 delivers optical energy to reaction sites in the biosensing regions (e.g., 2310), e.g., at the bottom of the nanoholes (or ZMWs). The wafer-level lens array layer 2304 comprises multiple "mini objective lenses" formed from several layers of microlenses, and is positioned under the waveguide substrate layer 2302. To reach high numerical aperture for increased collection efficiency, an immersion fluid layer 2314 can optionally be implemented to optically connect the waveguide substrate layer 2302 and the wafer-level lens array layer 2304. Dielectric coatings (e.g., dielectric notch filters 2316) to block laser light can be integrated into the wafer-level lens array, and dispersive gratings 2318 (or Fresnel wedge(s)) can also be integrated at the wafer level to spread light and facilitate detection. For example, fluorescent light of differing wavelengths can be spread to facilitate detection of the individual wavelengths. The sensor array layer 2306 (e.g., comprising CMOS, CCD, etc.) is positioned under the wafer-level lens array layer 2304, and comprises multiple discrete sensor arrays 2320, each of which is aligned with one of the mini objective lenses in the wafer-level lens array layer 2304. Each of the sensor arrays 2320 images emission signals from nanoholes (or ZMWs) within a given reagent well. As will be clear, the device depicted in FIG. 23 is merely one example of an integrated optical system device of the invention, and other variations and substitutions on this illustrative example are contemplated. For example, such devices may comprise additional microlens layers, different layouts, different types of optical components (e.g., gratings, mirrors, lenses, couplings, filters, etc.), and the like.

Since all the layers a device comprising integrated optical components (e.g., as described above) can be made at the waveguide substrate level, the device can be to be scaled to extremely high multiplex. For example, a waveguide substrate could comprise a 10×10 array of parallel reagent wells, with each well having dimensions of about 1×1 mm and containing approximately 32,000 nanoholes (or ZMWs). The total multiplex of this exemplary device is 3.2 million; i.e., 3.2 million separate analytes or analytical reactions can be individually and simultaneously monitored in real time with such a device. This level of multiplex far exceeds what conventional free space optics typically achieves. A further advantage over systems utilizing free space optics is that alignment of the multiple lens arrays in the integrated optics devices is readily achieved using standard microlithography techniques, and once assembled the device is far less sensitive to vibration or thermal drift. In addition, the advantages of waveguide illumination over free space illumination also apply and include, e.g., spatially confined autofluorescence, lower input power requirements, smaller size and weight, and lower costs for manufacturing, packaging, and the like.

In certain preferred embodiments, one or more multilayer dielectric stacks that have been tuned to have particular reflectance properties are components of an optical system that is integrated into a device for single-molecule (e.g., single-reaction-site) detection. One example of such a tuned dielectric stack is a dielectric omnidirectional reflector (or "mirror"). In preferred embodiments, the reflectance properties include reflection over a wide range of angles and polarizations for particular wavelengths (e.g., excitation illumination wavelengths) combined with permission of other wavelengths (e.g., emission wavelengths). Although not technically a "waveguide" as described elsewhere herein, a dielectric reflector serves a function similar to that of a waveguide in a waveguide substrate. However, while waveguide substrates are typically angle selective with regards to containment or transmission of optical energy, dielectric reflectors are typically wavelength selective and can be fabricated to reflect a first set of wavelengths (e.g., excitation illumination wavelengths) while allowing passage of a second set of wavelengths (e.g., emission illumination wavelengths). In certain aspects, such a device comprises multiple layers: a substrate comprising one or more nanoholes or ZMWs, a mask layer over the surface of the substrate, and a dielectric omnidirectional reflector under the substrate. Dielectric omnidirectional reflectors are known in the art, e.g., in Deopura, et al. (2001) Optics Letters 26 (15):1197-1199; and Fink, et al. (1998) Science 282:1679-1682, both of which are incorporated herein by reference in their entireties for all purposes. In certain preferred embodiments, a dielectric omnidirectional reflector comprises a stack of dielectric layers that are configured to reflect optical energy from an energy source at one or more excitation wavelengths, while permitting transmission of optical energy emitted from nanoholes or ZMWs (emission radiation) to an optical detection system. The mask layer comprises material that reflects optical energy, and in particular excitation radiation from the optical energy source; in preferred embodiments, at least the portion of the mask layer in contact with the substrate is a metal (e.g., aluminum, gold, silver, platinum, and the like) that reflects essentially all the excitation radiation back down into the substrate layer. The trapping of the optical energy within the substrate layer can be adjusted or "tuned" by methods known to the skilled practitioner to achieve a desired level and/or wavelength(s) of reflection of the optical energy, and the desired reflection is chosen based on various factors including, but not limited to, a tolerance of the system to autofluorescence generated by such reflection, and the quantity of heat that can be dissipated from the device. One or more nanoholes or ZMWs may optionally be disposed within a confinement on the surface of the substrate, e.g., a well or channel. In typical implementation, the layers of the device are fabricated separately by different processes that achieve the specific specification requirements for each layer. After fabrication, the layers are aligned with one another during assembly of the device. Manufacture and precise alignment of the layers can be achieved by known methods, e.g., based on conventional semiconductor or microarray fabrication processes, and so are within the level of one of ordinary skill in the art.

Figure 24:
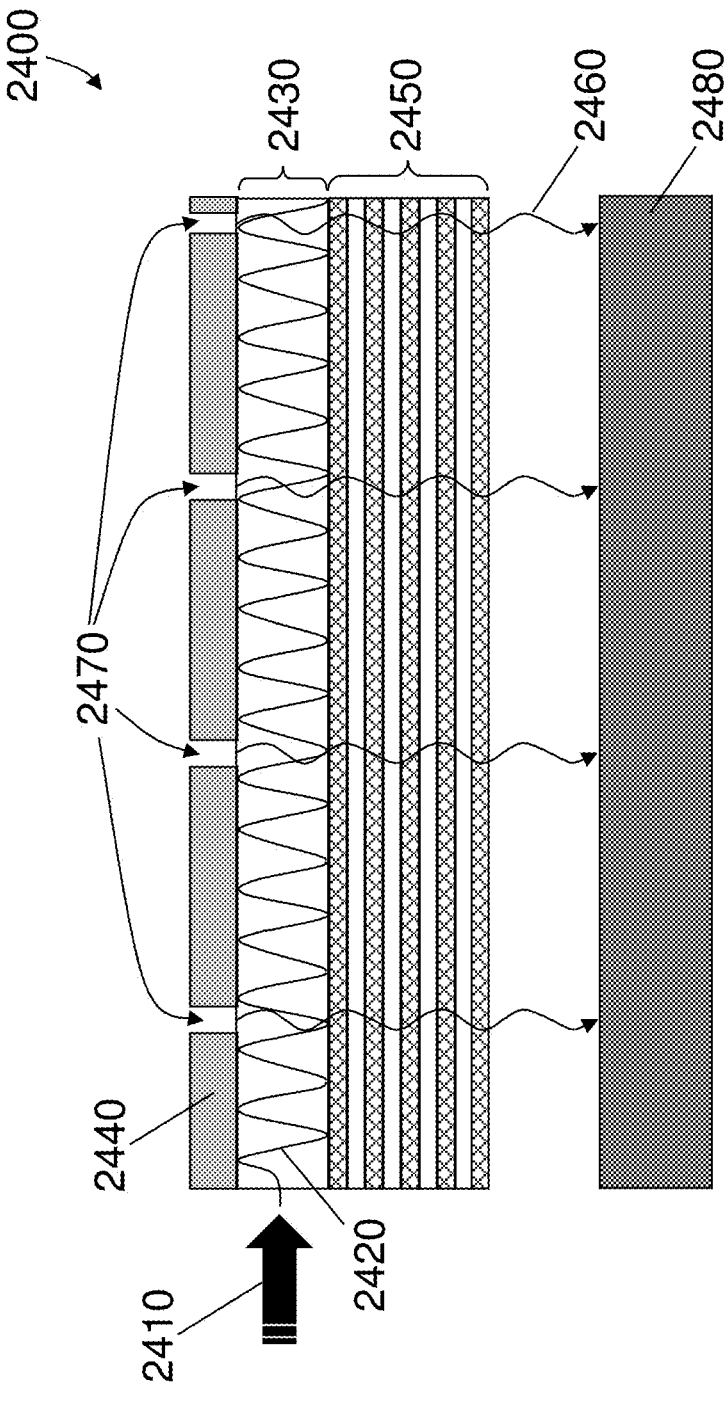
FIG. 24 schematically illustrates an embodiment of a device of the invention comprising a dielectric omnidirectional reflector.

FIG. 24 provides an illustrative example of a preferred embodiment of the invention. Device 2400 comprises an optical energy source 2410 (e.g., a laser, light emitting diode, or other narrow emission source) delivers optical energy 2420 (e.g., of one or more excitation wavelengths) to the edge of substrate 2430 where it passes into the substrate to be propagated between mask layer 2440 and dielectric omnidirectional reflector 2450. Dielectric omnidirectional reflector 2450 reflects optical energy 2420 into substrate 2430, but permits passage of optical energy 2460 emitted from nanoholes or ZMWs 2470 (emission radiation) through the reflector 2450 to an optical detection system 2480.

The use of a dielectric omnidirectional reflector to propagate optical energy in a single-molecule detection device provides many of the same benefits as use of waveguide illumination, including mitigation of misalignment of an optical energy source and a biosensing region(s) on a substrate. In addition, an omnidirectional dielectric reflector may be integrated within a substrate, placed in direct contact with a substrate, or may be positioned such that a layer of air (or other gas, fluid, etc.) separates the reflector from the substrate. Further, such devices can be used to illuminate various types of reaction sites, e.g. reaction sites located within nanoholes or zero-mode waveguides, or illumination of other types of analytical reaction systems known in the art.

Those of ordinary skill in the art will understand that various changes in form and detail can be made to the substrates, waveguides, dielectric reflectors, and nanoholes provided herein. For example, variation of the nanohole geometry can vary the optical field produced within the waveguide core, as well as the observation volume being illuminated by the field. Further, different waveguide geometries can be used to deliver excitation radiation to the nanoholes, including various arrangements of channel waveguides and/or planar waveguides, some of which are described elsewhere herein. In particular, single analytes, molecules, molecular complexes can be detected, monitored, and analyzed in real time, e.g., during the course of an analytical reaction.

III. Methods and Applications

As noted previously, the substrates, systems and methods of the invention are broadly applicable to a wide variety of analytical methods. In particular, the waveguide substrates of the invention may be employed in the illumination-mediated analysis of a range of materials that are disposed upon or proximal to the substrate's surface. Such analyses include, inter alia, a number of highly valued chemical, biochemical and biological analyses, including nucleic acid analysis, protein interaction analysis, cellular biology analysis, and the like.

Exemplary Applications

1. Sequencing by Synthesis

One example of an analytical operation in which the present invention is particularly applicable is in the determination of nucleic acid sequence information using sequence-by-synthesis processes. Briefly, sequencing-by-synthesis exploits the template-directed synthesis of nascent DNA strands, e.g., using polymerase-mediated strand extension, and monitors the addition of individual bases to that nascent strand. By identifying each added base, one can deduce the complementary sequence that is the sequence of the template nucleic acid strand. A number of "sequence-by-synthesis" strategies have been described, including pyrosequencing methods that detect the production of pyrophosphate upon the incorporation of a given base into the nascent strand using a luminescent luciferase enzyme system as the indicating event. Because the indicator system is generic for all four bases, the process requires that the polymerase/template/primer complex be interrogated with only one base at a time.

Other reported sequence-by-synthesis methods employ uniquely labeled nucleotides or nucleotide analogs such that the labels provide both an indication of incorporation of a base, as well as indicate the identity of the base (See, e.g., U.S. Pat. No. 6,787,308, incorporated herein by reference in its entirety for all purposes). Briefly, these methods employ a similar template/primer/polymerase complex, typically immobilized upon a solid support, such as a planar or other substrate, and interrogate it with nucleotides or nucleotide analogs that may include all four bases, but where each type of base bears an optically detectable label that is distinguishable from the other bases. These systems employ terminator bases, e.g., bases that, upon incorporation, prevent further strand extension by the polymerase. Once the complex is interrogated with a base or mixture of bases, the complex is washed to remove any non-incorporated bases. The washed extended complex is then analyzed using, e.g., four color fluorescent detection systems, to identify which base was incorporated in the process. Following additional processing to remove the terminating group, e.g., using photochemistry, and in many cases, the detectable label, the process is repeated to identify the next base in the sequence. In some cases, the immobilized complex is provided upon the surface as a group of substantially identical complexes, e.g., having the same primer and template sequence, such that the template mediated extension results in extension of a large number of identical molecules in a substantially identical fashion, on a step wise basis. In other strategies, complexes are immobilized in a way that allows observation of individual complexes resulting in a monitoring of the activity of individual polymerases against individual templates.

As will be appreciated, immobilization or deposition of the polymerase/template/primer complex upon or proximal to the surface of the waveguide core in the waveguide arrays of the invention will allow illumination, and more notably in the case of fluorescence-based assays, excitation, at or near selected regions of the surface without excessive activation and fluorescence interference from the surrounding environment, which can be a source of significant noise in fluorescence based systems.

In another sequencing-by-synthesis process, one monitors the stepwise addition of differently labeled nucleotides as they are added to the nascent strand and without the use of terminator chemistries. Further, rather than through a one-base-at-a-time addition strategy, monitoring of the incorporation of bases is done in real time, e.g., without the need for any intervening wash steps, deprotection steps or separate de-labeling steps. Such processes typically rely upon optical strategies that illuminate and detect fluorescence from confined reaction volumes, such that individual complexes are observed without excessive interference from labeled bases in solution that are not being incorporated (See U.S. Pat. Nos. 6,991,726 and 7,013,054, previously incorporated herein, and U.S. Pat. Nos. 7,052,847, 7,033,764, 7,056,661, and 7,056,676, the full disclosures of which are incorporated herein by reference in its entirety for all purposes), or upon labeling strategies that provide fluorescent signals that are indicative of the actual incorporation event, using, e.g., FRET dye pair members on a base and on a polymerase or template/primer (See U.S. Pat. Nos. 7,052,847, 7,033,764, 7,056,661, and 7,056,676, supra).

In accordance with the foregoing sequence-by-synthesis methods, one may optionally provide the complexes over an entire surface of a substrate, or one may selectively pattern the immobilized complexes upon or proximal to the waveguide cores. Patterning of complexes may be accomplished in a number of ways using selectively patternable chemical linking groups, and/or selective removal or ablation of complexes not in the desired regions. In some cases, one can employ the waveguides in selectively patterning such complexes using photoactivatable chemistries within the illumination region. Such strategies are described in detail in U.S. patent application Ser. No. 11/394,352 filed Mar. 30, 2006, the disclosure of which is incorporated herein by reference in its entirety for all purposes.

In addition to selective immobilization, and as noted above, in some cases it is desirable to immobilize the complexes such that individual complexes may be optically resolvable, e.g., distinguished from other complexes. In such cases, the complexes may be immobilized using highly dilute solutions, e.g., having low concentrations of the portion of the complex that is to be immobilized, e.g., the template sequence, the polymerase or the primer. Alternatively, the surface activation for coupling of the complex component(s) may be carried out to provide a low density active surface to which the complex will be bound. Such surfaces have been described in U.S. patent application Ser. No. 11/240,662, filed Sep. 30, 2005, which is incorporated herein by reference in its entirety for all purposes. Again, such low density complexes may be patterned just upon or proximal to the waveguides or they may be provided across the surface of the substrate, as only those reaction complexes that are proximal to the waveguides will yield fluorescent signals.

While described in terms of real-time nucleic acid sequencing-by-synthesis, it will be appreciated that a wide variety of real-time, fluorescence based assays may be enhanced using the waveguide arrays and methods of the invention. In particular, the waveguide array systems provided herein facilitate simultaneous illumination and detection of multiple fluorophores of multiple different wavelengths is real time for a variety of experimental systems.

2. Molecular Arrays and Other Surface Associated Assays

Another exemplary application of the waveguide arrays of the invention is in molecular array systems. Such array systems typically employ a number of immobilized binding agents that are each specific for a different binding partner. The different binding agents are immobilized in different known or readily determinable locations on a substrate. When a fluorescently labeled material is challenged against the array, the location to which the fluorescently labeled material binds is indicative of its identity. This may be used in protein-protein interactions, e.g., antibody/antigen, receptor-ligand interactions, chemical interactions, or more commonly in nucleic acid hybridization interactions. See, U.S. Pat. Nos. 5,143,854, 5,405,783 and related patents, and GeneChip® systems from Affymetrix, Inc.

In accordance with the application of the invention to arrays, a number of binding regions, e.g., populated by known groups of nucleic acid probes, are provided upon a substrate surface upon or proximal to the waveguides such that a hybridized fluorescently labeled probe will fall within the illumination region of the waveguide. By providing for selective illumination at or near the surface, one can analyze hybridized probes without excessive interference from unbound fluorescent materials. Further details regarding this aspect of the invention can be found in Lundquist et al. U.S. Patent Publication No. 2008/0128627, the full disclosure of which is incorporated herein by reference in its entirety for all purposes.

3. Cellular Observation and Analysis

In still another exemplary application, cell-based assays or analyses may be carried out by providing cells adhered to the substrate surface over the waveguides. As a result, one could directly monitor fluorescently labeled biological functions, e.g., the uptake of fluorescent components, the generation of fluorescent products from fluorogenic substrates, the binding of fluorescent materials to cell components, e.g., surface or other membrane coupled receptors, or the like.

4. Other Applications

It will be appreciated by those of ordinary skill that the substrates of the invention may be broadly applicable in a wider variety of applications that monitor analytical processes, including but not limited to those provided in U.S. Patent Application Nos. 61/186,645 and 61/186,661, both of which were filed Jun. 12, 2009 and are incorporated herein by reference in their entireties for all purposes. In addition, such substrates and methods may be employed in the identification of location of materials on surfaces, the interrogation of quality of a given process provided upon the surface, the photo-manipulation of surface bound materials, e.g., photo-activation, photo-conversion and/or photo-ablation. As such, while some of the most preferred applications of the present invention relate to analytical operations and particularly in the fields of chemistry, biochemistry, molecular biology and biology, the discussion of such applications in no way limits the broad applicability of the invention.

While the foregoing invention has been described in some detail for purposes of clarity and understanding, it is to be understood that the above description is intended to be illustrative and not restrictive. It will be clear to one skilled in the art from a reading of this disclosure that various changes in form and detail can be made to the inventions disclosed herein without departing from the true scope and spirit of the invention. For example, all the techniques and apparatus described above can be used in various combinations. The scope of the invention should, therefore, be determined not with reference to the above description, but should instead be determined with reference to the appended claims, along with the full scope of equivalents to which such claims are entitled. All publications, patents, patent applications, and/or other documents cited in this application are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes to the same extent as if each individual publication, patent, patent application, and/or other document were individually indicated to be incorporated by reference for all purposes.

The invention claimed is:

1. An integrated analytical device for detecting single molecules, comprising:
a plurality of nanoholes disposed in a mask layer above a substrate;
an optical grating coupling an optical illumination energy source to the substrate;
a reflector positioned below the substrate; and
an optical detection system positioned to receive optical energy emitted from reaction sites of the nanoholes;
wherein the substrate is a waveguide substrate;
wherein the optical energy comprises a laser beam;
wherein the reflector is a dielectric omnidirectional reflector comprising a stack of dielectric layers;
wherein the reflector reflects illumination from the optical energy source; and
wherein the integrated analytical device is configured to detect single molecules in the reaction sites of the nanoholes.

2. The analytical device of claim 1, wherein the optical detection system comprises pixels.

3. The analytical device of claim 1 or 2, wherein the portion of the reflector that is positioned between the nanohole and a detector permits passage of optical energy emitted from nanoholes through the reflector to the optical detection system.

4. The analytical device of claim 1, further comprising a microlens array that directs light from the reaction sites to the pixels.

5. The analytical device of claim 1, wherein the mask layer is a metal.

6. The analytical device of claim 1, wherein the integrated analytical device is configured to perform single molecule nucleic acid sequencing.

7. The analytical device of claim 1, wherein the integrated analytical device is configured to detect protein interactions.

8. A method of detecting single molecules, comprising:
a) providing an integrated analytical device comprising: a plurality of nanoholes disposed in a mask layer above a substrate;
an optical coupling an optical illumination energy source to the substrate;
a reflector positioned below the substrate; and
an optical detection system positioned to receive optical energy emitted from reaction sites of the nanoholes;
wherein the substrate is a waveguide substrate;
wherein the optical energy comprises a laser beam;
wherein the reflector is a dielectric omnidirectional reflector comprising a stack of dielectric layers;
wherein the reflector reflects illumination from the optical energy source; and wherein the integrated analytical device is configured to detect single molecules in the reaction sites of the nanoholes;

b) illuminating reaction sites of the nanoholes;

c) detecting, at the optical detection system, light emitted from single molecules of the reaction sites.

9. The method of claim 8, wherein the optical detection system comprises pixels.

10. The method of claim 8 or 9, wherein the portion of the reflector that is positioned between the nanohole and a detector permits passage of optical energy emitted from nanoholes through the reflector to the optical detection system.

11. The method of claim 8, wherein the integrated analytical device further comprises a microlens array that directs light from the reaction sites to the pixels.

12. The analytical device of claim 1, wherein the mask layer is a metal.

13. The analytical device of claim 8, wherein step c) comprises single molecule nucleic acid sequencing.

14. The analytical device of claim 8, wherein step c) comprises detecting protein interactions.

\* \* \* \* \*